US009920086B2

(12) United States Patent
Stephan et al.

(10) Patent No.: US 9,920,086 B2
(45) Date of Patent: Mar. 20, 2018

(54) RUTHENIUM-BASED COMPLEXES, THEIR PREPARATION AND USE AS CATALYSTS

(71) Applicants: LANXESS Deutschland GmbH, Cologne (DE); THE GOVERNING COUNCIL OF THE UNIVERSITY OF TORONTO, Toronto (CA)

(72) Inventors: Douglas Wade Stephan, Toronto (CA); Clinton Lund, London (CA); Michael Sgro, Toronto (CA); Fatme Dahcheh, Mississauga (CA); Christopher Ong, Orange, TX (US)

(73) Assignees: ARLANXEO DE GMBH, Dormagen (DE); THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 212 days.

(21) Appl. No.: 14/892,451

(22) PCT Filed: May 20, 2014

(86) PCT No.: PCT/EP2014/060356
§ 371 (c)(1),
(2) Date: Nov. 19, 2015

(87) PCT Pub. No.: WO2014/187830
PCT Pub. Date: Nov. 27, 2014

(65) Prior Publication Data
US 2016/0090396 A1 Mar. 31, 2016

Related U.S. Application Data

(60) Provisional application No. 61/827,152, filed on May 24, 2013.

(30) Foreign Application Priority Data

Jul. 4, 2013 (EP) .................................. 13175095
Sep. 17, 2013 (EP) .................................. 13184655

(51) Int. Cl.
| | | |
|---|---|---|
| C07F 15/00 | (2006.01) |
| B01J 31/00 | (2006.01) |
| C08F 236/12 | (2006.01) |
| C08F 8/00 | (2006.01) |
| C08F 4/70 | (2006.01) |
| C08F 4/00 | (2006.01) |
| B01J 31/22 | (2006.01) |
| C08L 9/02 | (2006.01) |
| C08C 19/00 | (2006.01) |

(52) U.S. Cl.
CPC .......... *C07F 15/0046* (2013.01); *B01J 31/00* (2013.01); *B01J 31/2278* (2013.01); *C08F 4/00* (2013.01); *C08F 4/70* (2013.01); *C08F 8/00* (2013.01); *C08F 236/12* (2013.01); *C08L 9/02* (2013.01); *B01J 2231/543* (2013.01); *B01J 2531/821* (2013.01); *C08C 2019/09* (2013.01)

(58) Field of Classification Search
CPC .................................................. C07F 15/0046
See application file for complete search history.

(56) References Cited

U.S. PATENT DOCUMENTS

| | | | |
|---|---|---|---|
| 5,969,170 A | 10/1999 | Grubbs et al. |
| 7,745,539 B2 | 6/2010 | Guerin et al. |
| 7,951,875 B2 | 5/2011 | Guerin et al. |
| 8,604,141 B2 | 12/2013 | Grubbs et al. |
| 2015/0057450 A1 | 2/2015 | Jeschko et al. |

FOREIGN PATENT DOCUMENTS

| | | | |
|---|---|---|---|
| EP | 0419952 A1 | 4/1991 | |
| JP | 2001-97988 | * 4/2001 | .......... C07F 15/0046 |

OTHER PUBLICATIONS

Kodama et al., Machine translation of JP 2001-97988.*
Monfette, Sebastien et al., "Electronic Effects of the Anionic Ligan in Ruthenium-Catalyzed Olefin Metathesis", Organometallics, 2009, 298 (4) pp. 944-946, American Chemical Society, Abstract.
Lund, Clinton et al, "Neutral and Cationic Tridentate Bis(N-heterocycli carbene) Ether Ruthenium Alkylidene Complexes in Metathesis", Organometallics, 2012, 31 (2), pp. 580-587, American Chemical Society, Abstract.
Bantrell, Xavier, et al. "Ruthenium, Complexes Bearing Two N-Heterocyclic Carbene Ligands in Low Catalyst Loading Olefin Metathesis Reactions", Organometallics, 2010, 29 (13), pp. 3007-3011, American Chemical Society, Abstract.
Salem, Hiyam et al., "Bulky N-Phosphinomethyl-Functionalized N-Heterocyclic Carbene Chelate Ligands: Synthesis, Molecular Geometry, Electronic Structure, and Their Ruthenium Alkylidene Complexes", Organometallics, 2013, 32 (1), pp. 29-46, American Chemical Society, Abstract.
Wilhelm, Thomas E et al., "Reactivity of Ru(H)(H2)(Ci(PCy3)2 with Propargyl and Vinyl Chlorides: New Methodology to Give Metathesis-Active Ruthenium Carbenes", Organometallics, 1997, 16 (18), pp. 3867-3869, American Chemical Society, Abstract.
Conrad, Jay C., et al., "Concise Route to Highly Reactive Ruthenium Metathesis Catalysts Containing a Labile Donor and an N-Heterocyclic Carbene (NHC) Ligand", Organometallics, 2003, 22 (10), pp. 1986-1988, American Chemical Society, Abstract.
Conrad Jay C., et al, "The First Highly Active, Halide-Free Ruthenium Catalyst for Olefin Metathesis", Organometallics, 2003, 22 (18) pp. 3634-3636, American Chemical Society, Abstract.
Monfette, Sebastien, et al., "Ruthenium Metathesis Catalysts Containing Chelating Aryloxide Ligands", Organometallics, 2006, 25 (8), pp. 1940-1944, American Chemical Society, Abstract.
Monfette, Sebastien, et al., "Electonic Effects of the Anionic Ligand in Ruthenium-Catalyzed Olefin Metathesis", Organometallics, 2009, 29 (4), pp. 944-946, American Chemical Society, Abstract.

(Continued)

*Primary Examiner* — Joseph R Kosack

(57) ABSTRACT

The present invention relates to novel Ruthenium-based complex compounds which represent viable catalysts, in particular for all sorts of metathesis reactions. Such complex compounds can be prepared by a novel, very favorable and cost efficient method which includes the introduction of an alkylidene ligand into the complex by using vinyl sulfides or vinyl ethers.

18 Claims, No Drawings

(56) References Cited

OTHER PUBLICATIONS

Pruhs, Stefan et al., "Preparation, R3activity, and Structural Peculiarities of Hydroxyalkyl-Functionalized "Second-Generation" Ruthenium Carbene Complexes", Organometallics, 2004, 23 (2), pp. 280-297, American Chemical Society, Abstract.
Volland, Martin A.O., et al, An 'Old Hydride' in a new synthesis: a convenient approach to Grubbs-type carbene xplexes (PPh3)2Cl2Ru=CH-CH=CR2 and their hexacoordinate acetonitries adducts, J. Org. Chem. 641 (2002), Elsevier, pp. 220-226.
Ferrando, German et al., "Facile C(sp2)/O2CR bond cleavage by Ru or Os", New J. Chem., 2003, 27, Royal Society of Chemistry, pp. 1451-1462.
Weskamp, Thomas, et al, A Novel Class of Ruthenium Catalysts for Olefin Metathesis, Angew. Chem, Int. Ed. 1998, 37, No. 18 Wiley-VCH Verlag GmbH, p. 2490.
Vorfalt, Tim, et al. "An (NHC) (NHCewg)RuCl2(ChPh)] Complex for the Efficient Formation of Sterically Hindered Olefins by Ring-Closing Metathesis", Angew. Chem, Int. Ed, 2009, 48, Wiley-VCH Verlag GmbH & Co, pp. 5191-5194.
McClelland, Robert A, "Vinyl sulfide hydrolysis", Can. J. Chem, vol. 55, 1977, downloaded on Oct. 4, 2017 at www.nrcresearchpress.com, pp. 548-551.
Bhadra, Sukalyan, et al. "Water-romoted regioselective hydrothiolation of alkynes", Can. J. Chem. 87 (2009), NRS Research Press, pp. 1605-1609.
Gandelnab, Mark, et al., "A New General Method for the Preparation of Metal CArbene Complexes", J. Am. Chem. Soc. 2001, 123, American Chemical Society, pp. 5372-5373.
Sashuk, Volodymyr, et al., "[(NHC)(NHCewg)RuC12(CHPh] Complexes with Modified NHCewg Llgands for Efficient Ring-Clsoign Metathesis Leading to Tetrasubstituted Olefins", Chem. Eur. J. 2010, 16, Wiley-VCH Verlag GmbH & Co., pp. 3983-3993.
Trnka, Tina M., et al. "synthesis and Activity of Ruthenium Alkylidene Complexes Coordinated with Phosphine and N-Heterocyclic Carbene Ligands", J. Am. Chem. Soc. 2003, 125, American Chemical Society, pp. 2546-2558.
Occhipinti, Giovanni et al., "Simple and Highly Z-Selective Ruthenium-Based Olefin Metathesis Catalyst", J. Am. Chem. Soc., 2013, 135, American Chemical Society, pp. 3331-3334.
Conrad, Jay C., et al., "Highly Efficient Ru-Pseudohalide Catalysts for Olefin Metathesis", J. Am. Chem. Soc. 2005, 127, American Chemical Society, pp. 11882-11883.
Solinas Maurizio, et al., "Hydroformylation of aryloxy ethylenes by Rh/BINAPHOS complex: Catalyst deactivation path and application to the asymmetric synthesis of 2-aryloxypropanoic acids", J. Mol. Catalysis A: Chem, vol. 226, Issue 1, 2005, pp. 141-147, Elsevier, Abstract.
Cooke, Frank, et al., "SilicoOn in Synthesis. 8.1 Vinyltrimethylsilane, a Convenient Ethylene Equivalent for the Snythesis of Vinyl Aryl Sulfides, Vinyl Aryl Sulfoxides, Thiosilylketene Acetals, and Fused Cyclopentenones", J. Org. Chem, 1980, 45, American Chemical Society, pp. 1046-1053.
Jordaan, M., et al., "A DFT computational study of phosphine legand dissociation versus hemilability in a Bruggs-type precatalyst containing a bidentate ligand during alkene metathesis", Molecular Simulation, vol. 34, Nos. 10-15, 2008, Taylor & Francis, pp. 997-1012.
European Search Report from European Application No. 13175095, dated Nov. 26, 2013, one page.

* cited by examiner

RUTHENIUM-BASED COMPLEXES, THEIR PREPARATION AND USE AS CATALYSTS

FIELD OF THE INVENTION

The present invention relates to novel Ruthenium-based complex catalysts, their preparation and their use for catalytic processes, in particular metathesis reactions.

BACKGROUND OF THE INVENTION

Metathesis reactions are used widely in chemical syntheses, e.g. in the form of ring-closing metatheses (RCM), cross metatheses (CM), ring-opening metatheses (ROM), ring-opening metathesis polymerizations (ROMP), cyclic diene metathesis polymerizations (ADMET), self-metathesis, reaction of alkenes with alkynes (enyne reactions), polymerization of alkynes and olefinization of carbonyls. Metathesis reactions are employed, for example, for the synthesis of olefins, for ring-opening polymerization of norbornene derivatives, for the depolymerisation of unsaturated polymers and for the synthesis of telechelic polymers.

A broad variety of metathesis catalysts is known, inter alia, from WO-A-96/04289 and WO-A-97/06185. They have the following general structure:

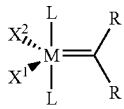

where M is osmium or ruthenium, the radicals R are identical or different organic radicals having a great structural variety, $X^1$ and $X^2$ are anionic ligands and the ligands L are uncharged electron-donors. In the literature, the term "anionic ligands" in the context of such metathesis catalysts always refers to ligands which, when they are viewed separately from the metal centre, are negatively charged for a closed electron shell.

In the last years metathesis reactions have become increasingly important for the degradation of nitrile rubbers also referred to as "NBR" for short, which is typically a copolymer or terpolymer of at least one α,β-unsaturated nitrile, at least one conjugated diene and, if appropriate, one or more further copolymerizable monomers.

Hydrogenated nitrile rubber, referred to as "HNBR" for short, is produced by hydrogenation of nitrile rubber. Accordingly, the C═C double bonds of the copolymerized diene units in HNBR are completely or partly hydrogenated. The degree of hydrogenation of the copolymerized diene units is usually in the range from 50 to 100%. HNBR is a specialty rubber which displays very good heat resistance, excellent resistance to ozone and chemicals and excellent oil resistance combined with very good mechanical properties, such as high abrasion resistance. For this reason, HNBR has found widespread use in a wide variety of applications and is used e.g. for seals, hoses, belts and damping elements in the automobile sector, also for stators, oil well seals and valve seals in the field of crude oil production and for numerous parts in the aircraft industry, the electronics industry, machine construction and shipbuilding.

Most HNBR grades which are commercially available on the market usually have a Mooney viscosity (ML 1+4 at 100° C.) in the range from 55 to 120, which corresponds to a number average molecular weight Mn (determination method: gel permeation chromatography (GPC)) against polystyrene standards) in the range from about 200,000 to 700,000. The polydispersity indices, "PDI", measured (PDI=Mw/Mn, where Mw is the weight average molecular weight and Mn is the number average molecular weight, both determined by GPC against polystyrene standards), which give information about the width of the molecular weight distribution, are frequently 3 or above. The residual double bond content is usually in the range from 1 to 18% (determined by means of NMR or IR spectroscopy). However, it is customary in the art to refer to "fully hydrogenated grades" when the residual double bond content is not more than 0.9%.

The processability of HNBR grades with relatively high Mooney viscosities are subject to restrictions. For many applications HNBR grades which have a lower molecular weight and thus a lower Mooney viscosity are desirable since this significantly improves the processability.

Many attempts have been made in the past to shorten the chain length of HNBR by degradation. For example, a decrease in the molecular weight can be achieved by thermomechanical treatment (mastication), e.g. on a roll mill or in a screw apparatus (EP-A-0 419 952). However, functional groups such as hydroxyl, keto, carboxylic acid and carboxylic ester groups are introduced into the molecule by partial oxidation and, in addition, the microstructure of the polymer is altered substantially.

For a long time, it has not been possible to produce HNBR having a low molar mass corresponding to a Mooney viscosity (ML 1+4 at 100° C.) in the range below 55 or a number average molecular weight of about Mn<200,000 g/mol by means of established production processes since, firstly, a step increase in the Mooney viscosity occurs in the hydrogenation of NBR and secondly the molar mass of the NBR feedstock to be used for the hydrogenation cannot be reduced at will below a certain threshold since otherwise work-up in the industrial plants available is no longer possible because the rubber is too sticky. The lowest Mooney viscosity of an NBR feedstock which can be worked up without difficulties in an established industrial plant is about 30 Mooney units (ML 1+4 at 100° C.). The Mooney viscosity of the HNBR obtained using such an NBR feedstock is in the order of 55 Mooney units (ML 1+4 at 100° C.). The Mooney viscosity is determined in accordance with ASTM standard D 1646.

In the more recent prior art, this problem is solved by reducing the molecular weight of the NBR before hydrogenation by degradation to a Mooney viscosity (ML 1+4 at 100° C.) of less than 30 Mooney units or a number average molecular weight of Mn<70,000 g/mol. The reduction in the molecular weight is achieved by metathesis in which low molecular weight 1-olefins are usually added. The metathesis of NBR is described, e.g. in WO-A-02/100905, WO-A-02/100941 and WO-A-03/002613. The metathesis reaction is advantageously carried out in the same solvent as the hydrogenation reaction so that the degraded nitrile rubber does not have to be isolated from the solvent after the degradation reaction is complete before it is subjected to the subsequent hydrogenation. The metathesis degradation reaction is catalyzed using metathesis catalysts which are tolerant to polar groups, in particular nitrile groups.

WO-A-02/100905 and WO-A-02/100941 describe a process comprising the degradation of NBR by olefin metathesis and subsequent hydrogenation to give HNBR having a low Mooney viscosity. Here, an NBR is reacted in the presence of a 1-olefin and specific complex catalysts based on Os, Ru, Mo, and W in a first step and hydrogenated in a second step. In this way, it is possible to obtain HNBR having a weight average molecular weight (Mw) in the range from 30,000 to 250,000, a Mooney viscosity (ML 1+4 at 100° C.) in the range from 3 to 50 and a polydispersity index PDI of less than 2.5. The metathesis of NBR is described to be carried e.g. using the catalyst bis(tricyclohexylphosphine)benzylideneruthenium dichloride ("Grubbs I") or 1,3-bis(2,4,6-trimethylphenyl)-2-imidazolidenylidene)(tricyclohexyl-phosphine)(phenyl-methylene)ruthenium dichloride ("Grubbs II") as shown below.

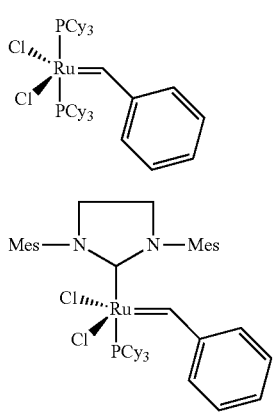

In terms of the molecular weight and the molecular weight distribution, the metathetic degradation using catalysts of the Grubbs (II) type proceeds more efficiently than when catalysts of the Grubbs (I) type are used.

In view of the many applications for metathesis catalysts their synthesis has gained increasing importance.

In J. Am. Chem. Soc. 2001, 123, 5372-5373 the synthesis of metal carbene complexes through the use of a sulfonium salt is reported which is in situ deprotonated to yield a sulfur ylide which then reacts with a metal precursor to yield the corresponding metal carbene complex. Specifically, Grubbs I catalyst is synthesized through this route. This route as shown in the following scheme does not involve ruthenium hydride complexes or vinyl sulfides and does not provide any teaching in this regard.

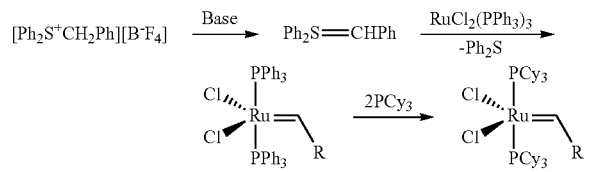

In J. Organomet. Chem. 2002, 641, 220 and Organometallics 2003, 22, 1986-1988 the synthesis of Grubbs-type complexes by reacting (PPh$_3$)$_3$RuHCl and a propargyl chloride is described. The resulting complex can then be transformed into Grubbs I catalysts by alkylidene and phosphine exchange.

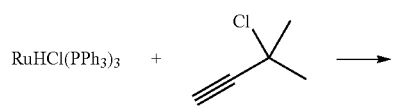

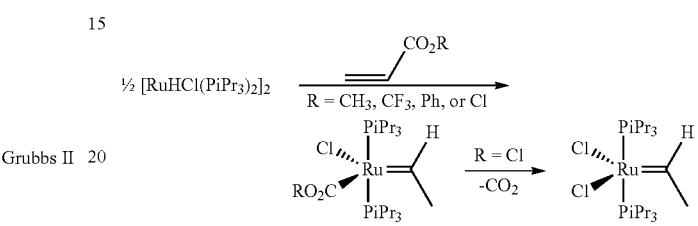

In New. J. Chem. 2003, 27, 1451 the reaction of vinyl chloroformate with a ruthenium hydride starting material is described to yield a ruthenium ethylidene complex through $CO_2$ elimination and chloride migration to the metal centre.

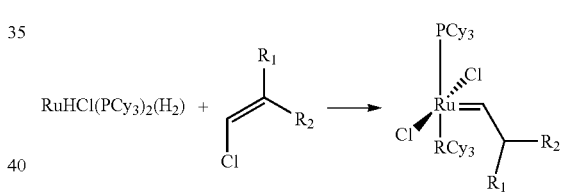

In Organometallics 1997, 16, 3867-3869 the reaction of a ruthenium hydride starting material with propargyl or vinyl halides is described to generate Grubbs-type complexes. It is further mentioned that the reactions of the ruthenium hydride starting material with alkenyl chlorides result in the formation of reactive alkyl carbenes but many by-products were observed which makes this procedure not synthetically viable.

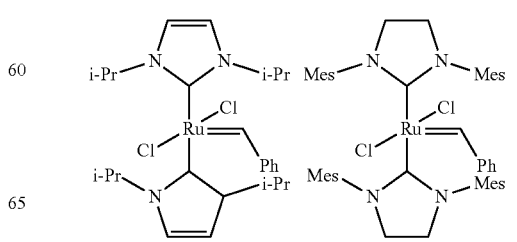

In Angew. Chem. Int. Ed. 1998, 37, 2490, J. Am. Chem. Soc. 2003, 125, 2546, Angew. Chem. Int. Ed. 2009, 48, 5191-5194), Chem. Eur. J. 2010, 16, 3983-3993, and Organometallics 2010, 29, 3007-3011 several examples of olefin metathesis catalysts are shown including those depicted below bearing two N-heterocyclic carbenes as the neutral ligands. N-heterocyclic carbene ligands are in general often referred to as "NHC-ligands". All of the papers either use Grubbs I or Grubbs II catalysts as the ruthenium starting material or use routes that have been described before to generate said Grubbs' catalysts. None of these NHCs feature side arms capable of binding to the metal to form a tridentate ligand.

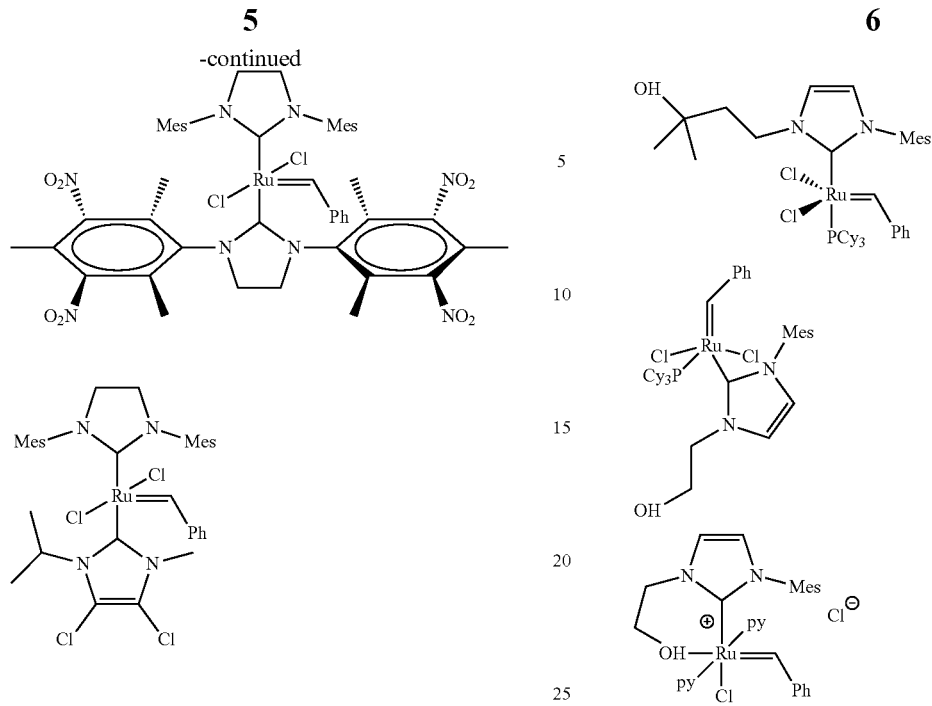

In Organometallics 2003, 22, 3634-3636, J. Am. Chem. Soc. 2005, 127, 11882-11883, Organometallics 2006, 25, 1940-1944 and Organometallics 2009, 28, 944-946 the synthesis and metathesis activities of several ruthenium based catalysts including those depicted below is discussed where one or both the anionic ligands are substituted with either a monodentate or bidentate aryloxy group. These species are obtained using Grubbs-type complexes as the starting materials followed by anion exchange with the appropriate substrate.

Organometallics 2013, 32, 29-46 describes the synthesis of ruthenium alkylidene complexes containing NHC ligands that have a pendant phosphine that binds to the metal upon complexation. A dichloro bridged dimer is first formed and, upon reaction with the appropriate substituted diazomethane, is then converted to the monomeric alkylidene ruthenium complex.

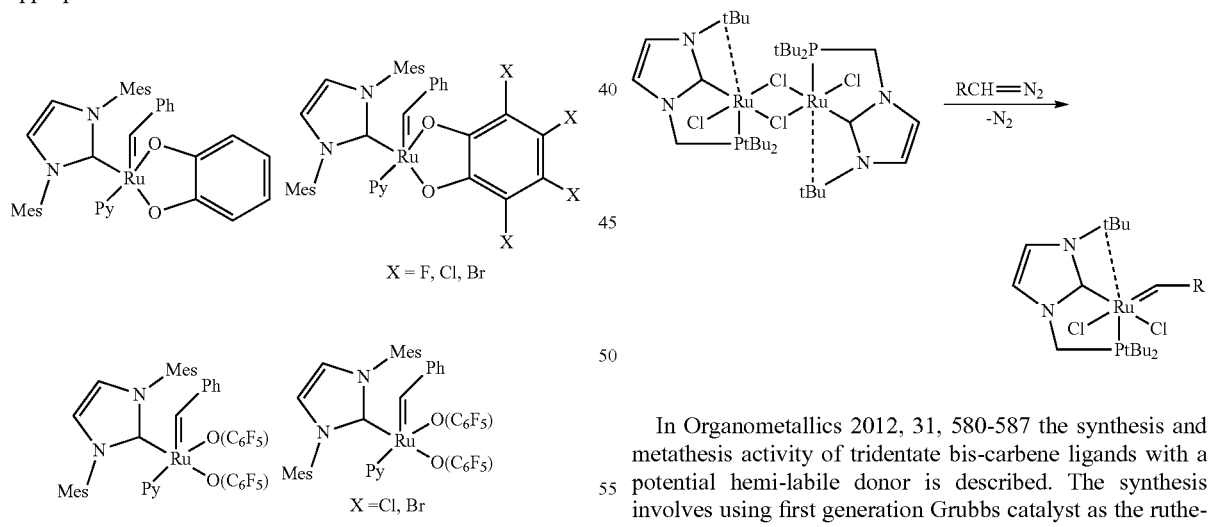

In Organometallics 2004, 23, 280-287 the synthesis of ruthenium benzylidene complexes containing NHC ligands that have hydroxyalkyl chains is described. The neutral ligand can rearrange so that they are cis- rather than trans-disposed. In the presence of pyridine it was shown that the phosphine and one of the chlorides are displaced by 2 equivalents of pyridine and the hydroxyl group coordinates to the metal centre. The complexes below are synthesized using Grubbs I catalyst as the ruthenium starting material.

In Organometallics 2012, 31, 580-587 the synthesis and metathesis activity of tridentate bis-carbene ligands with a potential hemi-labile donor is described. The synthesis involves using first generation Grubbs catalyst as the ruthenium starting material.

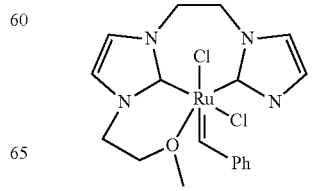

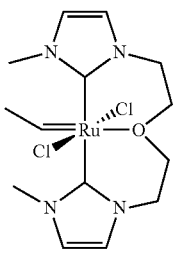

In J. Am. Chem. Soc. 2013, 135, 3331-3334 the synthesis and Z-selective metathesis activity of a thiolate containing Grubbs-Hoveyda type catalyst as shown below is reported where the compound was synthesized starting with Grubbs-Hoveyda catalyst.

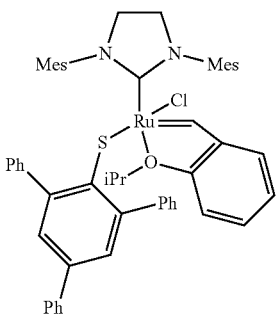

Summing up various catalysts are already available for metathesis reactions, however, many of them contain unfavourable ligands, are sometimes not sufficiently active and/or selective and, importantly, are difficult to prepare or may only be prepared with Grubbs I or II structures as starting materials.

Therefore, it was the object of the present invention to provide an active and thermally robust, novel catalyst which shows on the one hand catalytic activity for a broad variety of metathesis reactions and on the other hand should be accessible via a process route preferably not involving Grubbs I or II structures as starting materials.

SUMMARY OF THE INVENTION

The above-mentioned objects have now been solved by providing novel Ruthenium-based complexes according to general formula (I)

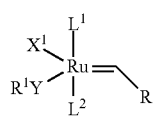

wherein $X^1$ represents an anionic ligand;

Y is O or S, preferably S;

$R^1$ is substituted or unsubstituted $C_6$-$C_{14}$-aryl, an N-heterocyclic carbene ligand or $P(R')_3$ with $R'$ being identical or different and representing either substituted or unsubstituted, straight chain or branched $C_1$-$C_{14}$ alkyl, substituted or unsubstituted $C_6$-$C_{24}$ aryl, or substituted or unsubstituted $C_3$-$C_{20}$ cycloalkyl;

R means substituted or unsubstituted, straight chain or branched $C_1$-$C_{14}$-alkyl, $L^1$ is an N-heterocyclic carbene ligand which is different from general structures (Ia*), (Ib*), (Ic*), and (Id*) defined below for $L^2$;

$L^2$ means a ligand having the general structure (Ia*) or (Ib*)

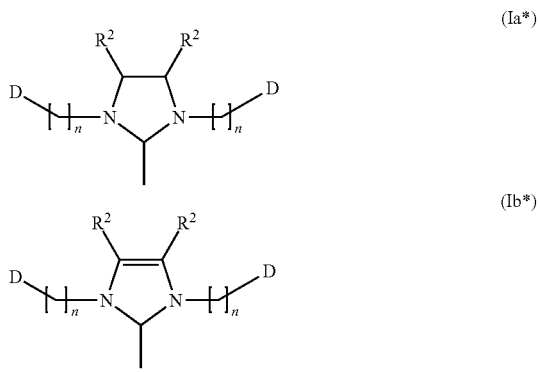

or a ligand having the general structure (Ic*) or (Id*)

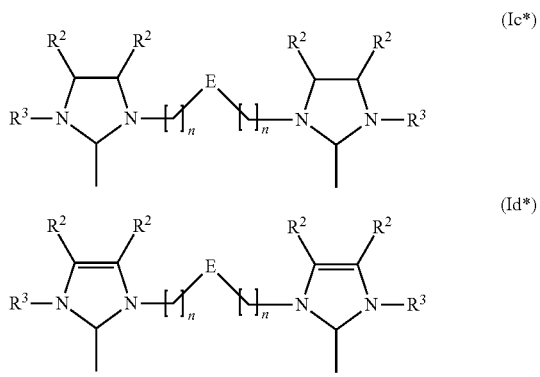

in which formulae (Ia*), (Ib*), (Ic*) and (Id*)

n is identical or different and represents an integer in the range of from 1 to 20, D is identical or different and represents hydroxy, alkoxy, aryloxy, thiol, thiolate, thioether, selenol, selenoether, amine, phosphine, phosphate, phosphite, arsine, sulfoxide, sulfone, alkyl, phosphinimine, aminophosphine, carbene, selenoxide, imidazoline, imidazolidine, phosphine oxide, phosphine sulfide, phosphine selenide, ketone, ester, pyridyl, substituted pyridyl or any moiety able of acting as a two electron donor;

$R^3$ is identical or different and represents H, alkyl or aryl;

E is identical or different and represents a divalent moiety able of acting as a two electron donor selected from the group consisting of —O—, —S—, —Se—, —N(R)—, —P(R)—, —As(R)—, —S(=O)—, —PR(=S)—, —PR(=O)—, —C(=O)—, —C(=S)—, 2,6-pyridylene, substituted 2,6-pyridylene and any other divalent moiety able of acting as a two electron donor; and $R^2$ are identical or different in a respective moiety (Ia*), (Ib*), (Ic*) or (Id*) and represent H, alkyl, aryl, halide, preferably chloride, or in the alternative two $R^2$ together with the two adjacent carbon atoms to which they are bound in a moiety (Ia*), (Ib*), (Ic*) or (Id*) form a fused-on five- or six-membered saturated or unsaturated ring.

The present invention further relates to a method for preparing the complexes of general formula (I), and to using the complexes of general formula (I) as catalysts, in particular for metathesis reactions. In particular the present invention relates to the preparation of nitrile rubbers by subjecting a starting nitrile rubber to a metathesis reaction in the presence of a complex catalyst of general formula (I).

DETAILED DESCRIPTION OF THE INVENTION

The novel Ruthenium-based complexes of general formula (I) are excellently suited as catalysts, in particular for metathesis reactions of a broad variety of unsaturated substrates, and are thermally robust. These catalysts are accessible via a cheap and safe route showing high yields. Favourably the synthesis route does not involve the use of Grubbs I or Grubbs II starting materials and includes the use of vinylsulfides. Surprisingly the reaction with said vinylsulfides affords the generation of an alkylidene ligand and gives rise to the novel alkylidene-thiolate Ru complexes representing highly effective metathesis catalysts.

The term "substituted" used for the purposes of the present patent application means that a hydrogen atom on an indicated radical or atom has been replaced by one of the groups indicated in each case, with the proviso that the valency of the atom indicated is not exceeded and the substitution leads to a stable compound.

For the purposes of the present patent application and invention, all the definitions of radicals, substituents, parameters or explanations given above or below in general terms or in preferred ranges can be combined with one another in any way, i.e. including combinations of the respective ranges and preferred ranges.

Preferred Embodiments of the Complex Catalysts of General Formula (I):

Definition of $X^1$:

In the complex catalysts of the general formula (I), $X^1$ represents an anionic ligand.

$X^1$ can be, for example, hydride, halide, pseudohalide, alkoxide, amide, triflate, phosphate, borate, carboxylate, acetate, halogenated acetate, halogenated alkylsulfonate, tosylate or any weakly coordinating anionic ligands. $X^1$ can also be, for example, straight-chain or branched $C_1$-$C_{30}$-alkyl or $C_6$-$C_{24}$-aryl.

In a preferred embodiment, $X^1$ shall mean halide, in particular fluoride, chloride, bromide or iodide, phosphate, borate, carboxylate, acetate, trifluoroacetate, trifluoromethylsulfonate or tosylate.

In a particularly preferred embodiment, $X^1$ shall mean halide, even ore preferred $X^1$ represents chloride or iodide.

Definition of Y:

Y is either oxygen (O) or sulfur (S), preferably sulfur.

Definition of $L^1$:

$L^1$ is an N-heterocyclic carbene ligand which is different from general structures (Ia*), (Ib*), (Ic*), and (Id*) defined for $L^2$. Typically $L^1$ represents an imidazoline or imidazolidine ligand having a structure corresponding to the general formulae (IIa), or (IIb),

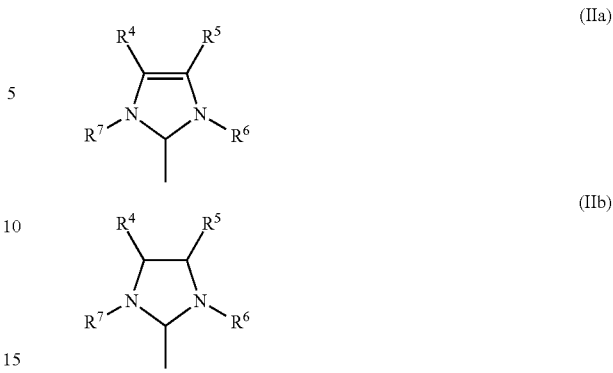

wherein under the proviso that $L^1$ is different from the general formulae (Ia*), (Ib*), (Ic*) and (Id*), $R^4$, $R^5$, $R^6$, $R^7$ are identical or different and are each hydrogen, straight-chain or branched $C_1$-$C_{30}$-alkyl, $C_3$-$C_{20}$-cycloalkyl, $C_2$-$C_{20}$-alkenyl, $C_2$-$C_{20}$-alkynyl, $C_6$-$C_{24}$-aryl, $C_1$-$C_{20}$-carboxylate, $C_1$-$C_{20}$-alkoxy, $C_2$-$C_{20}$-alkenyloxy, $C_2$-$C_{20}$-alkynyloxy, $C_6$-$C_{20}$-aryloxy, $C_2$-$C_{20}$-alkoxycarbonyl, $C_1$-$C_{20}$-alkylthio, $C_6$-$C_{20}$-arylthio, $C_1$-$C_{20}$-alkylsulphonyl, $C_1$-$C_{20}$-alkylsulphonate, $C_6$-$C_{20}$-arylsulphonate or $C_1$-$C_{20}$-alkylsulphinyl or in the alternative $R^6$ and $R^7$ have the above mentioned meanings and at the same time $R^4$ and $R^5$ jointly form a $C_6$-$C_{10}$ cyclic structure together with the two adjacent carbon atoms in the imidazoline or imidazolidine ring.

Again under the proviso that the ligands according to formulae (IIa) and (IIb) are different from the ligand structures (Ia*), (Ib*), (Ic*), and (Id*) one or more of the substituents $R^4$, $R^5$, $R^6$, $R^7$ as defined above can, if appropriate, independently of one another, be substituted by one or more substituents, preferably straight-chain or branched $C_1$-$C_{10}$-alkyl, $C_3$-$C_8$-cycloalkyl, $C_1$-$C_{10}$-alkoxy or $C_6$-$C_{24}$-aryl, where these abovementioned substituents may in turn be substituted by one or more functional groups, preferably functional groups selected from the group consisting of halogen, in particular chlorine or bromine, $C_1$-$C_5$-alkyl, $C_1$-$C_5$-alkoxy and phenyl.

Merely for the sake of clarity, it may be added that the structures of the imidazoline or imidazolidine ligands depicted in the general formulae (IIa) and (IIb) in the present application are equivalent to the structures (IIa'), and (IIb') which are frequently also found in the literature for this type of ligands and emphasize the carbene character of the imidazoline or imidazolidine ligand. This applies analogously to the associated preferred structures (III-a)-(III-o) depicted below and to the structures (Ia*), (Ib*), (Ic*) and (Id*).

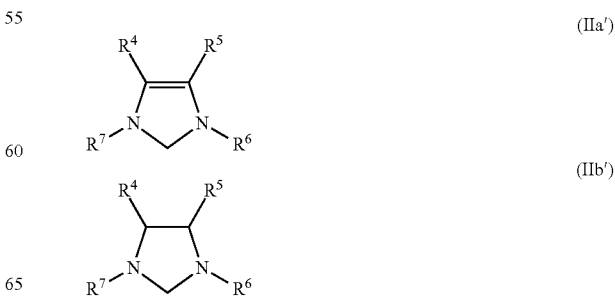

For all following preferred embodiments the same proviso as mentioned above shall apply, i.e. in any case the meanings of $R^4$, $R^5$, $R^6$, $R^7$ shall be chosen in a way that the imidazoline or imidazolidine ligands having the formulae (IIa) and (IIb) (or (IIa') and (IIb') and (III-a)-(III-o), respectively) must be different from the ligands having the formulae (Ia*), (Ib*), (Ic*) or (Id*).

In a preferred embodiment of the catalysts of the general formula (I), $R^4$ and $R^5$ are each, independently of one another, hydrogen, $C_6$-$C_{24}$-aryl, particularly preferably phenyl, straight-chain or branched $C_1$-$C_{10}$-alkyl, particularly preferably propyl or butyl, or together with the carbon atoms to which they are bound form a $C_6$-$C_{10}$ cycloalkyl or $C_6$-$C_{10}$ aryl substituent, preferably a phenyl ring in structure (IIa) (structure (IIa') respectively) where all the above mentioned substituents may in turn be substituted by one or more further substituents selected from the group consisting of straight-chain or branched $C_1$-$C_{10}$-alkyl, $C_1$-$C_{10}$-alkoxy, $C_6$-$C_{24}$-aryl and a functional group selected from the group consisting of hydroxy, thiol, thioether, ketone, aldehyde, ester, ether, amine, imine, amide, nitro, carboxylic acid, disulphide, carbonate, isocyanate, carbodiimide, carboalkoxy, carbamate and halogen.

In a preferred embodiment of the catalysts of the general formula (I), the substituents $R^6$ and $R^7$ are identical or different and are each straight-chain or branched $C_1$-$C_{10}$-alkyl, particularly preferred i-propyl or neopentyl, $C_3$-$C_{10}$-cycloalkyl, particularly preferred adamantyl, $C_6$-$C_{24}$-aryl, particularly preferred phenyl, $C_1$-$C_{10}$-alkylsulphonate, particularly preferred methanesulphonate, $C_6$-$C_{10}$-arylsulphonate, particularly preferred p-toluenesulphonate.

The abovementioned substituents as meanings of $R^6$ and $R^7$ may be substituted by 1, 2 or more further substituents selected from the group consisting of straight-chain or branched $C_1$-$C_5$-alkyl, in particular methyl or i-propyl, $C_1$-$C_5$-alkoxy, optionally substituted aryl and a functional group selected from the group consisting of hydroxy, thiol, thioether, ketone, aldehyde, ester, ether, amine, imine, amide, nitro, carboxylic acid, disulphide, carbonate, isocyanate, carbodiimide, carboalkoxy, carbamate and halogen.

In particular, the substituents $R^6$ and $R^7$ can be identical or different and are each i-propyl, neopentyl, adamantyl, mesityl or 2,6-diisopropylphenyl.

Particularly preferred imidazoline or imidazolidine ligands have the following structures (III-a) to (III-o), where Ph is in each case a phenyl substituent, Bu is any type of butyl substituent, Mes is in each case a 2,4,6-trimethylphenyl substituent and $(iPr)_2Ph$ is in all cases 2,6-diisopropylphenyl.

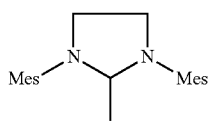

(III-a)

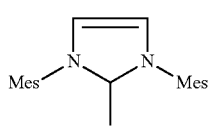

(III-b)

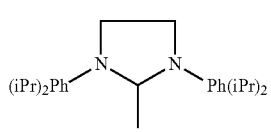

(III-c)

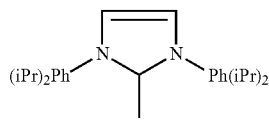

(III-d)

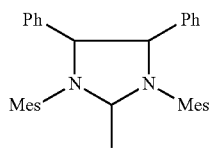

(III-e)

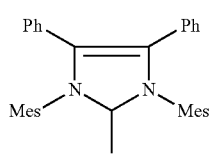

(III-f)

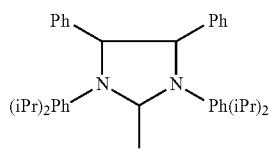

(III-g)

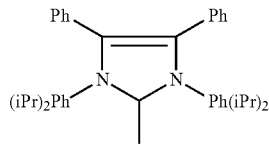

(III-h)

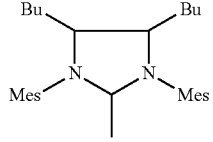

(III-k)

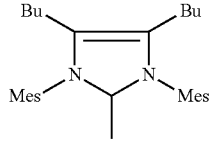

(III-m)

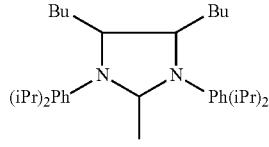

(III-n)

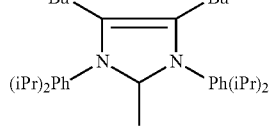

(III-o)

Definition of $L^2$:

In one embodiment of the novel catalysts of the general formula (I)

$R^2$ are identical or different in a respective moiety (Ia*), (Ib*), (Ic*) or (Id*) and represent H, $C_1$-$C_{10}$-alkyl, $C_1$-$C_{14}$-aryl, halide, preferably chloride, or in the alternative two $R^2$ together with the two adjacent carbon atoms to which they are bound in a moiety (Ia*), (Ib*), (Ic*) or (Id*) form a fused-on five- or six-membered saturated or unsaturated ring; and $R^3$ represents preferably $C_1$-$C_{10}$, more preferably $C_1$-$C_4$ alkyl or $C_6$-$C_{14}$ aryl, more preferably phenyl, wherein all aforementioned can be unsubstituted or substituted by one or more substituents, such substituents representing preferably straight-chain or branched $C_1$-$C_{10}$-alkyl, $C_3$-$C_8$-cycloalkyl, $C_1$-$C_{10}$-alkoxy or $C_6$-$C_{24}$-aryl, where these substituents may in turn be substituted by one or more functional groups, preferably functional groups selected from the group consisting of halide, $C_1$-$C_5$-alkyl, $C_1$-$C_5$-alkoxy, phenyl and substituted phenyl.

The ligands pursuant to formulae (Ia*) and (Ib*) may act as monodentate, but in some cases also as bi- or tridentate ligands depending on then structure as well as depending on the other ligands in the complex. The ligands pursuant to formulae (Ic*) and (Id*) may act as bidentate ligands, but in some cases also as tridentate ligands depending on their structure as well as depending on the other ligands in the complex.

Preferably $L^2$ represents a ligand having the structure (Ia*) or (Ib*) in which n is identical or different and represents an integer in the range of from 1 to 10 and D is identical or different and represents $C_1$-$C_{20}$-alkoxy, $C_6$-$C_{24}$-aryloxy or $C_1$-$C_{10}$-thioether, and wherein $R^2$ and $R^3$ have the above mentioned general or preferred meanings.

In a more preferred embodiment $L^2$ represents a ligand of the structure (Ia*) or (Ib*) in which n is identical or different and represents an integer in the range of from 1 to 5, and D is identical or different and represents $C_1$-$C_{10}$-alkoxy or $C_6$-$C_{14}$-aryloxy;

and wherein $R^2$ and $R^3$ have the above mentioned general or preferred meanings.

In a particularly preferred embodiment $L^2$ represents a ligand of the structures (Ia*-1) or (Ib*-2)

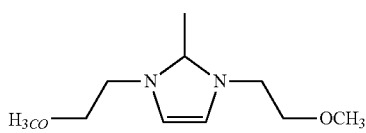

(Ia*-1)

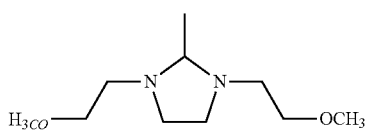

(Ib*-1)

In another preferred embodiment $L^2$ represents a ligand of the structure (Ic*) or (Id*) in which n is identical or different and represents an integer in the range of from 1 to 10, E is identical or different and represents oxygen or sulfur, and $R^3$ is identical or different and represents $C_1$-$C_{20}$-alkyl or $C_6$-$C_{24}$-aryl;

and wherein $R^2$ and $R^3$ have the above mentioned general or preferred meanings, In a more preferred embodiment $L^2$ represents a ligand of the structure (Ic*) or (Id*) in which n is identical or different and represents an integer in the range of from 1 to 5, E is identical or different and represents oxygen or sulfur, and $R^3$ is identical or different and represents $C_1$-$C_{10}$ alkyl or $C_6$-$C_{14}$ aryl;

and wherein $R^2$ and $R^3$ have the above mentioned general or preferred meanings.

In a particularly preferred embodiment $L^2$ represents a ligand of the structure

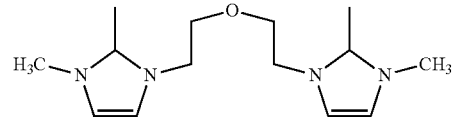

(Ic*-1)

Definition of $R^1$:

In the novel catalyst structures of general formula (I) $R^1$ represents unsubstituted or substituted $C_6$-$C_{14}$-aryl, an N-heterocyclic carbene ligand or $P(R')_3$ with R' being identical or different and representing either substituted or unsubstituted, straight chain or branched $C_1$-$C_{14}$ alkyl, substituted or unsubstituted $C_6$-$C_{24}$ aryl, or substituted or unsubstituted $C_3$-$C_{20}$ cycloalkyl.

Preferably $R^1$ represents unsubstituted $C_6$-$C_{14}$-aryl or $C_6$-$C_{14}$-aryl being substituted with 1, 2, 3, 4, 5 or more substituents selected from the group consisting of F, Cl, Br, I, $NO_2$, and $CH_3$. In very preferred embodiments of the novel catalyst structures of general formula (I) $R^1$ is either an unsubstituted phenyl ring, or a phenyl ring bearing one substituent in p-position being selected from the group consisting of F, Cl, Br, I, $NO_2$, and $CH_3$ or a phenyl ring bearing five substituents being selected from F, Cl, Br, I and mixtures thereof.

Definition of R:

In the novel catalyst structures of general formula (I) R means substituted or unsubstituted, straight chain or branched $C_1$-$C_{14}$-, preferably $C_1$-$C_8$-alkyl, more preferably $C_1$-$C_5$-alkyl. In one preferred embodiment of the novel catalyst structures of the general formula (I) R is either an unsubstituted, straight chain or branched $C_1$-$C_5$-alkyl or a straight chain or branched $C_1$-$C_5$-alkyl, preferably methyl, which is substituted by $C_6$-$C_{14}$-aryl, most preferably substituted by phenyl.

In a preferred embodiment the invention relates to Ruthenium-based complexes according to general formula (I) wherein $X^1$ means halide, more preferably fluoride, chloride, bromide or iodide, phosphate, borate, carboxylate, acetate, trifluoroacetate, trifluoromethylsulfonate or tosylate;

Y is O or S, more preferably S;

$R^1$ represents unsubstituted $C_6$-$C_{14}$-aryl or $C_6$-$C_{14}$-aryl being substituted with 1, 2, 3, 4, 5 or more substituents selected from the group consisting of F, Cl, Br, I, $NO_2$, and $CH_3$;

R represents unsubstituted, straight chain or branched $C_1$-$C_5$-alkyl or a straight chain or branched $C_1$-$C_5$-, more preferably methyl, which is substituted by $C_6$-$C_{14}$-aryl, most preferably substituted by phenyl;

$L^1$ represents an imidazoline or imidazolidine ligand having a structure corresponding to the general formulae (IIa), or (IIb),

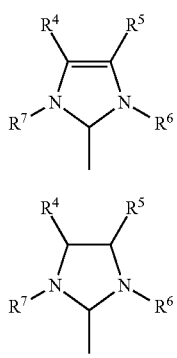

(IIa)

(IIb)

wherein under the proviso that $L^1$ is different from the general formulae (Ia*), (Ib*), (Ic*) and (Id*), $R^4$, $R^5$, $R^6$, $R^7$ are identical or different and are each hydrogen, straight-chain or branched $C_1$-$C_{30}$-alkyl, $C_3$-$C_{20}$-cycloalkyl, $C_2$-$C_{20}$-alkenyl, $C_2$-$C_{20}$-alkynyl, $C_6$-$C_{24}$-aryl, $C_1$-$C_{20}$-carboxylate, $C_1$-$C_{20}$-alkoxy, $C_2$-$C_{20}$-alkenyloxy, $C_2$-$C_{20}$-alkynyloxy, $C_6$-$C_{20}$-aryloxy, $C_2$-$C_{20}$-alkoxycarbonyl, $C_1$-$C_{20}$-alkylthio, $C_6$-$C_{20}$-arylthio, $C_1$-$C_{20}$-alkylsulphonyl, $C_1$-$C_{20}$-alkylsulphonate, $C_6$-$C_{20}$-arylsulphonate or $C_1$-$C_{20}$-alkylsulphinyl or in the alternative $R^6$ and $R^7$ have the above mentioned meanings and at the same time $R^4$ and $R^5$ jointly form a $C_6$-$C_{10}$ cyclic structure together with the two adjacent carbon atoms in the imidazoline or imidazolidine ring; and $L^2$ represents either a ligand of the structure (Ia*) or (Ib*) in which n is identical or different and represents an integer in the range of from 1 to 5, and D is identical or different and represents $C_1$-$C_{10}$-alkoxy or $C_6$-$C_{14}$-aryloxy, or a ligand of the structure (Ic*) or (Id*) in which n is identical or different and represents an integer in the range of from 1 to 5; and E is identical or different and represents oxygen or sulfur; and $R^3$ is identical or different and represents preferably $C_1$-$C_{10}$, more preferably $C_1$-$C_4$ alkyl or $C_6$-$C_{14}$ aryl, more preferably phenyl, wherein all aforementioned can be unsubstituted or substituted by one or more substituents, such substituents representing preferably straight-chain or branched $C_1$-$C_{10}$-alkyl, $C_3$-$C_8$-cycloalkyl, $C_1$-$C_{10}$-alkoxy or $C_6$-$C_{24}$-aryl, where these substituents may in turn be substituted by one or more functional groups, preferably functional groups selected from the group consisting of halide, $C_1$-$C_5$-alkyl, $C_1$-$C_5$-alkoxy, phenyl and substituted phenyl.

with $R^2$ being identical or different in a respective moiety (Ia*), (Ib*), (Ic*) or (Id*) and representing H, $C_1$-$C_{10}$-alkyl, $C_6$-$C_{14}$-aryl, halide, preferably chloride, or in the alternative two $R^2$ together with the two adjacent carbon atoms to which they are bound in a moiety (Ia*), (Ib*), (Ic*) or (Id*) form a fused-on five- or six-membered saturated or unsaturated ring.

In very preferred embodiments the invention relates to complex catalysts having the following formulae (I-1) to (I-8), wherein "Ph" means phenyl, "Me" means methyl and "Mes" means 2,4,5 trimethylphenyl.

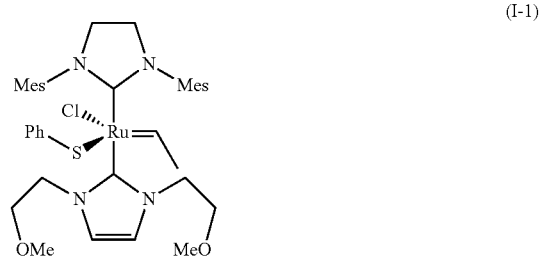

(I-1)

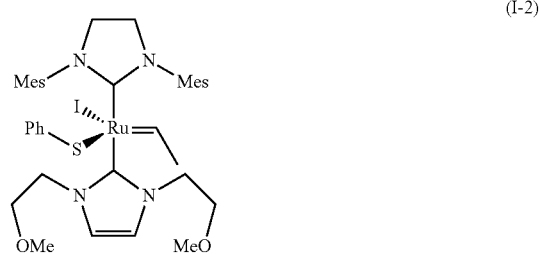

(I-2)

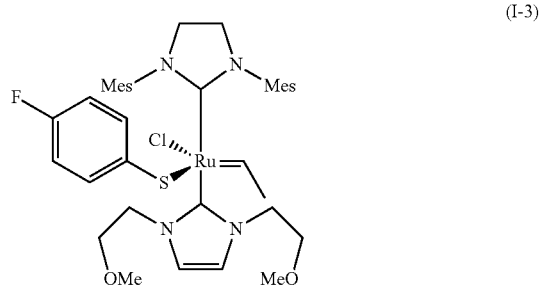

(I-3)

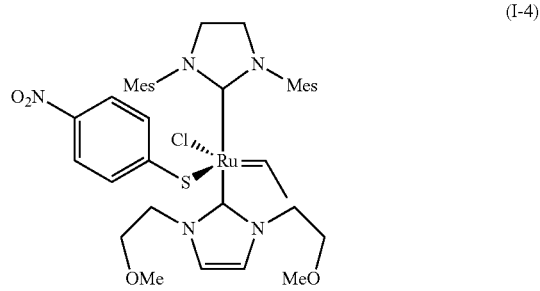

(I-4)

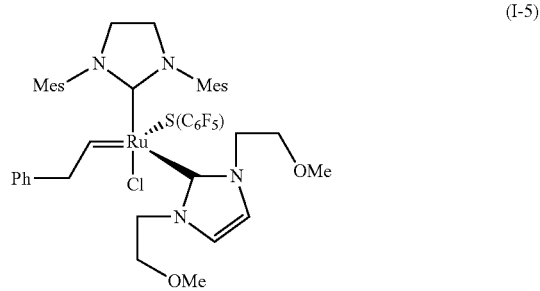

(I-5)

(I-6)

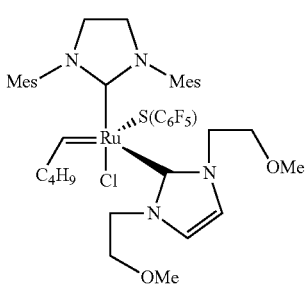

(I-7)

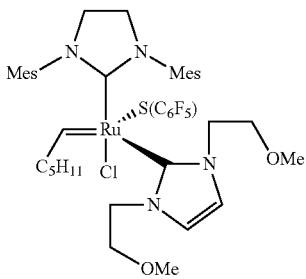

(I-8)

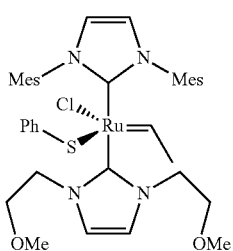

(I-9)

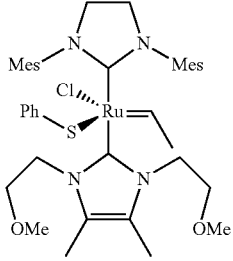

(I-10)

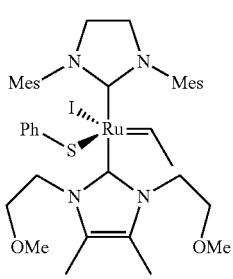

Synthesis of the Complex Catalysts According to General Formula (I)

The above catalyst compounds of general formula (I) can be synthesized by the reaction of $L^1L^2L^3RuHCl$ and the appropriate vinyl sulfide or corresponding ether analogue where insertion into the metal-hydride results in the formation of a metal-alkylidene. Chloride exchange is accomplished by using $(CH_3)_3SiX^2$. The reaction is shown in the following scheme:

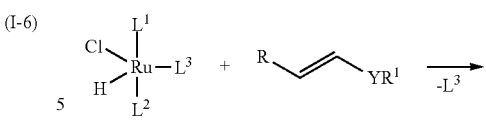

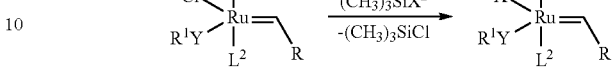

wherein
$L^1, L^2, Y, R^1$ and R have the same meanings as defined above with regard to formula (I) and
$L^3$ represents $P(R')_3$ with R' being identical or different and representing either substituted or unsubstituted, straight chain or branched $C_1$-$C_{14}$ alkyl, substituted or unsubstituted $C_6$-$C_{24}$ aryl, or substituted or unsubstituted $C_3$-$C_{20}$ cycloalkyl, preferably $PPh_3$, $P(p\text{-}Tol)_3$, $P(o\text{-}Tol)_3$, $PPh(CH_3)_2$, $P(p\text{-}FC_6H_4)_3$, $P(p\text{-}CF_3C_6H_4)_3$, $P(C_6H_4\text{—}SO_3Na)_3$, $P(CH_2C_6H_4\text{—}SO_3Na)_3$, $P(isopropyl)_3$, $P(CHCH_3(CH_2CH_3))_3$, $P(cyclopentyl)_3$, $P(cyclohexyl)_3$, $P(neopentyl)_3$ or $P(benzyl)_3$, The present invention therefore relates to a process for preparing the complex catalysts of general formula (I) comprising reacting a compound of general formula (IV)

(IV)

in which
$L^1$ and $L^2$ have the same meanings as defined with regard to formula (I) and
$L^3$ represents $P(R')_3$ with R' being identical or different and representing either substituted or unsubstituted, straight chain or branched $C_1$-$C_{14}$ alkyl, substituted or unsubstituted $C_6$-$C_{24}$ aryl, or substituted or unsubstituted $C_3$-$C_{20}$ cycloalkyl, preferably $PPh_3$, $P(p\text{-}Tol)_3$, $P(o\text{-}Tol)_3$, $PPh(CH_3)_2$, $P(p\text{-}FC_6H_4)_3$, $P(p\text{-}CF_3C_6H_4)_3$, $P(C_6H_4\text{—}SO_3Na)_3$, $P(CH_2C_6H_4\text{—}SO_3Na)_3$, $P(isopropyl)_3$, $P(CHCH_3(CH_2CH_3))_3$, $P(cyclopentyl)_3$, $P(cyclohexyl)_3$, $P(neopentyl)_3$ or $P(benzyl)_3$,
with a compound of general formula (V)

(V)

in which Y and $R^1$ have the same meanings as defined with regard to formula (I),
resulting in a compound of general formula (VI)

(VI)

in which $L^1$, $L^2$, $R^1$, Y and R have the same meanings as defined with regard to formula (I), which is then converted with $$(CH_3)_3SiX^2$$

in which $X^2$ has the same meaning as defined with regard to formula (I) to yield the compound of general formula (I).

The synthesis of the catalyst complexes of general formula (I) according to the process of the present invention can be accomplished in an organic solvent. Preferably dichloromethane, dichloroethane, bromobenzene or chlorobenzene are used. The reaction is typically performed at a temperature in the range of 20 to 50° C., preferably 25° C. to 45° C. The following chloride exchange by $X^2$ is also performed in an organic solvent, preferably in benzene, typically also a temperature in the range of 20 to 50° C., preferably 25° C. to 45° C.

The synthesis of the compound (IV), namely $L^1L^2L^3RuHCl$, can be performed in accordance with the procedure outlined in WO-A-2013/024119.

Such synthesis comprises
a) converting a compound of general formula $L^2AgCl$ selected from the group consisting of compounds (VIIa), (VIIb), (VIIc) and (VIId)

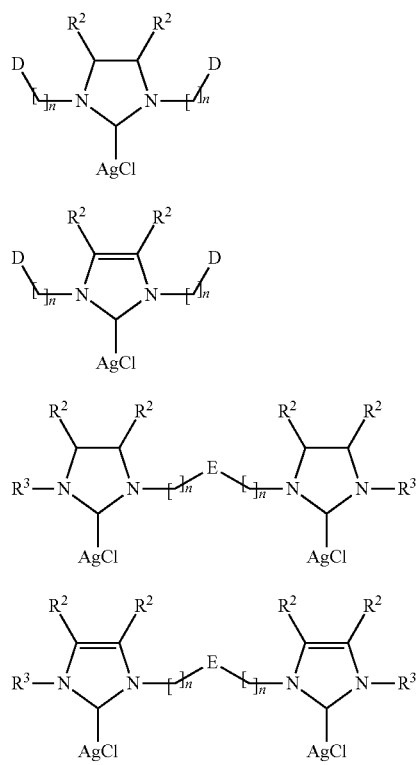

in which formulae (VIIa), (VIIb), (VIIc) and (VIId)
n is identical or different and represents an integer in the range of from 1 to 20,
D is identical or different and represents hydroxy, alkoxy, aryloxy, thiol, thiolate, thioether, selenol, selenoether, amine, phosphine, phosphate, phosphite, arsine, sulfoxide, sulfone, alkyl, phosphinimine, aminophosphine, carbene, selenoxide, imidazoline, imidazolidine, phosphine oxide, phosphine sulfide, phosphine selenide, ketone, ester, pyridyl, substituted pyridyl or any moiety able of acting as a two electron donor,
$R^3$ is identical or different and represents H, alkyl or aryl, and
E is identical or different and represents a divalent moiety able of acting as a two electron donor selected from the group consisting of —O—, —S—, —Se—, —N(R)—, —P(R)—, —As(R)—, —S(=O)—, —PR(=S)—, —PR(=O)—, —C(=O)—, —C(=S)—, 2,6-pyridylene, substituted 2,6-pyridylene and any other divalent moiety able of acting as a two electron donor, and
$R^2$ are identical or different in the respective compounds (VIIa), (VIIb), (VIIc) or (VIId) and represent H, alkyl, aryl, halide, preferably chloride, or in the alternative two $R^2$ together with the two adjacent carbon atoms to which they are bound in the respective compounds (VIIa), (VIIb), (VIIc) or (VIId) form a fused-on five- or six-membered saturated or unsaturated ring,
with a complex of general formula (VIII)

in which
$L^3$ represents $P(R')_3$ with R' being identical or different and representing either substituted or unsubstituted, straight chain or branched $C_1$-$C_{14}$ alkyl, substituted or unsubstituted $C_6$-$C_{24}$ aryl, or substituted or unsubstituted $C_3$-$C_{20}$ cycloalkyl, preferably $PPh_3$, $P(p-Tol)_3$, $P(o-Tol)_3$, $PPh(CH_3)_2$, $P(p-FC_6H_4)_3$, $P(p-CF_3C_6H_4)_3$, $P(C_6H_4-SO_3Na)_3$, $P(CH_2C_6H_4-SO_3Na)_3$, $P(isopropyl)_3$, $P(CHCH_3(CH_2CH_3))_3$, $P(cyclopentyl)_3$, $P(cyclohexyl)_3$, $P(neopentyl)_3$ or $P(benzyl)_3$,
resulting in a complex of general formula (IX)

wherein $L^2$ and $L^3$ have the same meanings as outlined above for general formula (I),
b) converting such complex of general formula (IX) with a compound $L^1$ in which $L^1$ has the same meaning as defined in general formula (I) obtaining a complex of general formula (X)

in which $L^1$, $L^2$, and $L^3$ have the same meanings as outlined above for general formula (I).

The starting compound $L^2AgCl$ can be easily prepared according to processes known to the person skilled in the art and as e.g. disclosed in WO-A-2013/024119.

Metathesis:

The present invention further provides a process of contacting at least one substrate containing C=C double bonds with a novel complex catalyst according to general formula (I) and performing a metathesis reaction. The metathesis reaction can be, for example, a ring-closing metatheses (RCM), a cross-metatheses (CM) or a ring-opening metatheses (ROMP). For this purpose, the substrate or substrates to be subjected to the metathesis is/are brought into contact and reacted with the complex catalyst according to formula (I).

In a preferred embodiment the present process relates to the preparation of nitrile rubbers with a reduced molecular weight $M_w$ by subjecting a starting nitrile rubber to a cross-metathesis reaction in the presence of a complex catalyst according to general formula (I).

Compounds to be Subjected to Metathesis:

Any type of compounds containing at least one C=C double bond can be subjected to a metathesis reaction.

The inventive process can be preferably applied to so-called nitrile rubbers. Nitrile rubbers ("NBR") represent copolymers or terpolymers containing repeating units of at least one conjugated diene, at least one α,β-unsaturated nitrile monomer and, if appropriate, one or more further copolymerizable monomers.

The conjugated diene in such nitrile rubbers can be of any nature. Preference is given to using ($C_4$-$C_6$)-conjugated dienes. Particular preference is given to 1,3-butadiene, isoprene, 2,3-dimethylbutadiene, piperylene or mixtures thereof. In particular, use is preferably made of 1,3-butadiene or isoprene or mixtures thereof. Very particular preference is given to 1,3-butadiene.

As α,β-unsaturated nitrile monomer, it is possible to use any known α,β-unsaturated nitrile, with preference being given to ($C_3$-$C_5$)-α,β-unsaturated nitriles such as acrylonitrile, methacrylonitrile, ethacrylonitrile or mixtures thereof. Particularly preference is given to acrylonitrile.

A particularly preferred nitrile rubber to be subjected to metathesis according to the invention is thus a copolymer of acrylonitrile and 1,3-butadiene.

In addition to the conjugated diene and the α,β-unsaturated nitrile, it is possible to use one or more further copolymerizable monomers known to those skilled in the art, e.g. termonomers containing carboxyl groups, like α,β-unsaturated monocarboxylic acids, their esters or amides, α,β-unsaturated dicarboxylic acids, their monoesters or diesters, or their corresponding anhydrides or amides.

As α,β-unsaturated monocarboxylic acids it is possible to use acrylic acid and methacrylic acid.

It is also possible to employ esters of the α,β-unsaturated monocarboxylic acids, preferably their alkyl esters and alkoxyalkyl esters. Preference is given to the alkyl esters, especially $C_1$-$C_{18}$ alkyl esters, of the α,β-unsaturated monocarboxylic acids, Particular preference is given to alkyl esters, especially $C_1$-$C_{18}$ alkyl esters, of acrylic acid or of methacrylic acid, more particularly methyl acrylate, ethyl acrylate, propyl acrylate, n-butyl acrylate, tert-butyl acrylate, 2-ethylhexyl acrylate, n-dodecyl acrylate, methyl methacrylate, ethyl methacrylates, butyl methacrylate and 2-ethylhexyl methacrylate. Also preferred are alkoxyalkyl esters of the α,β-unsaturated monocarboxylic acids, more preferably alkoxyalkyl esters of acrylic acid or of methacrylic acid, more particular $C_2$-$C_{12}$ alkoxyalkyl esters of acrylic acid or of methacrylic acid, very preferably methoxymethyl acrylate, methoxyethyl(meth)acrylate, ethoxyethyl(meth) acrylate and methoxyethyl(meth)acrylate. Use may also be made of mixtures of alkyl esters, such as those mentioned above, for example, with alkoxyalkyl esters, in the form of those mentioned above, for example. Use may also be made of cyanoalkyl acrylate and cyanoalkyl methacrylates in which the C atom number of the cyanoalkyl group is 2-12, preferably α-cyanoethyl acrylate, β-cyanoethyl acrylate and cyanobutyl methacrylate. Use may also be made of hydroxyalkyl acrylates and hydroxyalkyl methacrylate in which the C atom number of the hydroxyalkyl groups is 1-12, preferably 2-hydroxyethyl acrylate, 2-hydroxyethyl methacrylate and 3-hydroxypropyl acrylate; use may also be made of fluorine-substituted benzyl-group-containing acrylates or methacrylates, preferably fluorobenzyl acrylate, and fluorobenzyl methacrylate. Use may also be made of acrylates and methacrylates containing fluoroalkyl groups, preferably trifluoroethyl acrylate and tetrafluoropropyl methacrylate. Use may also be made of α,β-unsaturated carboxylic esters containing amino groups, such as dimethylaminomethyl acrylate and diethylaminoethyl acrylate.

As copolymerizable monomers it is possible, furthermore, to use α,β-unsaturated dicarboxylic acids, preferably maleic acid, fumaric acid, crotonic acid, itaconic acid, citraconic acid and mesaconic acid.

Use may be made, furthermore, of α,β-unsaturated dicarboxylic anhydrides, preferably maleic anhydride, itaconic anhydride, citraconic anhydride and mesaconic anhydride.

It is possible, furthermore, to use monoesters or diesters of α,β-unsaturated dicarboxylic acids.

These α,β-unsaturated dicarboxylic monoesters or diesters may be, for example, alkyl esters, preferably $C_1$-$C_{10}$ alkyl, more particularly ethyl, n-propyl, isopropyl, n-butyl, tert-butyl, n-pentyl or n-hexyl esters, alkoxyalkyl esters, preferably $C_2$-$C_{12}$ alkoxyalkyl, more preferably $C_3$-$C_8$-alkoxyalkyl, hydroxyalkyl, preferably $C_1$-$C_{12}$ hydroxyalkyl, more preferably $C_2$-$C_8$ hydroxyalkyl, cycloalkyl esters, preferably $C_5$-$C_{12}$ cycloalkyl, more preferably $C_6$-$C_{12}$ cycloalkyl, alkylcycloalkyl esters, preferably $C_6$-$C_{12}$ alkylcycloalkyl, more preferably $C_7$-$C_{10}$ alkylcycloalkyl, aryl esters, preferably $C_6$-$C_{14}$ aryl esters, these esters being monoesters or diesters, and it also being possible, in the case of the diesters, for the esters to be mixed esters.

Particularly preferred alkyl esters of α,β-unsaturated monocarboxylic acids are methyl(meth)acrylate, ethyl (meth)acrylate, propyl(meth)acrylate, n-butyl(meth)acrylate, t-butyl(meth)acrylate, hexyl(meth)acrylate, 2-ethylhexyl(meth)acrylate, octyl(meth)acrylate, 2-propyl-heptyl acrylate and lauryl(meth)acrylate. More particularly, n-butyl acrylate is used.

Particularly preferred alkoxyalkyl esters of the α,β-unsaturated monocarboxylic acids are methoxyethyl(meth) acrylate, ethoxyethyl(meth)acrylate and methoxyethyl (meth)acrylate. More particularly, methoxyethyl acrylate is used.

Particularly preferred hydroxyalkyl esters of the α,β-unsaturated monocarboxylic acids are hydroxyethyl(meth) acrylate, hydroxypropyl(meth)acrylate and hydroxybutyl (meth)acrylate.

Other esters of the α,β-unsaturated monocarboxylic acids that are used are additionally, for example, polyethylene glycol (meth)acrylate, polypropylene glycol (meth)acrylate, glycidyl(meth)acrylate, epoxy(meth)acrylate, N-(2-hydroxyethyl)acrylamides, N-(2-hydroxy-methyl)acrylamides and urethane (meth)acrylate.

Examples of α,β-unsaturated dicarboxylic monoesters encompass maleic acid monoalkyl esters, preferably monomethyl maleate, monoethyl maleate, monopropyl maleate and mono-n-butyl maleate;

maleic acid monocycloalkyl esters, preferably monocyclopentyl maleate, monocyclohexyl maleate and monocycloheptyl maleate;

maleic acid monoalkyl cycloalkyl esters, preferably monomethyl cyclopentyl maleate and monoethyl cyclohexyl maleate;

maleic acid monoaryl esters, preferably monophenyl maleate;

maleic acid monobenzyl esters, preferably monobenzyl maleate;

fumaric acid monoalkyl esters, preferably monomethyl fumarate, monoethyl fumarate, monopropyl fumarate and mono-n-butyl fumarate;

fumaric acid monocycloalkyl esters, preferably monocyclopentyl fumarate, monocyclohexyl fumarate and monocycloheptyl fumarate;

fumaric acid monoalkyl cycloalkyl esters, preferably monomethyl cyclopentyl fumarate and monoethyl cyclohexyl fumarate;

fumaric acid monoaryl esters, preferably monophenyl fumarate;

fumaric acid monobenzyl esters, preferably monobenzyl fumarate;

citraconic acid monoalkyl esters, preferably monomethyl citraconate, monoethyl citraconate, monopropyl citraconate and mono-n-butyl citraconate;

citraconic acid monocycloalkyl esters, preferably monocyclopentyl citraconate, monocyclohexyl citraconate and monocycloheptyl citraconate;

citraconic acid monoalkyl cycloalkyl esters, preferably monomethyl cyclopentyl citraconate and monoethyl cyclohexyl citraconate;

citraconic acid monoaryl esters, preferably monophenyl citraconate;

citraconic acid monobenzyl esters, preferably monobenzyl citraconate;

itaconic acid monoalkyl esters, preferably monomethyl itaconate, monoethyl itaconate, monopropyl itaconate and mono-n-butyl itaconate;

itaconic acid monocycloalkyl esters, preferably monocyclopentyl itaconate, monocyclohexyl itaconate and monocycloheptyl itaconate;

itaconic acid monoalkyl cycloalkyl esters, preferably monomethyl cyclopentyl itaconate and monoethyl cyclohexyl itaconate;

itaconic acid monoaryl esters, preferably monophenyl itaconate;

itaconic acid monobenzyl esters, preferably monobenzyl itaconate.

Mesaconic acid monoalkyl esters, preferably mesaconic acid monoethyl esters;

As α,β-unsaturated dicarboxylic diesters it is possible to use the analogous diesters based on the abovementioned monoester groups, and the ester groups may also be chemically different groups. Preferably the substrate to be metathesized is a nitrile rubber comprising repeating units of at least one conjugated diene, at least one α,β-unsaturated nitrile and, if appropriate, one or more further copolymerizable monomers, preferably a nitrile rubber comprising repeating units of at least one conjugated diene selected from the group consisting of 1,3-butadiene, isoprene, 2,3-dimethylbutadiene, piperylene and mixtures thereof, at least one α,β-unsaturated nitrile selected from the group consisting of acrylonitrile, methacrylonitrile, ethacrylonitrile and mixtures thereof, and optionally of one or more further copolymerizable monomers selected from the group consisting of α,β-unsaturated monocarboxylic, dicarboxylic acids, their esters or amides.

The proportions of conjugated diene and α,β-unsaturated nitrile monomer in the NBR polymers to be used can vary within wide ranges. The proportion of the conjugated diene or the sum of conjugated dimes is usually in the range from 40 to 90% by weight, preferably in the range from 50 to 85% by weight, based on the total polymer. The proportion of the α,β-unsaturated nitrile or the sum of the α,β-unsaturated nitriles is usually from 10 to 60% by weight, preferably from 15 to 50% by weight, based on the total polymer. The proportions of the monomers in each case add up to 100% by weight. The additional monomers can be present in amounts of from 0 to 40% by weight, preferably from 0.1 to 40% by weight, particularly preferably from 1 to 30% by weight, based on the total polymer. In this case, corresponding proportions of the conjugated diene or dienes and/or the α,β-unsaturated nitrile or nitriles are replaced by the proportions of the additional monomers, with the proportions of all monomers in each case adding up to 100% by weight.

The preparation of such nitrile rubbers by polymerization of the abovementioned monomers is adequately known to those skilled in the art and is comprehensively described in the literature.

Nitrile rubbers which can be used for the purposes of the invention are commercially available, e.g. as products marketed under the trademarks Perbunan® and Krynac® by Lanxess Deutschland GmbH.

The nitrile rubbers which can be used for the hydrogenation have a Mooney viscosity (ML 1+4 at 100° C.) in the range from 30 to 70, preferably from 30 to 50. This corresponds to a weight average molecular weight $M_w$ in the range 150 000-500 000, preferably in the range 180 000-400 000. The nitrile rubbers used typically have a polydispersity PDI=$M_w/M_n$ ($M_n$ is the number average molecular weight) in the range of 2.0-6.0 and preferably in the range 2.0-4.0.

Metathesis Reaction Conditions:

The metathetic degradation is usually carried out at a temperature in the range from 10° C. to 150° C., preferably at a temperature in the range from 20° C. to 100° C. The reaction is typically performed under standard pressure.

The metathesis reaction can be carried out in a suitable solvent which does not deactivate the complex catalyst used and also does not adversely affect the reaction in any other way. Preferred solvents encompass, but are not restricted to, dichloromethane, benzene, toluene, methyl ethyl ketone, acetone, tetrahydrofuran, tetrahydropyran, dioxane, cyclohexane and chlorobenzene. The particularly preferred solvent is chlorobenzene. In some case, when the coolefin itself can act as solvent, e.g. in the case of 1-hexene, the addition of a further additional solvent can also be dispensed with.

The amount of complex catalyst of general formula (I) based on the nitrile rubber used depends on the nature and the catalytic activity of the specific complex catalyst. The complex catalyst and the substrate(s) are typically used in a molar ratio of 1:226 to 1:2.5 preferably 1:43 to 1:3 and particularly preferably 1:9 to 1:4.5.

When the complex catalyst according to the invention is used for the metathesis of nitrile rubber, the amount of compound of general formula (I) to the nitrile rubber is typically in the range from 0.005 to 0.25 phr, preferably from 0.00667 to 0.1334 phr, and more preferably from 0.0333 to 0.0667 (phr=parts by weight per 100 parts by weight of the nitrile rubber to be degraded).

The Ruthenium-based complex can be further combined with a Lewis acid. It is a viable embodiment of the present invention to perform the catalytic reactions, in particular the metathesis reactions in the presence of such catalyst system comprising the Ruthenium-based complex and a Lewis acid.

The invention therefore also relates to a catalyst system comprising the Ruthenium-based complex of general formula (I) and at least one Lewis acid, preferably a compound of the general formula (Z)

wherein
$R^8$ are identical and are halogen, more preferably F, Cl, I or Br, unsubstituted or substituted $C_6$-$C_{14}$ aryl, more preferably phenyl or phenyl which is substituted with 1, 2, 3, 4, or 5 substituents selected from the group consisting of F, Cl, and $CF_3$, even more preferably $C_6F_5$, or $C_6$-$C_{14}$ heteroaryl, wherein at least one of the 6 to 14 C-atoms is replaced by one heteroatom, preferably nitrogen or oxygen.

Particularly preferred $R^8$ are identical and have the above general, preferred and more preferred meanings.

Most preferred is the addition of $BCl_3$, $BF_3$, $BI_3$, or $B(C_6F_5)_3$.

In case such compound of general formula (Z) is used, the molar ratio of the compound of general formula (Z) to the complex catalyst of general formula (I) is in the range of 0.5:1 to 15:1, preferably 1:1 to 10:1, more preferably 1:1 to 2:1.

For use in the metathesis of NBR, the compound of the general formula (Z) is typically added to the solution of the complex catalyst.

The NBR metathesis can be carried out in the absence or in the presence of a coolefin. This is preferably a straight-chain or branched $C_2$-$C_{16}$-olefin. Suitable olefins are, for example, ethylene, propylene, isobutene, styrene, 1-hexene and 1-octene. Preference is given to using 1-hexene or 1-octene. If the coolefin is liquid (for example as in the case of 1-hexene), the amount of coolefin is preferably in the range 0.2-20% by weight based on the NBR used. If the coolefin is a gas, for example as in the case of ethylene, the amount of coolefin is preferably selected so that a pressure in the range $1 \times 10^5$ Pa-$1 \times 10^7$ Pa, preferably a pressure in the range from $5.2 \times 10^5$ Pa to $4 \times 10^6$ Pa, is established in the reaction vessel at room temperature.

The concentration of the nitrile rubber used in the reaction mixture of the metathesis is not critical, but it naturally has to be noted that the reaction should not be adversely affected by an excessively high viscosity of the reaction mixture and the mixing problems associated therewith. The concentration of the NBR in the reaction mixture is preferably in the range from 1 to 25% by weight, particularly preferably in the range from 5 to 20% by weight, based on the total reaction mixture.

The reaction time depends on a number of factors, for example on the type of NBR, on the type of catalyst, on the catalyst concentration employed and on the reaction temperature. The reaction is typically complete within five hours under normal conditions. The progress of the metathesis can be monitored by standard analytical methods, e.g. by GPC measurements or by determination of the viscosity.

EXAMPLES

I Synthesis of Complexes

Phenyl vinyl sulfide was used as purchased and all other vinyl sulfides were synthesized according to literature procedures:

Synthesis of p-Fluorophenyl Vinyl Sulfide

The synthesis was performed in accordance with *Can. J. Chem.* 1977, 55, 548-551.

Synthesis of p-Nitrophenyl Vinyl Sulfide

The synthesis was performed in accordance with *J. Org. Chem.* 1980, 45, 1046-1053.

Synthesis of Phenyl Vinyl Ether

The synthesis was performed in accordance with *J. Mol. Catal. A: Chem* 2005, 226, 141-147.

Synthesis of $(C_6F_5)SCHCH(C_4H_9)$ Via Water Promoted Regioselective Hydrothiolation of 1-Hexyne The synthesis was performed in accordance with *Can. J. Chem.* 2009, 87, 1605-1609 as follows: A mixture of 1-hexyne (0.86 mL, 7.48 mmol) and pentafluorothiophenol (1.00 mL, 7.50 mmol) was stirred in 6 mL of $H_2O$ at room temperature for 4 hours. The reaction mixture was extracted with $Et_2O$ (3×20 mL) and the ether extract was dried over $MgSO_4$. Solvent removal in vacuo gave a mixture of the (E)- and (Z)-isomers as a clear colourless liquid (1.92 g, 91%).
$^1H$ NMR (400 MHz, $C_6D_6$): Isomer 1: δ 5.80-5.74 (m, 2H, $(C_6F_5)SCHCH(C_4H_9)$), 1.81 (m, 2H, $(C_6F_5)SCHCH(C_4H_9)$), 1.13 (m, 4H, $(C_6F_5)SCHCH(C_4H_9)$), 0.79 (m, 3H, $(C_6F_5)SCHCH(C_4H_9)$). Isomer 2: δ 5.69 (d, $^3J_{HH}$=9 Hz, 1H, $(C_6F_5)SCHCH(C_4H_9)$), 5.55 (dt, $^3J_{HH}$=9 Hz, $^3J_{HH}$=7 Hz, 1H, $(C_6F_5)SCHCH(C_4H_9)$), 2.19 (m, 2H, $(C_6F_5)SCHCH(C_4H_9)$), 1.26 (m, 4H, $(C_6F_5)SCHCH(C_4H_9)$), 0.84 (m, 3H, $(C_6F_5)SCHCH(C_4H_9)$).
$^{19}F\{^1H\}$ NMR (178 MHz, $C_6D_6$): δ−133.94 (m, 2F, o-F), −154.03 (t, $^3J_{FF}$=21 Hz, 1F, p-F), −161.80 (m, 2F, m-F).
$^{13}C\{^1H\}$ NMR (101 MHz, $C_6D_6$): δ 146.9 (dm, $^1J_{CF}$=247 Hz, $C_6F_5$), 141.2 (dm, $^1J_{CF}$=252 Hz, $C_6F_5$), 137.6 (dm, $^1J_{CF}$=252 Hz, $C_6F_5$). Isomer 1: 134.1 $((C_6F_5)SCHCH(C_4H_9))$, 120.5 $((C_6F_5)SCHCH(C_4H_9))$, 31.0 $((C_6F_5)SCHCH(C_4H_9))$, 28.6 $((C_6F_5)SCHCH(C_4H_9))$, 22.3 $((C_6F_5)SCHCH(C_4H_9))$, 13.7 $((C_6F_5)SCHCH(C_4H_9))$. Isomer 2: 138.0 $((C_6F_5)SCHCH(C_4H_9))$, 118.0 $((C_6F_5)SCHCH(C_4H_9))$, 32.5 $((C_6F_5)SCHCH(C_4H_9))$, 30.9 $((C_6F_5)SCHCH(C_4H_9))$, 22.2 $((C_6F_5)SCHCH(C_4H_9))$, 13.7 $((C_6F_5)SCHCH(C_4H_9))$.

Synthesis of $(C_6F_5)SCHCH(C_3H_7)$ Via Water Promoted Regioselective Hydrothiolation of 1-Pentyne The synthesis was performed in accordance with *Can. J. Chem.* 2009, 87, 1605-1609 as follows: A mixture of 1-pentyne (0.74 mL, 7.50 mmol) and pentafluorothiophenol (1.00 mL, 7.50 mmol) was stirred in 6 mL of $H_2O$ at room temperature for 4 hours. The reaction mixture was extracted with $Et_2O$ (3×20 mL) and the ether extract was dried over $MgSO_4$. Solvent removal in vacuo gave a mixture of the (E)- and (Z)-isomers as a clear colourless liquid (1.61 g, 80%).
$^1H$ NMR (400 MHz, $C_6D_6$): Isomer 1: δ 5.91-5.84 (m, 2H, $(C_6F_5)SCHCH(C_3H_7)$), 2.00 (m, 2H, $(C_6F_5)SCHCH(C_3H_7)$), 1.34 (m, 2H, $(C_6F_5)SCHCH(C_3H_7)$), 0.82 (m, 3H, $(C_6F_5)SCHCH(C_3H_7)$). Isomer 2: δ 5.84 (d, $^3J_{HH}$=9 Hz, 1H, $(C_6F_5)SCHCH(C_3H_7)$), 5.76 (m, 1H, $(C_6F_5)SCHCH ($C_3H_7$)), 2.21 (m, 2H, ($C_6F_5$)SCHCH($C_3H_7$)), 1.41 (m, 2H, ($C_6F_5$)SCHCH($C_3H_7$)), 0.89 (m, 3H, ($C_6F_5$)SCHCH($C_3H_7$)).

$^{19}F\{^1H\}$ NMR (178 MHz, $C_6D_6$): δ −132.99 (m, 2F, o-F), −153.05 (t, $^3J_{FF}$=21 Hz, 1F p-F), −161.00 (m, 2F, m-F).

$^{13}C\{^1H\}$ NMR (101 MHz, $C_6D_6$); δ 147.2 (dm, $^1F_{CF}$=247 Hz, $C_6F_5$), 141.2 (dm, $^1J_{CF}$=252 Hz, $C_6F_5$), 137.7 (dm, $^1J_{CF}$=252 Hz, $C_6F_5$). Isomer 1: 134.2 (($C_6F_5$)SCHCH($C_3H_7$)), 120.8 (($C_6F_5$)SCHCH($C_3H_7$)), 34.7 (($C_6F_5$)SCHCH($C_3H_7$)), 22.1 (($C_6F_5$)SCHCH($C_3H_7$)), 13.4 (($C_6F_5$)SCHCH($C_3H_7$). Isomer 2: 137.7 (($C_6F_5$)SCHCH($C_3H_7$)), 118.7 (($C_6F_5$)SCHCH($C_3H_7$)), 35.0 (($C_6F_5$)SCHCH($C_3H_7$)), 21.9 (($C_6F_5$)SCHCH($C_3H_7$)), 13.3 (($C_6F_5$)SCHCH($C_3H_7$)).

Complex (1) was synthesized in accordance with Example A3 of WO-A-2013/024119.

Complex (3) was synthesized in analogy to Example A3 of WO-A-2013/024119.

Complex (6) was synthesized in accordance with Example A4 of WO-A-2013/024119

"IMes-$Cl_2$" means:

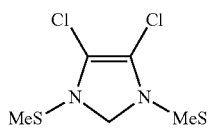

"IMes" means:

"SIMes" means:

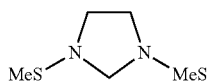

I.1 Synthesis of Complex (2)

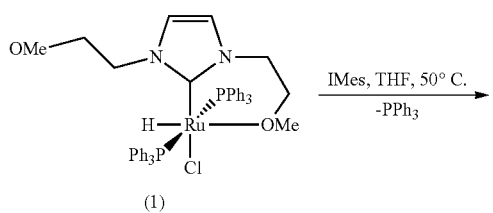

(1)

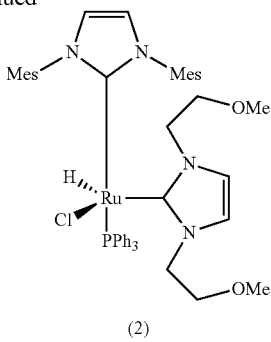

(2)

IMes (0.105 g, 0.354 mmol) in 5 mL THF was added to a solution of Complex (1) (0.150 g, 0.177 mmol) in 5 mL of THF and the mixture was heated at 60° C. for 24 h. All volatiles were removed in vacuum. The product was extracted with toluene (10 mL) and filtered through celite. The solution was concentrated to 2 mL and pentane (15 mL) was added to the red solution to precipitate the product. Complex (2) was obtained as red solid on a frit and dried under vacuum (0.114 g, 73%). X-ray quality crystals were grown from toluene/pentane at 25° C.

$^1H$ NMR (400 MHz, $C_6D_6$): δ 7.54 (t, $^3J_{HH}$=8 Hz, 6H, $PPh_3$), 7.39 (m, 1H, IMes-CH), 7.04 (m, 2H, Mes-CH), 6.99-6.90 (m, 13H, $PPh_3$+IMes-CH+Mes-CH+OCO—CH), 6.66 (d, $^3J_{HH}$=2 Hz, OCO—CH), 4.68 (dd, $^2J_{HH}$=15 Hz, $^3J_{HH}$=3 Hz, 1H, OCO—$CH_2$), 3.90 (m, 1H, OCO—$CH_2$), 2.92-2.10 (m, 30H, OCO—$CH_3$+OCO—$CH_2$+Mes-$CH_3$), −28.12 (d, $^2J_{PH}$=26 Hz, 1H, Ru—H).

$^{31}P\{^1H\}$ NMR (161 MHz, $C_6D_6$): δ 43.9 (s, $PPh_3$).

$^{13}C\{^1H\}$ NMR (101 MHz, $C_6D_6$): δ 141.3 (d, $^1J_{PC}$=30 Hz, $C_{ipso}$, $PPh_3$), 137.3 ($C_{ipso}$), 134.9 (d, $^2J_{PC}$=11 Hz, o-C, $PPh_3$), 134.3 (IMes-CH), 134.1 (IMes-CH), 128.9 (d, $^4J_{PC}$=2 Hz, p-C, $PPh_3$), 128.8 (Mes-CH), 128.4 (IMes-CH), 127.6 (d, $^3J_{PC}$=8 Hz, m-C, $PPh_3$), 119.9 (OCO—CH), 118.4 (OCO—CH), 72.6 (OCO—$CH_2$), 71.4 (OCO—$CH_2$), 58.2 (OCO—$CH_3$), 57.9 (OCO—$CH_3$), 48.0 (OCO—$CH_2$), 47.5 (OCO—$CH_2$), 21.3 (Mes-$CH_3$).

I.2 Synthesis of Complex (4)

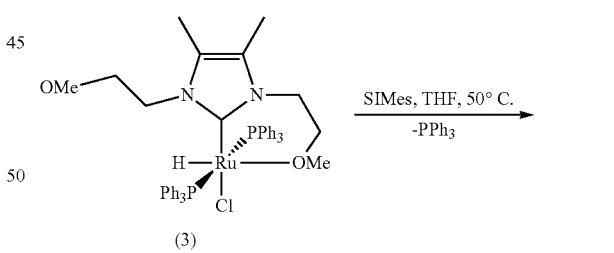

(3)

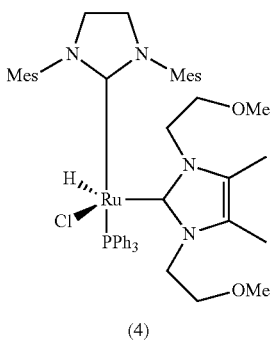

(4)

SIMes (0.070 g, 0.228 mmol) in 5 mL THF was added to a solution of Complex (3) (0.100 g, 0.114 mmol) in 5 mL of THF and the mixture was heated at 50° C. for 24 h. All volatiles were removed in vacuum. The product was extracted with toluene (10 mL) and filtered through celite. The solution was concentrated to 2 mL and pentane (15 mL) was added to the red solution to precipitate the product. Complex (4) was collected as red solid on a frit and dried under vacuum (0.076 g, 73%).

$^1$H NMR (400 MHz, C$_6$D$_6$): δ 7.52 (t, $^3J_{HH}$=8 Hz, 6H, PPh$_3$), 6.94 (m, 11H, PPh$_3$+Mes-CH), 6.82 (s, 1H, Mes-CH), 6.51 (s, 1H, Mes-CH), 4.43 (dt, $^2J_{HH}$=16 Hz, $^3J_{HH}$=4 Hz, 1H, OCO—CH$_2$), 3.60 (m, 1H, OCO—CH$_2$), 3.39-3.16 (m, 8H, OCO—CH$_2$+SIMes-CH$_2$), 2.99 (s, 6H, OCO—CH$_3$+Mes-CH$_3$), 2.83 (br s, 5H, Mes-CH$_3$+OCO—CH$_2$), 2.64 (s, 6H, OC—CH$_3$+Mes-CH$_3$), 2.33 (s, 3H, Mes-CH$_3$), 2.13 (s, 3H, Mes-CH$_3$), 1.92 (s, 3H, OCO-4,5-H$_3$), 1.83 (s, 3H, OCO-4,5-CH$_3$), 1.59 (s, 3H, Mes-CH$_3$), −27.43 (d, $^2J_{PH}$=27 Hz, 1H, Ru—H).

$^{31}$P{$^1$H} NMR (161 MHz, C$_6$D$_6$): δ 36.5 (s, PPh$_3$).

$^{13}$C{$^1$H} NMR (101 MHz, C$_6$D$_6$): δ 141.2 (d, $^1J_{PC}$=29 Hz, C$_{ipso}$, PPh$_3$), 139.7 (C$_{ipso}$), 135.0 (d, $^2J_{PC}$=11 Hz, o-C, PPh$_3$), 128.9 (d, $^4J_{PC}$=2 Hz, p-C, PPh$_3$), 128.6 (C$_{ipso}$), 127.5 (d, $^3J_{PC}$=8 Hz, m-C, PPh$_3$), 125.7 (C$_{ipso}$), 124.5 (OCO-4,5-C$_{ipso}$), 122.2 (OCO-4,5-C$_{ipso}$), 72.9 (OCO—CH$_2$), 71.0 (OCO—CH$_2$), 58.4 (OCO—CH$_3$), 57.8 (OCO—CH$_3$), 51.5 (SIMes-CH$_2$), 50.8 (SIMes-CH$_2$), 46.5 (OCO—CH$_2$), 45.9 (OCO—CH$_2$), 21.4 (Mes-CH$_3$), 21.2 (Mes-CH$_3$), 21.0 (Mes-CH$_3$), 20.9 (Mes-CH$_3$), 19.6 (Mes-CH$_3$), 18.3 (Mes-CH$_3$), 10.3 (OCO-4,5-CH$_3$), 9.8 (OCO-4,5-CH$_3$).

I.3 Synthesis of Complex (5)

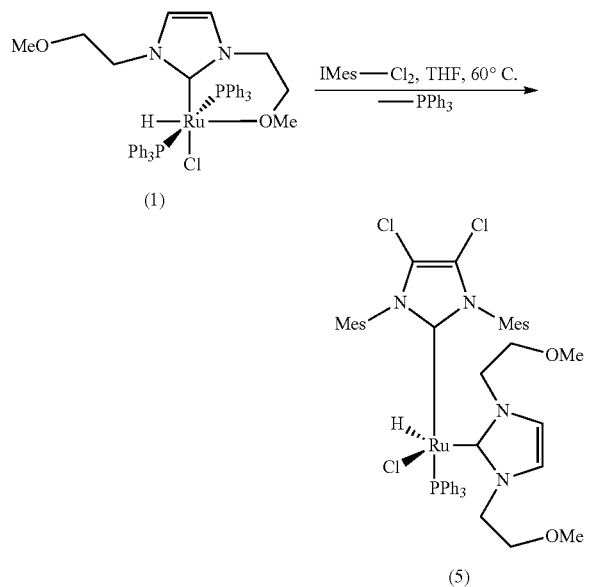

IMes-Cl$_2$ (0.174 g, 0.472 mmol) in 5 mL THF was added to a solution of Complex (1) (0.200 g, 0.236 mmol) in 5 mL of THF and the mixture was heated at 60° C. for 48 h. All volatiles were removed in vacuum. The product was extracted with toluene (10 mL) and filtered through celite. The solution was concentrated to 2 mL and pentane (15 mL) was added to the red solution to precipitate the product. The red solid was collected on a frit and dried under vacuum (0.147 g, 65%). X-ray quality crystals were grown from toluene/pentane at 25° C.

$^1$H NMR (500 MHz, C$_6$D$_6$): δ 7.48 (t, $^3J_{HH}$=8 Hz, 6H, PPh$_3$), 6.96 (m, 5H, PPh$_3$+Mes-CH), 6.90 (m, 8H, PPh$_3$+Mes-CH), 6.68 (br s, 1H, OCO—CH), 6.67 (d, $^3J_{HH}$=2 Hz, 1H, OCO—CH), 4.61 (ddd, $^2J_{HH}$=15 Hz, $^3J_{HH}$=4 Hz, $^3J_{HH}$=2 Hz, 1H, OCO—CH$_2$), 3.88 (m, 1H, OCO—CH$_2$), 2.91 (s, 3H, OCO—CH$_3$), 2.87 (m, 1H, OCO—CH$_2$), 2.81-2.57 (m, 13H, OCO—CH$_3$+Mes-CH$_3$+OCO—CH$_2$) 2.36-2.15 (m, 10H, OCO—CH$_2$+Mes-CH$_3$), 2.05 (br s, 3H, Mes-CH$_3$), −28.11 (d, $^2J_{PH}$=25 Hz, 1H, Ru—H).

$^{31}$P{$^1$H} NMR (161 MHz, C$_6$D$_6$): δ 43.2 (s, PPh$_3$).

$^{13}$C{$^1$H} NMR (101 MHz, C$_6$D$_6$, partial): δ 140.7 (d, $^1J_{PC}$=31 Hz, C$_{ipso}$, PPh$_3$), 134.9 (d, $^2J_{PC}$=11 Hz, o-C, PPh$_3$), 129.4 (br s, C$_{ipso}$) 128.3 (Mes-CH), 128.2 (d, $^4J_{PC}$=2 Hz, p-C, PPh$_3$), 127.6 (d, $^3J_{PC}$=8 Hz, m-C, PPh$_3$), 120.0 (OCO—CH), 118.8 (OCO—CH), 72.4 (OCO—CH$_2$), 71.3 (OCO—CH$_2$), 58.2 (OCO—CH$_3$), 57.9 (OCO—CH$_3$), 48.1 (OCO—CH$_2$), 47.4 (OCO—CH$_2$), 21.3 (br s, Mes-CH$_3$), 18.2 (br s, Mes-CH$_3$).

I.4 Synthesis of Complex (I-1)

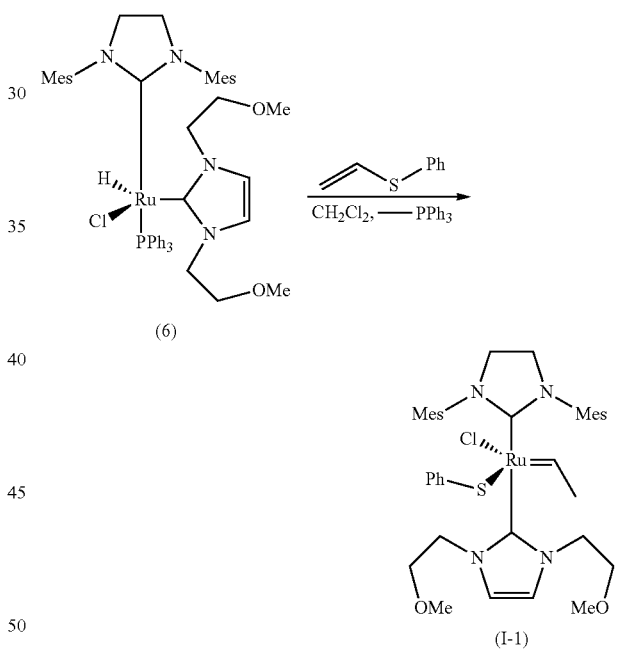

Phenyl vinyl sulfide (16.7 μL, 0.128 mmol) was added to a solution of Complex (6) (0.100 g, 0.112 mmol) in 5 mL CH$_2$Cl$_2$ at room temperature. The solution was then stirred for 5 hours before the solvent was concentrated to 0.5 mL and 15 mL of pentane was added and the resulting mixture was filtered over a pad of celite. The pentane was then removed in vacuo and the resulting residue was layered with 10 mL of pentane and left standing overnight. The free triphenylphosphine is taken up into the pentane layer yielding a red solid (0.079 g, 92%). X-ray quality crystals were grown by slow evaporation of a hexane solution.

$^1$H NMR (400 MHz, CD$_2$Cl$_2$): δ 18.29 (br s, 1H, Ru═CH), 7.01 (s, 2H, Mes-CH), 6.96 (s, 1H, Mes-CH), 6.94 (s, 1H, Mes-CH), 6.85 (s, 1H, OCO—CH), 6.69 (br s, 1H, OCO—CH), 6.60 (m, 3H, S(C$_6$H$_5$)), 6.56 (m, 2H,

S($C_6H_5$)), 3.93 (m, 4H, Mes-$CH_2$), 3.32 (br s, 4H, OCO—$CH_2$), 3.19 (br s, 4H, OCO—$CH_2$+OCO—$CH_3$), 3.16 (s, 3H, OCO—$CH_3$), 3.06 (br s, 2H, OCO—$CH_2$), 2.74 (s, 3H, Mes-$CH_3$), 2.62 (s, 3H, Mes-$CH_3$), 2.50 (s, 3H, Mes-$CH_3$), 2.42 (s, 3H, Mes-$CH_3$), 2.35 (s, 3H, Mes-$CH_3$), 2.31 (s, 3H, Mes-$CH_3$), 1.63 (d, $^3J_{HH}$=5 Hz, 3H, Ru=CH$CH_3$).

$^{13}C\{^1H\}$ NMR (101 MHz, $CD_2Cl_2$): δ 313.7 (Ru=CH$CH_3$), 188.8 (NCN), 151.2 (NCN), 139.9 ($C_{ipso}$), 139.03 ($C_{ipso}$), 138.3 (S($C_6H_5$)), 135.5 ($C_{ipso}$), 137.9 (S($C_6H_5$)), 130.0 (Mes-CH), 129.9 (Mes-CH), 129.7 (Mes-CH), 129.6 (Mes-CH), 126.9 (S($C_6H_5$)), 121.6 (OCO—CH), 121.2 (OCO—CH), 72.2 (OCO—$CH_2$), 58.7 (OCO—$CH_3$), 58.6 (OCO—$CH_3$), 51.8 (SIMes-CM), 51.7 (SIMes-$CH_2$), 49.1 (OCO—$CH_2$), 48.7 (Ru=CH$CH_3$), 21.2 (Mes-$CH_3$), 20.3 (Mes-$CH_3$), 19.0 (Mes-$CH_3$), 18.8 (Mes-$CH_3$).

I.5 Synthesis of Complex (I-2)

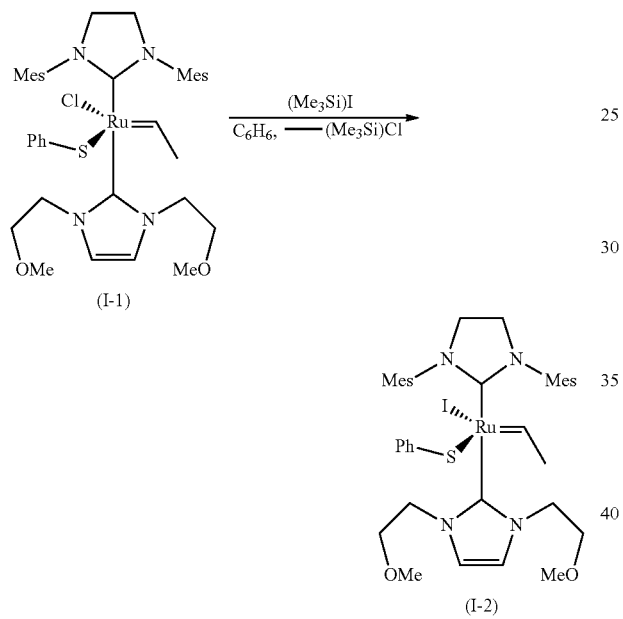

(I-1)

(I-2)

Trimethylsilyl iodide (10.0 μL, 0.071 mmol) was added to a solution of Complex (I-1) (0.050 g, 0.065 mmol) in 2 mL $C_6H_6$ at room temperature. The solution was then stirred for one hour before the solvent was removed and the residue washed with pentane. The pentane was then decanted to yield Complex (I-2) as a red solid (0.048 g, 87%). X-ray quality crystals were grown from benzene/pentane at 25° C.

$^1$H NMR (400 MHz, $C_6D_6$): δ 18.82 (br s, 1H, Ru=CH), 7.09 (m, 2H, S($C_6H_5$)), 6.90 (d, $^3J_{HH}$=2 Hz, 1H, OCO—CH), 6.84 (s, 1H, Mes-CH), 6.82 (s, 1H, Mes-CH), 6.78 (m, 5H, Mes-CH+S($C_6H_5$)), 6.57 (br s, 1H, OCO—CH), 3.44 (m, 4H, SIMes-$CH_2$), 3.30 (m, 4H, OCO—$CH_2$), 3.19-2.99 (m, 4H, OCO—$CH_2$), 2.95 (s, 3H, OCO—$CH_3$), 2.89 (s, 3H, Mes-CH), 2.85 (s, 3H, Mes-$CH_3$), 2.81 (s, 3H, OCO—$CH_3$), 2.75 (s, 3H, Mes-$CH_3$), 2.71 (s, 3H, Mes-$CH_3$), 2.14 (s, 3H, Mes-$CH_3$), 2.13 (s, 3H, Mes-$CH_3$), 2.00 (d, $^3J_{HH}$=6 Hz, 3H, Ru=CH$CH_3$).

$^{13}C\{^1H\}$ NMR (101 MHz, $C_6D_6$): δ 313.7 (Ru=CH$CH_3$), 188.5 (NCN), 151.1 (NCN), 139.8 ($C_{ipso}$), 139.6 ($C_{ipso}$), 138.4 ($C_{ipso}$), 138.3 ($C_{ipso}$), 138.3 ($C_{ipso}$), 137.9 (S($C_6H_5$)), 133.5 (S($C_6H_5$)), 130.2 (Mes-CH), 129.9 (Mes-CH), 129.7 (Mes-CH), 127.2 (S($C_6H_5$)), 122.1 (OCO—CH), 121.0 (OCO—CH), 72.5 (OCO—$CH_2$), 71.7 (OCO—$CH_2$), 58.3 (OCO—$CH_3$), 58.2 (OCO—$CH_3$), 51.6 (SIMes-$CH_2$), 51.5 (SIMes-$CH_2$), 49.3 (Ru=CH$CH_3$), 49.0 (OCO—$CH_2$), 23.2 (Mes-$CH_3$), 21.3 (Mes-$CH_3$), 21.1 (Mes-$CH_3$), 20.9 (Mes-$CH_3$), 20.7 (Mes-$CH_3$), 19.6 (Mes-$CH_3$).

I.6 Synthesis of Complex (I-3)

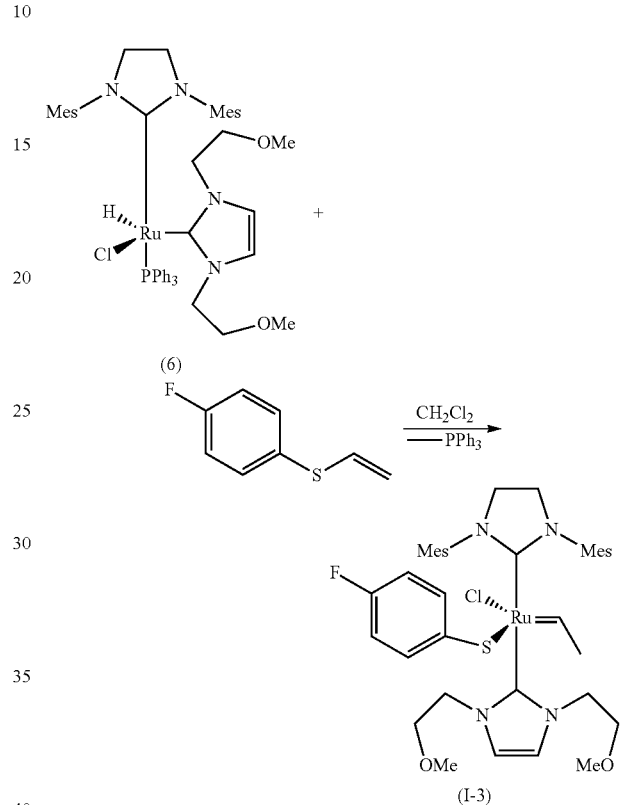

(6)

(I-3)

4-Fluorophenyl vinyl sulfide (0.017 g, 0.224 mmol) was added to a solution of Complex (6) (0.100 g, 0.112 mmol) in 5 mL $CH_2Cl_2$ at room temperature. The solution was then stirred for 4 hours before the solvent was concentrated to 0.5 mL and 15 mL of pentane was added and the resulting mixture was filtered over a pad of celite. The pentane was then removed in vacuo and the resulting residue was layered with 10 mL of pentane and left standing overnight. The free triphenylphosphine is taken up into the pentane layer yielding Complex (I-3) as a red solid (0.070 g, 80%). X-ray quality crystals were grown from benzene/pentane at 25° C.

$^1$H NMR (400 MHz, $CD_2Cl_2$): δ 18.34 (br s, 1H, Ru=CH), 7.01 (s, 2H, Mes-CH), 6.96 (s, 1H, Mes-CH), 6.93 (s, 1H, Mes-CH), 6.86 (d, $^3J_{HH}$=2 Hz, 1H, OCO—CH), 6.68 (br s, 1H, OCO—CH), 6.51 (m, 2H, p-F—$C_6H_5$), 6.34 (app t, $^3J_{HH}$=9 Hz, 2H, p-F—$C_6H_5$), 3.92 (m, 4H, SIMes-$CH_2$), 3.44-3.26 (br s, 4H, OCO—$CH_2$), 3.23 (br s, 3H, OCO—$CH_3$), 3.16 (s, 3H, OCO—$CH_3$), 3.13-3.00 (br s, 4H, OCO—$CH_2$), 2.74 (s, 3H, Mes-$CH_3$), 2.61 (s, 3H, Mes-$CH_3$), 2.48 (s, 3H, Mes-$CH_3$), 2.40 (s, 3H, Mes-$CH_3$), 2.36 (s, 3H, Mes-$CH_3$), 2.31 (s, 3H, Mes-$CH_3$), 1.63 (d, $^3J_{HH}$=5 Hz, Ru=CH$CH_3$). $^{19}F\{^1H\}$ NMR (178 MHz, $CD_2Cl_2$); δ−124.49 (br s).

$^{19}F\{^1H\}$ NMR (178 MHz, $CD_2Cl_2$): δ−124.49 (br s).

$^{13}C\{^1H\}$ NMR (101 MHz, $CD_2Cl_2$): δ 313.5 (Ru=CH$CH_3$), 223.9 (NCH), 188.8 (NCH), 159.7 (d, $^1J_{FF}$=239 Hz, S(C$_6$H$_4$F)), 147.0 (d, $^4J_{FC}$=3 Hz, S(C$_6$H$_4$F)), 140.5 (C$_{ipso}$), 139.9 (C$_{ipso}$), 138.6 (C$_{ipso}$), 138.5 (C$_{ipso}$), 138.1 (C$_{ipso}$), 137.9 (C$_{ipso}$), 137.8 (C$_{ipso}$), 135.6 (C$_{ipso}$), 133.9 (br d, $^3J_{FC}$=7 Hz, S(C$_6$H$_4$F)), 129.8 (Mes-CH), 129.6 (Mes-CH), 121.7 (OCO—CH), 121.1 (OCO—CH), 113.7 (d, $^2J_{FC}$=21 Hz, S(C$_6$H$_4$F)), 73.6 (OCO—CH$_2$), 72.2 (OCO—CH$_2$), 58.4 (OCO—CH$_3$), 58.2 (OCO—CH$_3$), 51.3 (SIMes-CH$_2$), 51.1 (SIMes-CH$_2$), 49.7 (OCO—CH$_2$), 48.9 (OCO—CH$_2$), 46.8 (Ru=CHCH$_3$), 21.1 (Mes-CH$_3$), 21.0 (Mes-CH$_3$), 20.7 (Mes-CH$_3$), 20.5 (Mes-CH$_3$), 19.3 (Mes-CH$_3$), 19.2 (Mes-CH$_3$).

I.7 Synthesis of Complex (I-4)

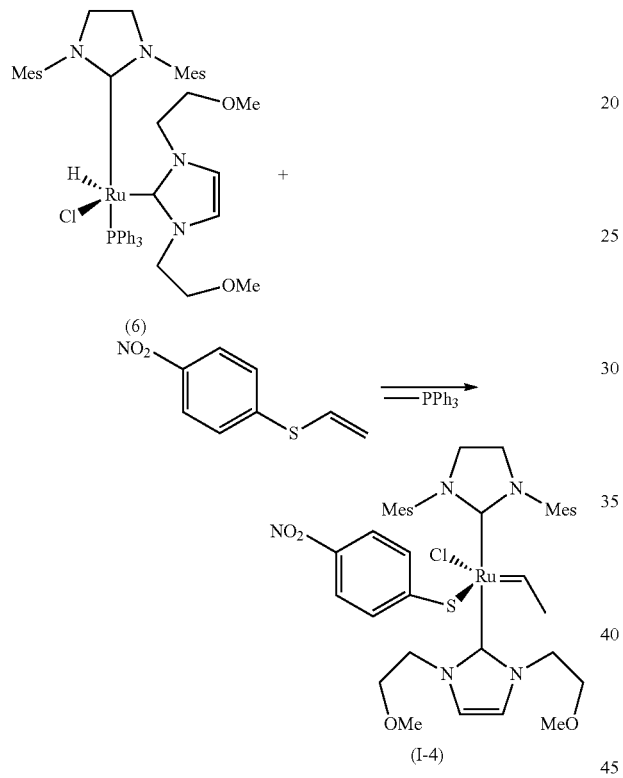

(I-4)

4-Nitrophenyl vinyl sulfide (0.041 g, 0.224 mmol) was added to a solution of Complex (6) (0.100 g, 0.112 mmol) in 5 mL C$_2$H$_4$Cl$_2$ at room temperature. The solution was then stirred for 4 hours before the solvent was concentrated to 0.5 mL and 15 mL of pentane was added and the resulting mixture was filtered over a pad of celite. The pentane was then removed in vacuo and the resulting residue was layered with 10 mL, of pentane and left standing overnight. The free triphenylphosphine is taken up into the pentane layer yielding Complex (I-4) as a purple solid (0.068 g, 75%).

$^1$H NMR (400 MHz, C$_6$D$_6$): δ 18.42 (q, $^3J_{HH}$=6 Hz, 1H, Ru=CH), 7.71 (d, $^3J_{HH}$=9 Hz, 2H, p-NO$_2$(C$_6$H$_4$)), 6.75 (m, 7H, p-NO$_2$(C$_6$H$_4$)+Mes-CH+OCO—CH), 6.49 (s, 1H, OCO—CH), 3.44 (m, 3H, OCO—CH$_2$), 3.32-3.21 (m, 4H, SIMes-CH$_2$), 3.13-2.94 (m, 3H, OCO—CH$_2$), 2.86 (s, 3H, OCO—CH$_3$), 2.76 (s, 5H, OCO—CH$_2$+Mes-CH$_3$), 2.73 (s, 3H, OCO—CH$_3$), 2.64 (s, 6H, 2×Mes-CH$_3$), 2.49 (s, 3H, Mes-CH$_3$), 2.12 (s, 3H, Mes-CH$_3$), 2.09 (s, 3H, Mes-CH$_3$), 1.87 (d, $^3J_{HH}$=6 Hz, Ru=CHCH$_3$).

$^{13}$C{$^1$H} NMR (101 MHz, C$_6$D$_6$): δ 314.2, (Ru=CH), 186.9 (NCH), 167.3 (NCN), 141.6 (C$_{ipso}$), 139.8 (C$_{ipso}$), 139.0 (C$_{ipso}$), 138.6 (C$_{ipso}$), 130.7 (p-NO$_2$—C$_6$H$_4$) 129.7 (Mes-CH), 129.5 (Mes-CH), 129.2 (Mes-CH), 128.8 (Mes-CH), 121.5 (OCO—CH), 121.3 (OCO—CH), 121.1 (p-NO$_2$—C$_6$H$_4$), 72.7 (OCO—CH$_2$), 71.5 (OCO—CH$_2$), 58.0 (OCO—CH$_3$), 57.9 (OCO—CH$_3$), 50.8 (OCO—CH$_2$), 50.7 (OCO—CH$_2$), 49.5 (SIMes-CH$_2$), 46.3 (Ru=CHCH$_3$), 20.6 (Mes-CH$_3$), 20.5 (Mes-CH$_3$), 20.1 (Mes-CH$_3$), 19.5 (Mes-CH$_3$), 18.7 (Mes-CH$_3$), 18.6 (Mes-CH$_3$).

I.8 Synthesis of Complex (I-5)

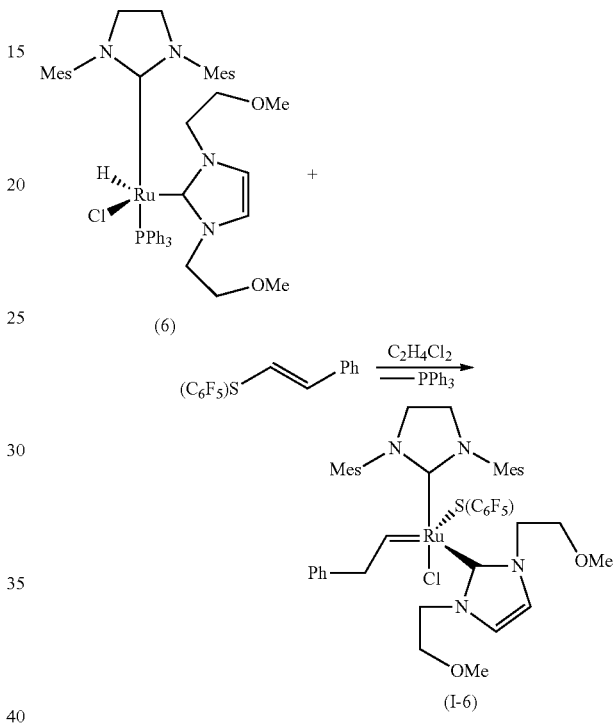

(I-6)

Pentafluorophenyl benzyl sulfide (0.068 g, 0.224 mmol) was added to a solution of Complex (6) (0.100 g, 0.112 mmol) in 2 mL C$_6$H$_5$Br at room temperature. The solution was then stirred for 24 hours before the solution was added dropwise to 15 mL of cold pentane, while stirring, to precipitate the product. Complex (I-5) was collected as pink/red solid on a fit and dried under vacuum (0.073 g, 70%). X-ray quality crystals were grown from tetrahydrofuran/pentane at 25° C.

$^1$H NMR (400 MHz, C$_6$D$_5$Br): δ 15.65 (dd, $^3J_{HH}$=8 Hz, $^3J_{HH}$=3 Hz, 1H, Ru=CH), 7.06 (s, 1H, Mes-CH), 7.05 (s, 1H, Mes-CH), 6.95 (br s, 1H, OCO—CH), 6.87 (s, 2H, Mes-CH), 6.84 (d, $^3J_{HH}$=2 Hz, 1H, OCO—CH), 6.80 (br s, 1H, C$_6$H$_5$), 6.75 (br s, 2H, C$_6$H$_5$), 6.68 (br s, 2H, C$_6$H$_5$), 4.08 (dd, $^2J_{HH}$=15 Hz, $^3J_{HH}$=3 Hz, 1H, OCO—CH$_2$), 4.00 (dt, $^2J_{HH}$=15 Hz, $^3J_{HH}$=3 Hz, 1H, OCO—CH$_2$), 3.64 (m, 4H, SIMes-CH$_2$), 3.49 (m, 4H, OCO—CH$_2$), 3.32 (m, 2H, OCO—CH$_2$), 3.04 (s, 3H, OCO—CH$_3$), 2.87 (s, 2H, Ru=CHCH$_2$), 2.72 (s, 3H, OCO—CH$_3$), 2.61 (s, 3H, Mes-CH$_3$), 2.23 (s, 6H, 2×Mes-CH$_3$), 2.15 (s, 9H, 3×Mes-CH$_3$).

$^{19}$F{$^1$H} NMR (376 MHz, C$_6$D$_5$Br): δ−131.72 (br s, 1F, o-S(C$_6$F$_5$)), −132.36 (br s, 1F, o-S(C$_6$F$_5$)), −162.33 (t, $^3J_{FF}$=22 Hz, 1F, p-S(C$_6$F$_5$)), −166.25 (br s, 1F, m-S(C$_6$F$_5$)), −166.68 (br s, 1F, m-S(C$_6$F$_5$)).

$^{13}$C{$^1$H} NMR (101. MHz, C$_6$D$_5$Br, partial): δ 309.6 (Ru=CH), 138.0 (C$_{ipso}$), 137.5 (C$_{ipso}$), 137.1 (C$_{ipso}$), 130.0

($C_6H_5$), 129.8 (Mes-CH), 129.6 (Mes-CH), 129.4 ($C_6H_5$), 123.5 ($C_6H_5$), 122.5 (OCO—CH), 121.0 (OCO—CH), 72.9 (OCO—$CH_2$), 72.6 (OCO—$CH_2$), 58.2 (OCO—$CH_3$), 58.1 (OCO—$CH_3$), 58.0 (Ru=$CHCH_2$), 52.1 (SIMes-$CH_2$), 49.7 (OCO—$CH_2$), 49.4 (OCO—$CH_2$), 21.0 (Mes-$CH_3$), 19.6 (Mes-$CH_3$), 18.7 (Mes-$CH_3$).

I.9 Synthesis of Complex (I-6)

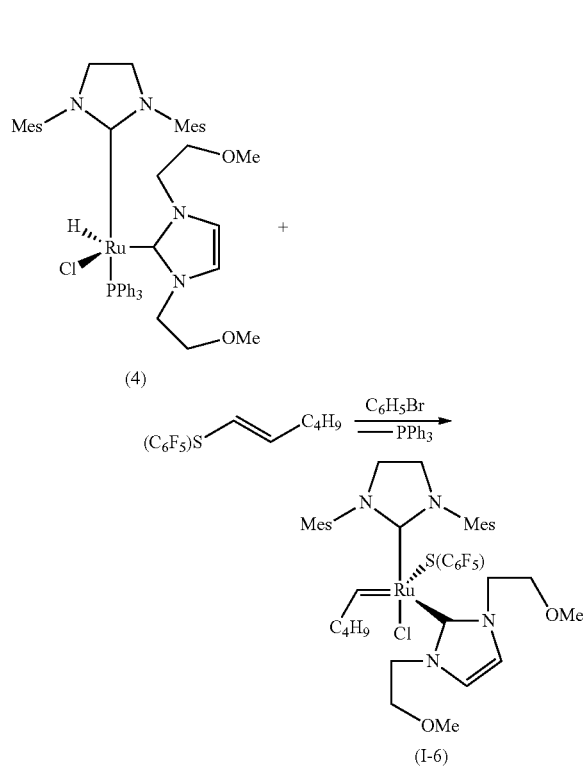

(I-6)

Pentafluorophenyl pentenyl sulfide (0.060 g, 0.224 mmol) was added to a solution of Complex (6) (0.100 g, 0.112 mmol) in 2 mL $C_6H_5Br$ at room temperature. The solution was then stirred for 24 hours before the solution was added dropwise to 15 mL of cold pentane to precipitate the product. Complex (I-6) was collected as orange/brown solid on a fit and dried under vacuum (0.073 g, 73%). X-ray quality crystals were grown from bromobenzene/pentane at 25° C.

$^1$H NMR (400 MHz, $C_6D_5Br$): δ 16.37 (t, $^3J_{HH}$=5 Hz, 1H, Ru=CH), 7.04 (d, $^3J_{HH}$=2 Hz, 1H, OCO—CH), 6.85 (s, 2H, Mes-CH), 6.83 (d, $^3J_{HH}$=2 Hz, 1H, OCO—CH), 6.71 (s, 2H, Mes-CH), 4.16 (m, 1H, OCO—$CH_2$), 3.69 (m, 3H, OCO—$CH_2$), 3.59 (m, 1H, OCO—$CH_2$), 3.55 (m, 4H, SIMes-$CH_2$), 3.37 (m, 1H, OCO—$CH_2$), 3.15 (m, 2H, OCO—$CH_2$), 2.92 (s, 3H, OCO—$CH_3$), 2.90 (s, 3H, OCO—$CH_3$), 2.66 (s, 6H, 2×Mes-$CH_3$), 2.23 (s, 6H, 2×Mes-$CH_3$), 2.16 (s, 6H, 2×Mes-$CH_3$), 1.31 (m, 2H, pentylidene-$CH_2$), 1.13 (m, 2H, pentylidene-$CH_2$), 1.05 (m, 2H, pentylidene-$CH_2$), 0.83 (t, $^3J_{HH}$=7 Hz, 3H, pentylidene-$CH_3$)

$^{19}$F{$^1$H} NMR (376 MHz, $C_6D_5Br$): δ−131.87 (br s, 1F, o-S($C_6F_5$)), −132.41 (br s, 1F, o-S($C_6F_5$)), −162.70 (t, $^3J_{FF}$=22 Hz, 1F, p-S($C_6F_5$)), −166.45 (br s, 1F, m-S($C_6F_5$)), −166.98 (br s, 1F, m-S($C_6F_5$)).

$^{13}$C{$^1$H} NMR (101 MHz, $C_6D_5Br$, partial): δ 315.2 (Ru=CH), 212.6 (NCN), 181.8 (NCN), 137.9 ($C_{ipso}$), 137.4 ($C_{ipso}$), 129.9 (Mes-CH), 129.6 (Mes-CH), 122.6 (OCO—CH), 121.3 (OCO—CH), 73.0 (OCO—$CH_2$), 71.4 (OCO—$CH_2$), 58.5 (OCO—$CH_3$), 58.0 (OCO—$CH_3$), 52.2 (SIMes-$CH_2$), 49.4 (OCO—$CH_2$), 48.3 (OCO—$CH_2$), 29.3 (pentylidene-$CH_2$), 22.9 (pentylidene-$CH_2$), 21.0 (Mes-$CH_3$), 19.6 (Mes-$CH_3$), 18.7 (Mes-$CH_3$), 14.3 (pentylidene-$CH_3$).

I.10 Synthesis of Complex (I-7)

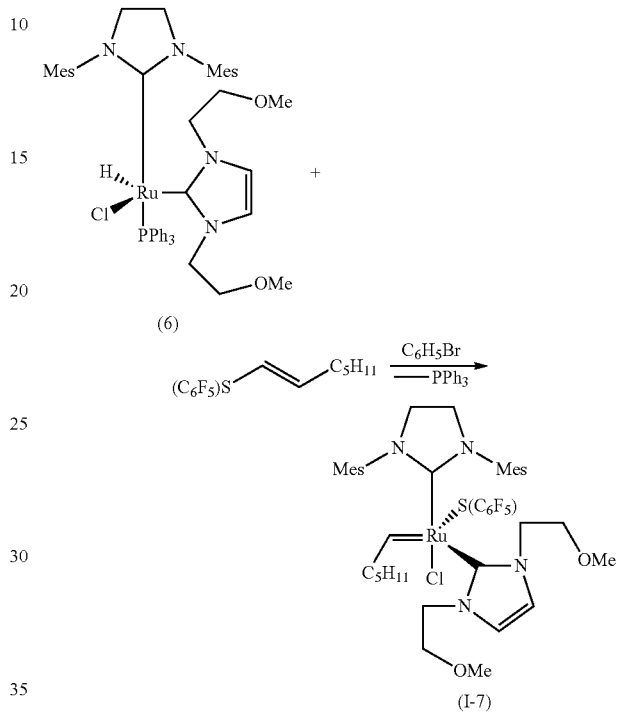

(I-7)

Pentafluorophenyl hexenyl sulfide (0.063 g, 0.224 mmol) was added to a solution of Complex (6) (0.100 g, 0.112 mmol) in 2 mL $C_6H_5Br$ at room temperature. The solution was then stirred for 24 hours before the solution was added dropwise to 15 mL of cold pentane, while stirring, to precipitate the product. The orange/brown solid was collected on a frit and dried under vacuum (0.072 g, 71%). X-ray quality crystals were grown from bromobenzene/pentane at 25° C.

$^1$H NMR (400 MHz, $C_6D_5Br$): δ 16.44 (t, $^3J_{HH}$=5 Hz, 1H, Ru=CH), 7.00 (s, 1H, OCO—CH), 6.85 (s, 2H, Mes-CH), 6.82 (d, $^3J_{HH}$=2 Hz, 1H, OCO—CH), 6.71 (s, 2H, Mes-CH), 4.15 (dd, $^2J_{HH}$=14 Hz, $^3J_{HH}$=4 Hz, 1H, OCO—$CH_2$), 3.67 (m, 2H, OCO—CH), 3.59 (m, 1H, OCO—$CH_2$), 3.50 (m, 4H, SIMes-$CH_2$), 3.33 (m, 1H, OCO—$CH_2$), 3.12 (m, 1H, OCO—$CH_2$), 2.92 (s, 4H, OCO—$CH_2$OCO—$CH_3$), 2.89 (s, 4H, OCO—$CH_2$+OCO—$CH_3$), 2.66 (s, 7H, hexylidene-$CH_2$+2×Mes-$CH_3$), 2.22 (s, 6H, 2×Mes-$CH_3$), 2.15 (s, 7H, hexylidene-$CH_2$+2×Mes-$CH_3$), 1.21 (m, 3H, hexylidene-$CH_2$), 1.07 (m, 3H, hexylidene-$CH_2$), 0.85 (t, $^3J_{HH}$=7 Hz, 3H, hexylidene-$CH_3$).

$^{19}$F{$^1$H} NMR (376 MHz, $C_6D_5Br$): δ−131.83 (br s, 1F, o-S($C_6F_5$)), −132.44 (br s, 1F, o-S($C_6F_5$)), −162.69 (t, $^3J_{FF}$=22 Hz, 1F, p-S($C_6F_5$)), −166.42 (br s, 1F, m-S($C_6F_5$)), −166.96 (br s, 1F, m-S($C_6F_5$)).

$^{13}$C{$^1$H} NMR (101 MHz, $C_6D_5Br$, partial): δ 315.3 (Ru=CH), 212.3 (NCN), 181.8 (NCN), 137.7 ($C_{ipso}$), 137.2 ($C_{ipso}$), 129.3 (Mes-CH), 129.0 (Mes-CH), 122.0 (OCO—CH), 120.7 (OCO—CH), 72.9 (OCO—$CH_2$), 71.4 (OCO—$CH_2$), 58.5 (OCO—$CH_3$), 58.0 (OCO—$CH_3$), 52.3 (SIMes- CH$_2$), 49.4 (OCO—CH$_2$), 48.3 (OCO—CH$_2$), 32.0 (hexylidene-CH$_2$) 26.7 (hexylidene-CH$_2$), 22.8 (hexylidene-CH$_2$), 21.05 (hexylidene-CH$_2$), 21.0 (Mes-CH$_3$), 19.5 (Mes-CH$_3$), 18.7 (Mes-CH$_3$), 14.2 (hexylidene-CH$_3$).

I.11 Synthesis of Complex (I-8)

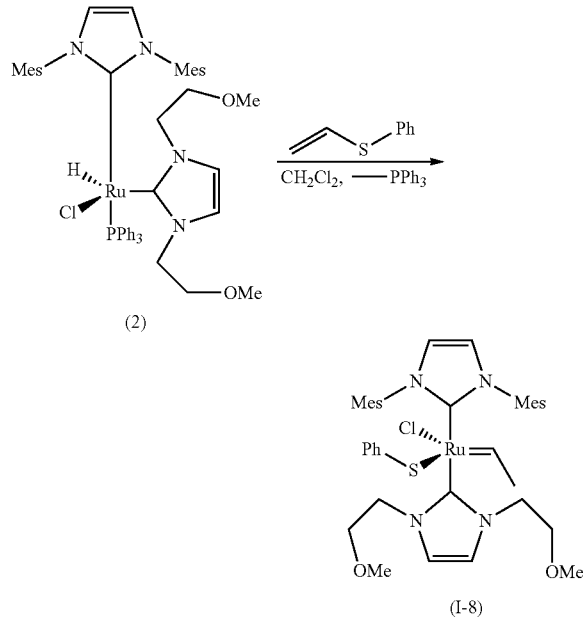

(2)

(I-8)

Phenyl vinyl sulfide (16.7 µL, 0.128 mmol) was added to a solution of Complex (2) (0.100 g, 0.112 mmol) in 5 mL CH$_2$Cl$_2$ at room temperature. The solution was then stirred for 5 hours before the solvent was concentrated to 0.5 mL and 15 mL of pentane was added and the resulting mixture was filtered over a pad of celite. The pentane was then removed in vacuo and the resulting residue was layered with 10 mL of pentane and left standing overnight. The free triphenylphosphine is taken up into the pentane layer yielding Complex (I-8) as a red solid (0.050 g, 59%). X-ray quality crystals were grown from benzene/pentane at 25° C.
$^1$H NMR (500 MHz, C$_6$D$_6$): δ 19.09 (q, $^3J_{HH}$=6 Hz, 1H, Ru=CH), 7.03 (br m, 1H, S(C$_6$H$_5$)), 7.01 (br m, 1H, S(C$_6$H$_5$)), 6.94 (d, $^3J_{HH}$=2 Hz, 1H, OCO—CH), 6.85-6.73 (br m, 7H, (3H) S(C$_6$H$_5$), (4H) Mes-CH), 6.65 (s, 1H, d, $^3J_{HH}$=2 Hz, 1H, OCO—CH), 6.24 (d, $^3J_{HH}$=2 Hz, 1H, Mes-CH), 6.23 (d, $^3J_{HH}$=2 Hz, 1H, Mes-CH), 3.84 (br s, 2H, OCO—CH$_2$), 3.56 (m, 1H, OCO—CH$_2$), 3.46 (m, 1H, OCO—CH$_2$), 3.21 (m, 2H, OCO—CH$_2$), 3.08 (m, 1H, OCO—CH), 2.96 (s, 3H, OCO—CH$_3$), 2.85 (m, 1H, OCO—CH$_2$), 2.77 (s, 3H, OCO—CH$_3$), 2.73 (s, 3H, Mes-CH$_3$), 2.67 (s, 3H, Mes-CH$_3$), 2.48 (s, 6H, Mes-CH$_3$), 2.16 (s, 3H, Mes-CH$_3$), 2.15 (s, 3H, Mes-CH$_3$), 2.08 (d, $^3J_{HH}$=5 Hz, 3H, Ru=CHCH$_3$).
$^{13}$C{$^1$H} NMR (126 MHz, C$_6$D$_6$): δ 313.6 (Ru=CHCH$_3$), 189.8 (NCN), 152.4 (NCN), 139.4 ($C_{ipso}$), 139.2 ($C_{ipso}$), 138.7 ($C_{ipso}$), 137.8 ($C_{ipso}$), 137.2 ($C_{ipso}$), 135.9 (S(C$_6$H$_5$)), 133.0 (S(C$_6$H$_5$)), 129.6 (Mes-CH), 129.4 (Mes-CH), 129.3 (Mes-CH), 129.2 (Mes-CH), 127.0 (S(C$_6$H$_5$)), 124.0 (IMes-CH), 123.6 (IMes-CH), 121.8 (OCO—CH), 121.2 (OCO—CH), 73.5 (OCO—CH$_2$), 72.4 (OCO—CH$_2$), 58.3 (OCO—CH$_3$), 58.2 (OCO—CH$_3$), 49.8 (OCO—CH$_2$), 49.0 (OCO—CH$_2$), 47.5 (Ru=CHCH$_3$), 21.1 (Mes-CH$_3$), 21.0 (Mes-CH$_3$), 20.4 (Mes-CH$_3$), 20.3 (Mes-CH$_3$), 19.1 (Mes-CH$_3$), 19.0 (Mes-CH$_3$).

I.12 Synthesis of Complex (I-9)

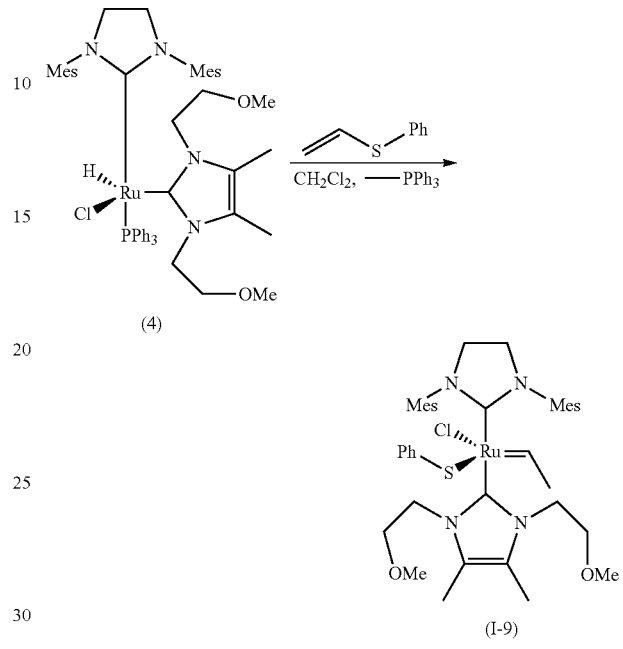

(4)

(I-9)

Phenyl vinyl sulfide (17.0 µL, 0.131 mmol) was added to a solution of Complex (2) (0.100 g, 0.109 mmol) in 5 mL CH$_2$Cl$_2$ at room temperature. The solution was then stirred for one hour before the solvent was concentrated to 0.5 mL and 15 mL of pentane was added and the resulting mixture was filtered over a pad of celite. The pentane was then removed in vacuo and the resulting residue was layered with 10 mL of pentane and left standing overnight. The free triphenylphosphine is taken up into the pentane layer yielding Complex (I-9) as a red solid (0.069 g, 80%). X-ray quality crystals were grown from benzene/pentane at 25° C.
$^1$H NMR (400 MHz, C$_6$D$_6$): δ 19.05 (br s, 1H, Ru=CH), 7.05 (m, 2H, S(C$_6$H$_5$)), 6.97 (s, 1H, Mes-CH), 6.94 (s, 1H, Mes-CH), 6.82 (s, 2H, Mes-CH), 6.67 (m, 3H, S(C$_6$H$_5$)), 3.73-3.03 (br m, 12H, SIMes-CH$_2$+Me$_2$Im(OMe)$_2$-CH$_2$), 2.99 (s, 3H, Me$_2$Im(OMe)$_2$-CH$_3$), 2.94 (s, 3H, Mes-CH$_3$), 2.91 (s, 3H, Mes-CH$_3$), 2.78 (s, 3H, Me$_2$Im(OMe)$_2$-CH$_3$), 2.68 (s, 3H, Mes-CH$_3$), 2.66 (s, 3H, Mes-CH$_3$), 2.25 (s, 3H, Mes-CH$_3$), 2.13 (s, 3H, Mes-CH$_3$), 2.07 (d, $^3J_{HH}$=6 Hz, 3H, Ru=CHCH$_3$). 1.70 (s, 3H, Me$_2$Im(OMe)$_2$-4,5-CH$_3$), 1.44 (s, 3H, Me$_2$Im(OMe)$_2$-4,5-CH$_3$).
$^{13}$C{$^1$H} NMR (101 MHz, C$_6$D$_6$): δ 312.0 (Ru=CHCH$_3$), 223.7 (NCH), 186.3 (NCH), 152.1 ($C_{ipso}$), 140.1 ($C_{ipso}$), 139.7 ($C_{ipso}$), 138.6 ($C_{ipso}$), 138.5 ($C_{ipso}$), 138.2 ($C_{ipso}$), 137.9 ($C_{ipso}$), 137.7 ($C_{ipso}$), 133.4 (S(C$_6$H$_5$)), 130.3 (Mes-CH), 129.9 (Mes-CH), 129.7 (Mes-CH), 129.6 (Mes-CH), 126.3 (S(C$_6$H$_5$)), 126.1 (Me$_2$Im(OMe)$_2$-$C_{ipso}$), 125.5 (Me$_2$Im(OMe)$_2$-$C_{ipso}$), 121.1 (S(C$_6$H$_5$)), 74.5 (Me$_2$Im(OMe)$_2$-CH$_2$), 72.7 (Me$_2$Im(OMe)$_2$-CH$_2$), 58.3 (Me$_2$Im(OMe)$_2$-CH$_3$), 58.2 (Me$_2$Im(OMe)$_2$-CH$_3$), 51.3 (SIMes-CH$_2$), 51.1 (SIMes-CH$_2$), 47.7 (Me$_2$Im(OMe)$_2$-CH$_2$), 46.5 (Ru=CHCH$_3$), 46.0 (Me$_2$Im(OMe)$_2$-CH$_2$), 20.9 (Mes-CH$_3$), 20.6 (Mes-CH$_3$), 20.5 (Mes-CH$_3$), 19.2 (Mes-CH$_3$), 19.1 (Mes-CH$_3$), 9.3 (Me$_2$Im(OMe)$_2$-4,5-CH$_3$), 8.9 (Me$_2$Im(OMe)$_2$-4,5-CH$_3$).

I.13 Synthesis of Complex (I-10)

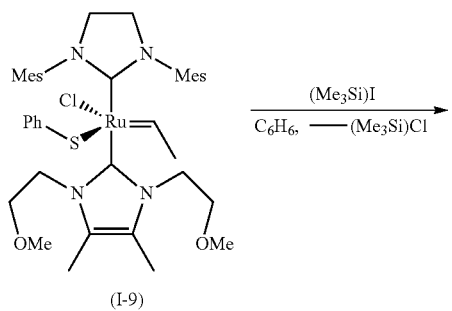

(I-9)

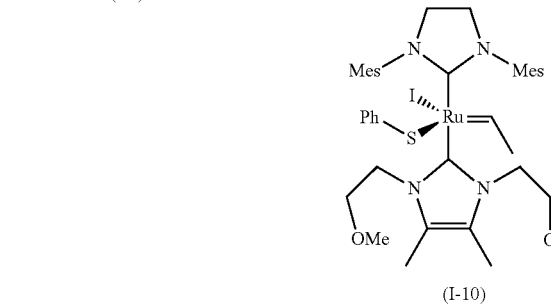

(I-10)

Trimethylsilyl iodide (14.0 μL, 0.104 mmol) was added to a solution of Complex (I-9) (0.065 g, 0.095 mmol) in 2 mL $C_6H_6$ at room temperature. The solution was then stirred for one hour before the solvent was removed and the residue washed with pentane. The pentane was then decanted to yield Complex (I-10) as a red solid (0.038 g, 53%). X-ray quality crystals were grown from benzene/pentane at 25° C.

$^1$H NMR (400 MHz; $C_6D_6$): δ 19.04 (br s, 1H, Ru=CH), 7.13 (br s, 2H, S($C_6H_5$)), 6.94 (s, 1H, Mes-CH), 6.91 (s, 1H, Mes-CH), 6.84 (s, 1H, Mes-CH), 6.77 (s, 1H, Mes-CH), 6.72 (m, 1H, S($C_6H_5$)), 6.64 (br m, 2H, S($C_6H_5$)), 3.70-3.17 (br m, 12H, SIMes-$CH_2$+$Me_2$Im(OMe)$_2$-CH), 2.98 (s, 3H, $Me_2$Im(OMe)$_2$-$CH_3$), 2.95 (br s, 6H, Mes-$CH_3$), 2.88 (s, 3H, $Me_2$Im(OMe)$_2$-$CH_3$), 2.74 (s, 6H, Mes-$CH_3$), 2.23 (s, 3H, Mes-$CH_3$), 2.13 (s, 3H, Mes-$CH_3$), 2.09 (d, $^3J_{HH}$=6 Hz, 3H, Ru=CHC$H_3$), 1.69 (s, 3H, $Me_2$Im(OMe)$_2$-4,5-$CH_3$), 1.47 (s, 3H, $Me_2$Im(OMe)$_2$-4,5-$CH_3$).

$^{13}$C{$^1$H} NMR partial (101 MHz, $C_6D_6$): δ 185.2 (NCN), 139.6 ($C_{ipso}$), 139.3 ($C_{ipso}$), 138.8 ($C_{ipso}$), 138.6 ($C_{ipso}$), 138.3 ($C_{ipso}$), 136.7 (S($C_6H_5$)), br s, S($C_6H_5$)), 130.6 (Mes-CH), 130.1 (Mes-CH), 129.9 (Mes-CH), 129.8 (Mes-CH), 126.6 (S($C_6H_5$)), 126.4 ($Me_2$Im(OMe)$_2$-$C_{ipso}$), 126.1 ($Me_2$Im(OMe)$_2$-$C_{ipso}$), 122.6 (S($C_6H_5$)), 73.5 ($Me_2$Im(OMe)$_2$-$CH_2$), 71.7 ($Me_2$Im(OMe)2-$CH_2$), 58.6 ($Me_2$Im(OMe)$_2$-$CH_3$), 58.3 ($Me_2$Im(OMe)$_2$-$CH_3$), 51.8 (SIMes-$CH_2$), 47.7 ($Me_2$Im(OMe)$_2$-$CH_2$), 46.1 (Ru=CHC$H_3$), 23.0 (Mes-$CH_3$), 21.4 (Mes-$CH_3$), 21.1 (Mes-$CH_3$), 20.6 (Mes-$CH_3$), 19.6 (Mes-$CH_3$), 9.55 ($Me_2$Im(OMe)$_2$-4,5-$CH_3$), 9.05 ($Me_2$Im(OMe)$_2$-4,5-$CH_3$).

II Ring Opening Metathesis Polymerization (ROMP) of 1,5-Cyclooctadiene (1,5-COD)

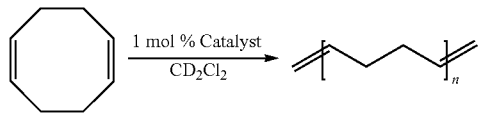

The standard procedure for the ring opening metathesis polymerization of 1,5-cyclooctadiene was as follows: The required amount of the respective inventive Catalyst Complex as indicated below, Grubbs I or Grubbs II catalyst (1 mol %), was weighed out and dissolved in 0.5 mL $CD_2Cl_2$. For the tests that involved the use of an additive (i.e. $BCl_3$, 1M in hexane) the required volume was added and the mixture allowed to stand for 5 min. The solutions were placed in an NMR tube, 1,5-cyclooctadiene (60 μL, 0.50 mmol) was added, the NMR tube was capped and the solution was mixed at the temperature given in the Tables 1-11. Reaction progress was monitored by $^1$H NMR every 2 hours. Reaction progress was determined by integration of the peaks of the starting material versus the product.

TABLE 1

ROMP of 1,5-COD with Catalyst Complex (I-1)
Catalyst: Complex (I-1)

| Additive | Temperature (° C.) | Time (hr) | Conversion (%) |
|---|---|---|---|
| none | 25 | 24 | 0 |
| none | 45 | 2 | 4 |
|  |  | 4 | 8 |
|  |  | 6 | 14 |
|  |  | 24 | 93 |
| 1 mole % $BCl_3$ | 25 | 2 | 54 |
|  |  | 4 | 96 |
|  |  | 6 | 100 |
| 1 mole % $BCl_3$ | 45 | 2 | 98 |
|  |  | 4 | 100 |
| 2 mole % $BCl_3$ | 25 | 2 | 53 |
|  |  | 3 | 71 |
| 2 $BCl_3$ | 45 | 2 | 100 |

TABLE 2

ROMP of 1,5-COD with Catalyst Complex (I-2)
Catalyst: Complex (I-2)

| Additive | Temperature (° C.) | Time (hr) | Conversion (%) |
|---|---|---|---|
| none | 25 | 2 | 6 |
|  |  | 4 | 8 |
|  |  | 6 | 39 |
|  |  | 8 | 55 |
|  |  | 24 | 100 |
| 1 mole % $BCl_3$ | 25 | 2* (15 min) | 100 |

TABLE 3

ROMP of 1,5-COD with Catalyst Complex (I-3)
Catalyst: Complex (I-3)

| Additive | Temperature (° C.) | Time (hr) | Conversion (%) |
|---|---|---|---|
| none | 25 | 24 | 0 |
| none | 45 | 2 | 5 |
|  |  | 4 | 13 |
|  |  | 6 | 23 |
|  |  | 8 | 36 |
|  |  | 24 | 100 |
| 1 mole % $BCl_3$ | 25 | 2 | 30 |
|  |  | 4 | 56 |
|  |  | 6 | 83 |
|  |  | 8 | 100 |
| 1 mole % $BCl_3$ | 45 | 2 | 100 |

TABLE 4

ROMP of 1,5-COD With Catalyst Complex (I-4)
Catalyst: Complex (I-4)

| Additive | Temperature (° C.) | Time (hr) | Conversion (%) |
|---|---|---|---|
| none | 25 | 24 | 0 |
| none | 45 | 2 | 3 |
|  |  | 4 | 9 |
|  |  | 6 | 14 |
|  |  | 24 | 58 |
| 1 mole % BCl$_3$ | 25 | 2 | 100 |
| 1 mole % BCl$_3$ | 45 | 2 | 100 |

TABLE 5

ROMP of 1,5-COD with Catalyst Complex (I-5)
Catalyst: Complex (I-5)

| Additive | Temperature (° C.) | Time (hr) | Conversion (%) |
|---|---|---|---|
| none | 25 | 2 | 14 |
|  |  | 4 | 23 |
|  |  | 6 | 30 |
|  |  | 8 | 37 |
|  |  | 24 | 79 |
| none | 45 | 2 | 79 |
|  |  | 4 | 89 |
|  |  | 6 | 93 |
| 1 mole % BCl$_3$ | 25 | 2 | 64 |
|  |  | 4 | 83 |
|  |  | 6 | 95 |
|  |  | 8 | 100 |
| 1 mole % BCl$_3$ | 45 | 0.5 | 100 |
| 2 mole % BCl$_3$ | 25 | 2 | 42 |
|  |  | 4 | 73 |
|  |  | 6 | 89 |
|  |  | 8 | 97 |

TABLE 6

ROMP of 1,5-COD with Catalyst Complex (I-6)
Catalyst: Complex (I-6)

| Additive | Temperature (° C.) | Time (hr) | Conversion (%) |
|---|---|---|---|
| none | 25 | 2 | 38 |
|  |  | 4 | 58 |
|  |  | 6 | 71 |
|  |  | 8 | 80 |
|  |  | 24 | 95 |
| 1 mole % BCl$_3$ | 25 | 2 | 100 |

TABLE 7

ROMP of 1,5-COD with Catalyst Complex (I-7)
Catalyst: Complex (I-7)

| Additive | Temperature (° C.) | Time (hr) | Conversion (%) |
|---|---|---|---|
| none | 25 | 2 | 71 |
|  |  | 4 | 62 |
|  |  | 6 | 84 |
|  |  | 8 | 90 |
|  |  | 24 | 93 |
| 1 mole % BCl$_3$ | 25 | 2* (15 min) | 100 |
| 2 mole % BCl$_3$ | 25 | 2 | 77 |
|  |  | 4 | 93 |
|  |  | 6 | 100 |

TABLE 8

ROMP of 1,5-COD with Catalyst Complex (I-8)
Catalyst: Complex (I-8)

| Additive | Temperature (° C.) | Time (hr) | Conversion (%) |
|---|---|---|---|
| none | 25 | 2 | 0 |
| none | 45 | 2 | 6 |
|  |  | 4 | 11 |
|  |  | 6 | 16 |
|  |  | 8 | 21 |
|  |  | 24 | 69 |
| 1 mole % BCl$_3$ | 25 | 2 | 11 |
|  |  | 4 | 16 |
|  |  | 6 | 21 |
|  |  | 8 | 30 |
|  |  | 24 | 92 |
| 1 mole % BCl$_3$ | 45 | 2 | 26 |
|  |  | 4 | 64 |
|  |  | 6 | 90 |
|  |  | 8 | 100 |
| 2 mole % BCl$_3$ | 25 | 2 | 70 |
|  |  | 4 | 92 |
|  |  | 6 | 100 |
| 2 mole % BCl$_3$ | 45 | 2 | 100 |

TABLE 9

ROMP of 1,5-COD with Catalyst Complex (I-9)
Catalyst: Complex (I-9)

| Additive | Temperature (° C.) | Time (hr) | Conversion (%) |
|---|---|---|---|
| none | 25 | 24 | 0 |
| none | 45 | 2 | 54 |
|  |  | 4 | 100 |
| 1 mole % BCl$_3$ | 25 | 0.5 | 21 |
|  |  | 2 | 61 |
|  |  | 4 | 92 |
|  |  | 6 | 100 |
| 1 mole % BCl$_3$ | 45 | 0.5 | 100 |

TABLE 10

ROMP of 1,5-COD with Catalyst Complex (I-10)
Catalyst: Complex (I-10)

| Additive | Temperature (° C.) | Time (hr) | Conversion (%) |
|---|---|---|---|
| none | 25 | 2 | 0 |
|  |  | 4 | 3 |
|  |  | 6 | 9 |
|  |  | 8 | 15 |
|  |  | 24 | 68 |
| 1 mole % BCl$_3$ | 25 | 0.25 | 85 |
|  |  | 2 | 100 |

"*" the above Tables 1 to 10 means at catalyst is not active anymore after this point.

TABLE 11

ROMP of 1,5-COD with Grubbs I or Grubbs II catalysts
(Comparison examples)
Catalyst: Grubbs I or Grubbs II

| Additive | Catalyst | Temperature (° C.) | Time (hr) | Conversion (%) |
|---|---|---|---|---|
| none | Grubbs I | 25 | 0.5 | 67 |
|  |  |  | 3 | 83 |
|  |  |  | 7 | 91 |
| none | Grubbs II | 25 | 5 min | 100 |

III Ring Closing Metathesis (RCM) of Diethyl Diallylmalonate

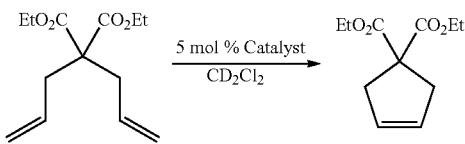 [SMILES: C=CCC(CC=C)(C(=O)OCC)C(=O)OCC ; "CD2Cl2" ; CCOC(=O)C1(C(=O)OCC)CC=CC1]

The standard procedure for the ring closing metathesis of diethyl diallylmalonate was as follows: The required amount of catalyst (5 mol %) mentioned in Tables 12-22 was weighed out and dissolved in 0.5 mL. $CD_2Cl_2$. For the tests that involved the use of an additive (i.e. $BCl_3$, 1M in hexane) the required volume was added and the mixture allowed to stand for 5 min. The solution was placed in an NMR tube, diethyl diallylmalonate (20 μL, 0.50 mmol) was added, the NMR tube was capped and the solution was mixed. Reaction progress was monitored by $^1H$ NMR every 2 hours. Reaction progress was determined by integration of the olefinic peaks of the starting material versus the product.

TABLE 12

RCM of diethyl diallylmalonate with Catalyst Compound (I-1)
Catalyst: Compound (I-1)

| Additive | Temperature (° C.) | Time (hr) | Conversion (%) |
|---|---|---|---|
| none | 25 | 24 | 0 |
| none | 45 | 24 | 0 |
| 5 mole % $BCl_3$ | 25 | 2 | 0 |
|  |  | 24 | 14 |
| 5 mole % $BCl_3$ | 45 | 2 | 5 |
|  |  | 4 | 16 |
|  |  | 6 | 34 |
|  |  | 8 | 47 |
|  |  | 24 | 88 |
| 10 mole % $BCl_3$ | 25 | 2 | 4 |
|  |  | 4 | 6 |
|  |  | 6 | 10 |
|  |  | 8 | 12 |
|  |  | 24 | 28 |
| 10 mole % $BCl_3$ | 45 | 2 | 17 |
|  |  | 4 | 41 |
|  |  | 6 | 54 |
|  |  | 8 | 59 |
|  |  | 24 | 67 |

TABLE 13

RCM of diethyl diallylmalonate with Catalyst Complex (I-2)
Catalyst: Complex (I-2)

| Additive | Temperature (° C.) | Time (hr) | Conversion (%) |
|---|---|---|---|
| none | 25 | 2 | 0 |
|  |  | 24 | 5 |
| 5 mole % $BCl_3$ | 25 | 2 | 81 |
|  |  | 4 | 95 |
|  |  | 6 | 100 |

TABLE 14

RCM of diethyl diallylmalonate with Catalyst Complex (I-3)
Catalyst: Complex (I-3)

| Additive | Temperature (° C.) | Time (hr) | Conversion (%) |
|---|---|---|---|
| none | 25 | 24 | 0 |
| none | 45 | 2 | 6 |
|  |  | 4 | 10 |
|  |  | 6 | 13 |
|  |  | 8 | 16 |
| 5 mole % $BCl_3$ | 25 | 2 | 0 |
|  |  | 4 | 3 |
|  |  | 6 | 7 |
|  |  | 8 | 15 |
|  |  | 24 | 33 |
| 5 mole % $BCl_3$ | 45 | 2 | 63 |
|  |  | 4 | 91 |
|  |  | 6 | 100 |

TABLE 15

RCM of diethyl diallylmalonate with Catalyst Complex (I-4)
Catalyst: Complex (I-4)

| Additive | Temperature (° C.) | Time (hr) | Conversion (%) |
|---|---|---|---|
| none | 25 | 24 | 0 |
| none | 45 | 24 | 0 |
| 5 mole % $BCl_3$ | 25 | 24 | 10 |
| 5 mole % $BCl_3$ | 45 | 2 | 16 |
|  |  | 4 | 24 |
|  |  | 6 | 28 |
|  |  | 8 | 29 |
|  |  | 24 | 52 |

TABLE 16

RCM of diethyl diallylmalonate with Catalyst Complex (I-5)
Catalyst: Compound (I-5)

| Additive | Temperature (° C.) | Time (hr) | Conversion (%) |
|---|---|---|---|
| none | 25 | 2 | 0 |
|  |  | 24 | 4 |
| none | 45 | 2 | 2 |
|  |  | 4 | 4 |
|  |  | 6 | 6 |
|  |  | 8 | 8 |
|  |  | 24 | 17 |
| 5 mole % $BCl_3$ | 25 | 2 | 15 |
|  |  | 4 | 51 |
|  |  | 6 | 72 |
|  |  | 8 | 81 |
|  |  | 24 | 93 |

TABLE 16-continued

RCM of diethyl diallylmalonate with Catalyst Complex (I-5)
Catalyst: Compound (I-5)

| Additive | Temperature (° C.) | Time (hr) | Conversion (%) |
|---|---|---|---|
| 5 mole % BCl$_3$ | 45 | 2 | 100 |
| 10 mole % BCl$_3$ | 25 | 2 | 3 |
|  |  | 4 | 7 |
|  |  | 6 | 13 |
|  |  | 8 | 22 |
|  |  | 24 | 57 |
| 10 mole % BCl$_3$ | 45 | 2 | 67 |
|  |  | 4 | 87 |
|  |  | 6 | 92 |

TABLE 17

RCM of diethyl diallylmalonate with Catalyst Complex (I-6)
Catalyst: Complex (I-6)

| Additive | Temperature (° C.) | Time (hr) | Conversion (%) |
|---|---|---|---|
| none | 25 | 24 | 7 |
| none | 45 | 2 | 10 |
|  |  | 4 | 16 |
|  |  | 6 | 24 |
|  |  | 8 | 30 |
|  |  | 24 | 60 |
| 5 mole % BCl$_3$ | 25 | 2 | 12 |
|  |  | 4 | 20 |
|  |  | 6 | 32 |
|  |  | 8 | 52 |
|  |  | 24 | 88 |
| 5 mole % BCl$_3$ | 45 | 2 | 100 |

TABLE 18

RCM of diethyl diallylmalonate with Catalyst Complex (I-7)
Catalyst: Complex (I-7)

| Additive | Temperature (° C.) | Time (hr) | Conversion (%) |
|---|---|---|---|
| none | 25 | 2 | 1 |
|  |  | 24 | 15 |
| none | 45 | 2 | 9 |
|  |  | 4 | 14 |
|  |  | 6 | 19 |
|  |  | 8 | 25 |
|  |  | 24 | 56 |
| 5 mole % BCl$_3$ | 25 | 2 | 28 |
|  |  | 4 | 62 |
|  |  | 6 | 85 |
|  |  | 8 | 90 |
|  |  | 24 | 93 |
| 5 mole % BCl$_3$ | 45 | 2 | 100 |
| 10 mole % BCl$_3$ | 25 | 2 | 6 |
|  |  | 4 | 17 |
|  |  | 6 | 28 |
|  |  | 8 | 41 |
|  |  | 24 | 86 |
| 10 mole % BCl$_3$ | 45 | 2 | 83 |
|  |  | 4 | 100 |

TABLE 19

RCM of diethyl diallylmalonate with Catalyst Complex (I-8)
Catalyst: Complex (I-8)

| Additive | Temperature (° C.) | Time (hr) | Conversion (%) |
|---|---|---|---|
| none | 25 | 24 | 0 |
| none | 45 | 24 | 0 |
| 5 mole % BCl$_3$ | 25 | 24 | 0 |
| 5 mole % BCl$_3$ | 45 | 2 | 5 |
|  |  | 4 | 11 |
|  |  | 6 | 14 |
|  |  | 8 | 21 |
|  |  | 24 | 100 |
| 10 mole % BCl$_3$ | 25 | 2 | 3 |
|  |  | 4 | 7 |
|  |  | 6 | 12 |
|  |  | 8 | 17 |
|  |  | 24 | 46 |
| 10 mole % BCl$_3$ | 45 | 2 | 19 |
|  |  | 4 | 44 |
|  |  | 6 | 49 |
|  |  | 8 | 51 |
|  |  | 24 | 75 |

TABLE 20

RCM of diethyl diallylmalonate with Catalyst Complex (I-9)
Catalyst: Complex (I-9)

| Additive | Temperature (° C.) | Time (hr) | Conversion (%) |
|---|---|---|---|
| none | 25 | 24 | 0 |
| none | 45 | 2 | 7 |
|  |  | 4 | 12 |
| 5 mole % BCl$_3$ | 25 | 2 | 5 |
|  |  | 4 | 13 |
|  |  | 6 | 28 |
|  |  | 8 | 47 |
|  |  | 24 | 79 |
| 5 mole % BCl$_3$ | 45 | 0.5 | 42 |
|  |  | 2 | 100 |

TABLE 21

RCM of diethyl diallylmalonate with Catalyst Complex (I-10)
Catalyst: Complex (I-10)

| Additive | Temperature (° C.) | Time (hr) | Conversion (%) |
|---|---|---|---|
| none | 25 | 24 | 0 |
| 5 mole % BCl$_3$ | 25 | 2 | 100 |

TABLE 22

RCM of diethyl diallylmalonate with Grubbs I or Grubbs II Catalyst
(Comparative Examples)
Catalyst: Grubbs I or Grubbs II

| Additive | Catalyst | Amount of Catalyst (mol %) | Temperature (° C.) | Time (hr) | Conversion (%) |
|---|---|---|---|---|---|
| none | Grubbs I | 5.5 | 25 | 0.5 | 83 |
| none | Grubbs II | 4 | 25 | 0.5 | 100 |

IV Cross Metathesis (CM) of 5-Hexenyl Acetate and Methyl Acrylate

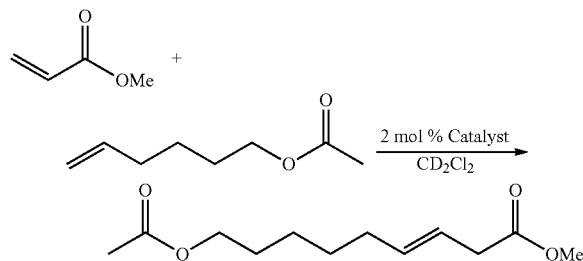

The standard procedure for cross metathesis of 5-hexenyl acetate and methyl acrylate was as follows: The required amount of catalyst (2 mol %) mentioned in Tables 23 to 33 was weighed out and dissolved in 0.5 mL $CD_2Cl_2$. For the tests that involved the use of an additive (i.e. $BCl_3$, 1M in hexane) the required volume was added and the mixture allowed to stand for 5 min. The solution was placed in an NMR tube and a mixture of 5-hexenyl acetate (20 μL, 0.12 mmol) and methyl acrylate (10 μL, 0.11 mmol) was added and the solution was mixed at the temperature mentioned in Tables 11 to 14. Reaction progress was monitored by $^1$H NMR every 2 hours. Reaction progress was determined by integration of the olefinic peaks of the starting material versus the product.

TABLE 23

CM of 5-hexenyl acetate and methyl acrylate with Catalyst Complex (I-1)
Catalyst: Complex (I-1)

| Additive | Temperature (° C.) | Time (hr) | Conversion (%) |
|---|---|---|---|
| none | 25 | 24 | 0 |
| none | 45 | 24 | 0 |
| 2 mole % $BCl_3$ | 25 | 2 | 0 |
| | | 6 | 13 |
| | | 8 | 24 |
| | | 24 | 26 |
| 2 mole % $BCl_3$ | 45 | 2 | 24 |
| | | 4 | 43 |
| | | 6 | 49 |
| | | 8 | 51 |
| | | 24 | 53 |
| 4 mole % $BCl_3$ | 25 | 2 | 15 |
| | | 4 | 20 |
| | | 6 | 24 |
| | | 8 | 31 |
| | | 24 | 41 |
| 4 mole % $BCl_3$ | 45 | 2 | 35 |
| | | 4 | 47 |
| | | 6 | 56 |
| | | 8 | 61 |
| | | 24 | 61 |

TABLE 24

CM of 5-hexellyl acetate and methyl acrylate with Catalyst Complex (I-2)
Catalyst: Complex (I-2)

| Additive | Temperature (° C.) | Time (hr) | Conversion (%) |
|---|---|---|---|
| none | 25 | 24 | 0 |
| 2 mole % $BCl_3$ | 25 | 2 | 47 |
| | | 4 | 63 |
| | | 6 | 72 |
| | | 8 | 75 |
| | | 24 | 78 |

TABLE 25

CM of 5-hexenyl acetate and methyl acrylate with Catalyst Complex (I-3)
Catalyst: Complex (I-3)

| Additive | Temperature (° C.) | Time (hr) | Conversion (%) |
|---|---|---|---|
| none | 25 | 24 | 0 |
| none | 45 | 24 | 0 |
| 2 mole % $BCl_3$ | 25 | 2 | 48 |
| 2 mole % $BCl_3$ | 45 | 4 | 42 |

TABLE 26

CM of 5-hexenyl acetate and methyl acaylate with Catalyst Complex (I-4)
Catalyst: Complex (I-4)

| Additive | Temperature (° C.) | Time (hr) | Conversion (%) |
|---|---|---|---|
| none | 25 | 24 | 0 |
| none | 45 | 24 | 0 |
| 2 mole % $BCl_3$ | 25 | 2 | 0 |
| 2 mole % $BCl_3$ | 45 | 4 | 21 |
| | | 6 | 23 |
| | | 8 | 28 |
| | | 24 | 32 |

TABLE 27

CM of 5-hexenyl acetate and methyl acrylate with Catalyst Complex (I-5)
Catalyst: Complex (I-5)

| Additive | Temperature (° C.) | Time (hr) | Conversion (%) |
|---|---|---|---|
| none | 25 | 24 | 0 |
| none | 45 | 24 | 0 |
| 2 mole % $BCl_3$ | 25 | 2 | 32 |
| | | 4 | 37 |
| | | 6 | 40 |
| 2 mole % $BCl_3$ | 45 | 2 | 47 |
| | | 4 | 50 |
| 4 mole % $BCl_3$ | 25 | 2 | 0 |
| | | 4 | 28 |
| | | 6 | 33 |
| 4 mole % $BCl_3$ | 45 | 2 | 65 |

TABLE 28

CM of 5-hexenyl acetate and methyl acrylate with Catalyst Complex (I-6)
Catalyst: Complex (I-6)

| Additive | Temperature (° C.) | Time (hr) | Conversion (%) |
|---|---|---|---|
| none | 25 | 24 | 0 |
| none | 45 | 24 | 0 |
| 2 mole % $BCl_3$ | 25 | 2 | 15 |
| | | 4 | 18 |
| | | 6 | 21 |
| 2 mole % $BCl_3$ | 45 | 2 | 55 |
| | | 4 | 60 |

TABLE 29

CM of 5-hexenyl acetate and methyl acrylate with Catalyst Complex (I-7)
Catalyst: Complex (I-7)

| Additive | Temperature (° C.) | Time (hr) | Conversion (%) |
|---|---|---|---|
| none | 25 | 24 | 0 |
| none | 45 | 24 | 0 |
| 2 mole % $BCl_3$ | 25 | 2 | 20 |
| | | 4 | 50 |
| | | 6* | 79 |

TABLE 29-continued

CM of 5-hexenyl acetate and methyl acrylate with Catalyst Complex (I-7)
Catalyst: Complex (I-7)

| Additive | Temperature (° C.) | Time (hr) | Conversion (%) |
|---|---|---|---|
| 2 mole % BCl₃ | 45 | 2 | 80 |
|  |  | 4* | 81 |
| 4 mole % BCl₃ | 25 | 2 | 18 |
|  |  | 4 | 28 |
|  |  | 6 | 32 |
|  |  | 8 | 36 |
|  |  | 24 | 53 |
| 4 mole % BCl₃ | 45 | 2 | 61 |
|  |  | 4 | 75 |

TABLE 30

CM of 5-hexenyl acetate and methyl acrylate with Catalyst Complex (I-8)
Catalyst: Complex (I-8)

| Additive | Temperature (° C.) | Time (hr) | Conversion (%) |
|---|---|---|---|
| none | 25 | 24 | 0 |
| none | 45 | 24 | 0 |
| 2 mole % BCl₃ | 25 | 24 | 0 |
| 2 mole % BCl₃ | 45 | 2 | 28 |
| 4 mole % BCl₃ | 25 | 24 | 0 |
| 4 mole % BCl₃ | 45 | 2 | 20 |

TABLE 31

CM of 5-hexenyl acetate and methyl acrylate with Catalyst Complex (I-9)
Catalyst: Complex (I-9)

| Additive | Tempperature (° C.) | Time (hr) | Conversion (%) |
|---|---|---|---|
| none | 25 | 24 | 0 |
| none | 45 | 24 | 0 |
| 2 mole % BCl₃ | 25 | 2 | 38 |
|  |  | 4 | 46 |
|  |  | 6 | 50 |
| 2 mole % BCl₃ | 45 | 2 | 65 |
|  |  | 4 | 72 |

TABLE 32

RCM of diethyl diallylmalonate with Catalyst Complex (I-10)
Catalyst: Complex (I-10)

| Additive | Temperature (° C.) | Time (hr) | Conversion (%) |
|---|---|---|---|
| none | 25 | 2 | 0 |
| 5 mole % BCl₃ | 25 | 2 | 70 |

TABLE 33

CM of 5-hexenyl acetate and methyl acrylate with Grubbs I or Grubbs II
(Comparison examples)
Catalyst: Grubbs I or Grubbs II

| Additive | Catalyst | Temperature (° C.) | Time (hr) | Conversion (%) |
|---|---|---|---|---|
| none | Grubbs I | 25 | 0.5 | 20 |
|  |  |  | 3 | 20 |
|  |  |  | 23 | 22 |
| none | Grubbs II | 25 | 0.5 | 56 |
|  |  |  | 3 | 56 |
|  |  |  | 23 | 60 |

"*" in the above Tables means that the catalyst is not active anymore after this point.

V Cross Metathesis of Nitrite Butadiene Rubber (NBR) and 1-Hexene

The standard procedure for the cross metathesis of nitrile butadiene rubber (NBR) and 1-hexene as performed in the subsequent example series was as follows:

1.5 g of NBR was placed in 13.585 g of chlorobenzene and placed on a shaker for 24 hr to give a 10 wt % NBR solution. 1-hexene (60 mg) was added to the solution and shaken for 1 hr. The catalysts stock solution were prepared by dissolving the required mass of the catalyst in the appropriate amount of chlorobenzene (1 mg/0.5 mL) in a glove box. The appropriate amount of BCl₃ was then added and the solutions were stirred for 5 min before being taken out of the glove box and added to the NBR solutions. Samples were taken at 1, 2, 3, 4, and 24 hr. All volatiles were removed from the samples and the Mn, Mw, and PDI were determined by GPC using a polystyrene calibration curve.

In the Example series the catalysts as shown in Table 34 and the nitrile butadiene rubber as shown in Table 35 were used. The results of the metathesis reactions are shown in Tables 36-39.

TABLE 34

Catalysts used in the metathesis of nitrile rubber

| Catalyst name | Structure | Used in Series |
|---|---|---|
| complex (I-1) | (structure shown) | 1, 2 |
| complex (I-2) | (structure shown) | 3, 4, 5 |
| Grubbs II | (structure shown) | 1 |

Table 35

| | Nitrile butadiene rubbers used | | | |
|---|---|---|---|---|
| | Mw | Mn | PDI | Used in Series |
| Nitrile butadiene rubber ("NBR 1") | 274,892 | 81,704 | 3.4 | 1, 2 |
| Nitrile butadiene rubber ("NBR 2") | 274,127 | 76,435 | 3.58 | 3 |
| Nitrite butadiene rubber ("NBR 3") | 258,407 | 92131 | 2.80 | 4 |
| Nitrile butadiene rubber ("NBR 4") | 250,486 | 92809 | 2.70 | 5 |

TABLE 36

Series 1 (Metathesis of NBR 1 with 1 mg of Catalyst (I-1) (inventive examples; "E") or 1 mg of Grubbs II catalyst (not-inventive; "CE")

| Example | E1 | E2 | E3 | CE4 | E5 | E6 | E7 | CE8 |
|---|---|---|---|---|---|---|---|---|
| Catalyst Type | 1 | 1 | 1 | Grubbs II | 1 | 1 | 1 | Grubbs II |
| Catalyst loading (mg) | 1 | 1 | 1 | 1 | 1 | 1 | 1 | 1 |
| BCl$_3$ (eq) | — | 1 | 2 | — | — | 1 | 2 | — |
| Temperature (° C.) | 25 | 25 | 25 | 25 | 45 | 45 | 45 | 45 |
| 1 hour | | | | | | | | |
| $M_w$ | 251463 | 239901 | 257454 | 79715 | 239544 | 203760 | 220004 | 23572 |
| $M_n$ | 81704 | 87945 | 92493 | 38195 | 87217 | 79590 | 80478 | 15587 |
| PDI | 3.03 | 2.73 | 2.78 | 2.08 | 2.75 | 2.56 | 2.73 | 1.51 |
| 2 hours | | | | | | | | |
| $M_w$ | 254645 | 242248 | 234818 | 57852 | 236063 | 208776 | 230744 | 23070 |
| $M_n$ | 80768 | 79920 | 78027 | 30227 | 90163 | 76132 | 80879 | 14924 |
| PDI | 3.15 | 3.03 | 3.01 | 1.91 | 2.62 | 2.74 | 2.86 | 1.54 |
| 3 hours | | | | | | | | |
| $M_w$ | 242481 | 235890 | 220977 | 48014 | 261429 | 205219 | 231226 | 23617 |
| $M_n$ | 79466 | 78792 | 76794 | 26617 | 82389 | 68843 | 76705 | 15660 |
| PDI | 3.05 | 2.99 | 2.87 | 1.80 | 3.18 | 2.98 | 3.01 | 1.50 |
| 4 hours | | | | | | | | |
| $M_w$ | 247639 | 233097 | — | 42187 | 251319 | 207191 | 217307 | 23396 |
| $M_n$ | 83619 | 78904 | — | 24293 | 85039 | 73459 | 81059 | 15376 |
| PDI | 2.96 | 2.95 | — | 1.73 | 2.95 | 2.82 | 2.68 | 1.52 |
| 24 hours | | | | | | | | |
| $M_w$ | 230887 | 207387 | 190595 | 33137 | 235464 | 170324 | 176084 | 23547 |
| $M_n$ | 76436 | 68363 | 69728 | 20327 | 76485 | 64440 | 66120 | 15523 |
| PDI | 3.02 | 3.03 | 2.74 | 1.63 | 3.08 | 2.64 | 2.66 | 1.51 |

TABLE 37

Series 2 (Metathesis of NBR 1 with either 1 or 2 mg of Catalyst (I-1) (inventive examples) and none, 1, or 2 equivalents of BCl$_3$)

| Example | E9 | E10 | E11 | E12 | E13 | E14 | E15 |
|---|---|---|---|---|---|---|---|
| Catalyst Type | 1 | 1 | 1 | 1 | 1 | 1 | 1 |
| Catalyst loading (mg) | 2 | 2 | 2 | 1 | 1 | 2 | 2 |
| BCl$_3$ (eq) | — | 1 | 2 | 1 | 2 | 1 | 2 |
| Temperature (° C.) | 45 | 45 | 45 | 60 | 60 | 60 | 60 |
| 1 hour | | | | | | | |
| $M_w$ | 232171 | 174585 | 103384 | 161009 | 159130 | 144505 | 96734 |
| $M_n$ | 79230 | 65798 | 48181 | 71575 | 60612 | 57765 | 45494 |
| PDI | 2.93 | 2.65 | 2.14 | 2.28 | 2.62 | 2.50 | 2.12 |
| 2 hours | | | | | | | |
| $M_w$ | 238710 | 170403 | 88016 | 168496 | 146278 | 140819 | 94387 |
| $M_n$ | 89312 | 66748 | 42811 | 63515 | 57841 | 55811 | 44688 |
| PDI | 2.63 | 2.57 | 2.05 | 2.65 | 2.53 | 2.52 | 2.11 |

TABLE 37-continued

Series 2 (Metathesis of NBR 1 with either 1 or 2 mg of Catalyst
(I-1) (inventive examples) and none, 1, or 2 equivalents of $BCl_3$)

| Example | E9 | E10 | E11 | E12 | E13 | E14 | E15 |
|---|---|---|---|---|---|---|---|
| 3 hours | | | | | | | |
| $M_w$ | 229704 | 173333 | 84688 | 162353 | 145277 | 134695 | 93700 |
| $M_n$ | 76869 | 63771 | 41764 | 62346 | 58001 | 53527 | 44210 |
| PDI | 2.99 | 2.73 | 2.02 | 2.60 | 2.50 | 2.51 | 2.12 |
| 4 hours | | | | | | | |
| $M_w$ | 237724 | 169363 | 81692 | 163739 | 140142 | 137471 | 95079 |
| $M_n$ | 76362 | 66043 | 41342 | 62707 | 57362 | 55927 | 45039 |
| PDI | 3.11 | 2.56 | 1.97 | 2.61 | 2.44 | 2.45 | 2.11 |
| 24 hours | | | | | | | |
| $M_w$ | 220694 | 157321 | 76319 | 146666 | 119481 | 125744 | 88450 |
| $M_n$ | 74890 | 62826 | 38766 | 59330 | 52293 | 53898 | 42559 |
| PDI | 2.95 | 2.50 | 1.97 | 2.47 | 2.28 | 2.33 | 2.07 |

TABLE 38

Series 3 (Metathesis of NBR 2 with either 1, 2 or 4 mg
of Catalyst (I-2) and 1, 2 or 10 equivalents of $BCl_3$)

| Series 3 | E16 | E17 | E18 | E19 | E20 | E21 | E22 |
|---|---|---|---|---|---|---|---|
| Catalyst loading (mg) | 1 | 1 | 2 | 2 | 4 | 4 | 4 |
| $BCl_3$ (eq) | 1 | 2 | 1 | 2 | 1 | 2 | 10 |
| Temperature (° C.) | 25 | 25 | 25 | 25 | 25 | 25 | 25 |
| 1 hour | | | | | | | |
| $M_w$ | 192764 | — | 130830 | 147850 | 94154 | 91284 | 50433 |
| $M_n$ | 56442 | — | 45644 | 57351 | 36065 | 38488 | 23883 |
| PDI | 3.42 | — | 2.86 | 2.57 | 2.61 | 2.37 | 2.11 |
| 2 hours | | | | | | | |
| $M_w$ | 144052 | 196035 | 89222 | 121413 | 75112 | 59341 | 39610 |
| $M_n$ | 52546 | 63787 | 37000 | 50193 | 29785 | 26664 | 18853 |
| PDI | 2.74 | 3.07 | 2.41 | 2.41 | 2.52 | 2.26 | 2.10 |
| 3 hours | | | | | | | |
| $M_w$ | 130728 | 170910 | 61950 | 111696 | 64850 | 47615 | 31863 |
| $M_n$ | 45814 | 57585 | 28745 | 43765 | 26476 | 21549 | 16366 |
| PDI | 2.85 | 2.96 | 2.16 | 2.54 | 2.45 | 2.21 | 1.95 |
| 4 hours | | | | | | | |
| $M_w$ | 105571 | 160389 | 50644 | 92844 | 44743 | 37064 | 34862 |
| $M_n$ | 41441 | 58102 | 22815 | 39012 | 20821 | 18093 | 17130 |
| PDI | 2.55 | 2.76 | 2.22 | 2.38 | 2.15 | 2.05 | 2.03 |
| 24 hours | | | | | | | |
| $M_w$ | 50966 | 115686 | 20074 | 35176 | 10175 | 19009 | 23528 |
| $M_n$ | 23361 | 44888 | 10715 | 17330 | 6339 | 10328 | 12254 |
| PDI | 2.18 | 2.58 | 1.83 | 2.03 | 1.60 | 1.83 | 1.92 |

The standard procedure for the cross metathesis of nitrile butadiene rubber (NBR) and 1-hexene as performed in the subsequent example series was as follows:

75 g of NBR was placed in 425 g of chlorobenzene and placed on a shaker for 24 hr to give a 15 wt % NBR solution. 1-hexene (4 g) was added to the solution and shaken for 1 hr. The catalysts stock solution were prepared by dissolving the required mass of the catalyst in the appropriate amount of chlorobenzene (1 mg/0.5 mL) in a glove box. The appropriate amount of $BCl_3$ was then added and the solutions were stirred for 5 min before being taken out of the glove box and added to the NBR solutions. Samples were taken at 1, 2, 3, 4, and 24 hr. All volatiles were removed from the samples and the Mn, Mw, and PDI were determined by GPC using a polystyrene calibration curve.

TABLE 39

Series 4 (Metathesis of NBR 3 with either 5, 10 or 20 mg of Catalyst (I-2) and 1 equivalent of BCl₃)

| | Series 4 | | |
|---|---|---|---|
| | E23 | E24 | E25 |
| Catalyst loading (mg) | 5 | 10 | 20 |
| BCl₃ (eq) | 1 | 1 | 1 |
| Temperature (° C.) | 25 | 25 | 25 |
| 1 hour | | | |
| $M_w$ | 251417 | 249859 | 235756 |
| $M_n$ | 74764 | 75567 | 72404 |
| PDI | 336 | 3.31 | 3.25 |
| 2 hours | | | |
| $M_w$ | 239001 | 238496 | 238940 |
| $M_n$ | 77604 | 77276 | 87209 |
| PDI | 3.06 | 3.09 | 2.74 |
| 3 hours | | | |
| $M_w$ | 234632 | 241662 | 226399 |
| $M_n$ | 76052 | 87186 | 76349 |
| PDI | 3.08 | 2.77 | 2.96 |
| 4 hours | | | |
| $M_w$ | 237812 | 227940 | 226932 |
| $M_n$ | 85683 | 73731 | 88404 |
| PDI | 2.77 | 3.09 | 2.57 |
| 24 hours | | | |
| $M_w$ | 244591 | 229890 | 228049 |
| $M_n$ | 88903 | 79462 | 85037 |
| PDI | 2.75 | 2.89 | 2.68 |

The invention claimed is:

1. A ruthenium-based complex according to general formula (I)

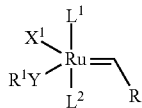

(I)

wherein:
X¹ represents an anionic ligand;
Y is O or S;
R¹ is substituted or unsubstituted $C_6$-$C_{14}$-aryl, an N-heterocyclic carbene ligand or P(R')₃ with R' being identical or different and representing either substituted or unsubstituted, straight chain or branched $C_1$-$C_{14}$ alkyl, substituted or unsubstituted $C_6$-$C_{24}$ aryl, or substituted or unsubstituted $C_3$-$C_{20}$ cycloalkyl;
R represents substituted or unsubstituted, straight chain or branched $C_1$-$C_{14}$-alkyl;
L² represents a ligand having the general structure (Ia*) or (Ib*)

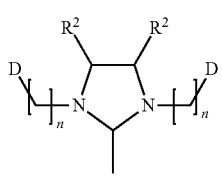

(Ia*)

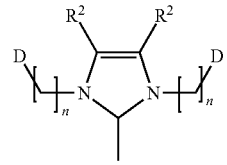

(Ib*)

or a ligand having the general structure (Ic*) or (Id*)

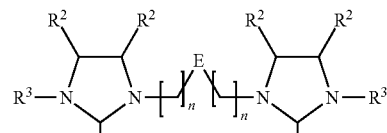

(Ic*)

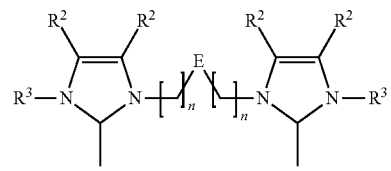

(Id*)

in which formulae (Ia*), (Ib*), (Ic*) and (Id*)
n is identical or different and represents an integer in the range of from 1 to 20,
D is identical or different and represents hydroxy, alkoxy, aryloxy, thiol, thiolate, thioether, selenol, selenoether, amine, phosphine, phosphate, phosphite, arsine, sulfoxide, sulfone, alkyl, phosphinimine, aminophosphine, carbene, selenoxide, imidazoline, imidazolidine, phosphine oxide, phosphine sulfide, phosphine selenide, ketone, ester, pyridyl, substituted pyridyl or any moiety able of acting as a two electron donor;
R³ is identical or different and represents H, alkyl or aryl;
E is identical or different and represents a divalent moiety capable of acting as a two electron donor selected from the group consisting of —O—, —S—, —Se—, —N(R)—, —P(R)—, —As(R)—, —S(=O)—, —PR(=S)—, —PR(=O)—, —C(=O)—, —C(=S)—, 2,6-pyridylene, substituted 2,6-pyridylene, and any other divalent moiety capable of acting as a two electron donor; and
R² are identical or different in a respective moiety (Ia*), (Ib*), (Ic*) or (Id*) and represent H, alkyl, aryl, halide, or in the alternative two R² together with the two adjacent carbon atoms to which they are bound in a moiety (Ia*), (Ib*), (Ic*) or (Id*) form a fused-on five- or six-membered saturated or unsaturated ring; and
L¹ is an N-heterocyclic carbene ligand which is different from general structures (Ia*), (Ib*), (Ic*), and (Id*).

2. The ruthenium-based complex according to claim 1, wherein X¹ is halide, pseudohalide, alkoxide, amide, triflate, phosphate, borate, carboxylate, acetate, halogenated acetate, halogenated alkylsulfonate, tosylate, any weakly coordinating anionic ligands, straight-chain or branched $C_1$-$C_{30}$-alkyl or $C_6$-$C_{24}$-aryl.

3. The ruthenium-based complex according to claim 1, wherein L¹ represents an imidazoline or imidazolidine ligand having a structure corresponding to the general formulae (IIa), or (IIb),

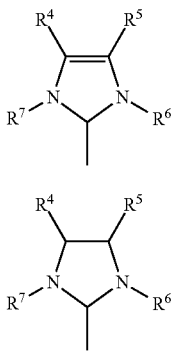

(IIa)

(IIb)

wherein under the proviso that $L^1$ is different from the general formulae (Ia*), (Ib*), (Ic*) and (Id*), $R^4$, $R^5$, $R^6$, $R^7$ are identical or different and are each hydrogen, straight-chain or branched $C_1$-$C_{30}$-alkyl, $C_3$-$C_{20}$-cycloalkyl, $C_2$-$C_{20}$-alkenyl, $C_2$-$C_{20}$-alkynyl, $C_6$-$C_{24}$-aryl, $C_1$-$C_{20}$-carboxylate, $C_1$-$C_{20}$-alkoxy, $C_2$-$C_{20}$-alkenyloxy, $C_2$-$C_{20}$-alkynyloxy, $C_6$-$C_{20}$-aryloxy, $C_2$-$C_{20}$-alkoxycarbonyl, $C_1$-$C_{20}$-alkylthio, $C_6$-$C_{20}$-arylthio, $C_1$-$C_{20}$-alkylsulphonyl, $C_1$-$C_{20}$-alkylsulphonate, $C_1$-$C_{20}$-arylsulphonate or $C_1$-$C_{20}$-alkylsulphinyl or in the alternative $R^6$ and $R^7$ have the above mentioned meanings and at the same time $R^4$ and $R^5$ jointly form a $C_6$-$C_{10}$ cyclic structure together with the two adjacent carbon atoms in the imidazoline or imidazolidine ring, the meanings of the substituents $R^4$, $R^5$, $R^6$, $R^7$ are either unsubstituted or substituted by one or more substituents.

4. The ruthenium-based complex according to claim 3, wherein the imidazoline or imidazolidine ligand has the following structures (III-a) to (III-o), where Ph is in each case a phenyl substituent, Bu is any type of butyl substituent, Mes is in each case a 2,4,6-trimethylphenyl substituent and (iPr)$_2$Ph is in all cases 2,6-diisopropylphenyl

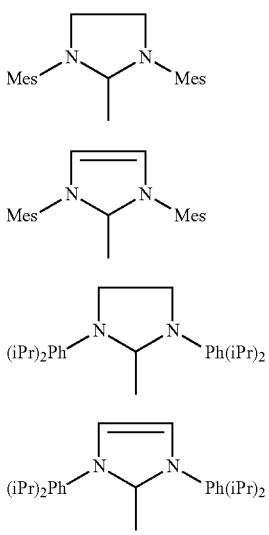

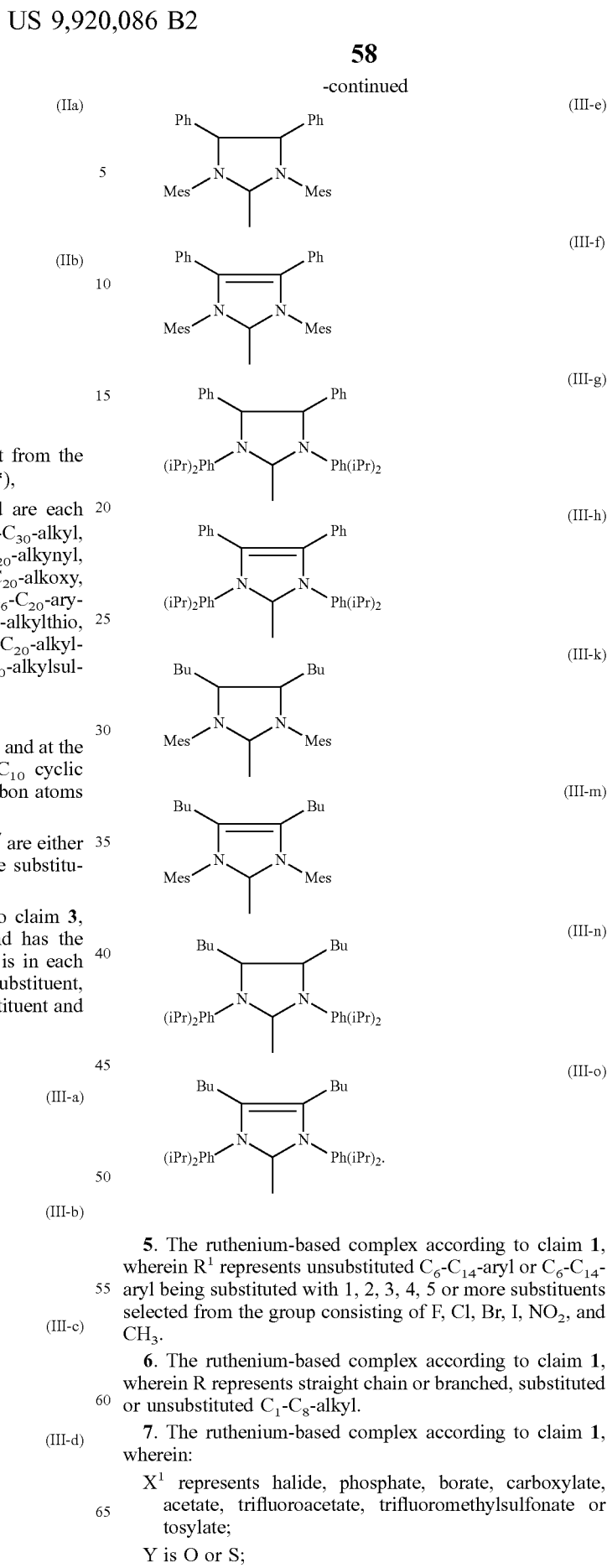

5. The ruthenium-based complex according to claim 1, wherein $R^1$ represents unsubstituted $C_6$-$C_{14}$-aryl or $C_6$-$C_{14}$-aryl being substituted with 1, 2, 3, 4, 5 or more substituents selected from the group consisting of F, Cl, Br, I, NO$_2$, and CH$_3$.

6. The ruthenium-based complex according to claim 1, wherein R represents straight chain or branched, substituted or unsubstituted $C_1$-$C_8$-alkyl.

7. The ruthenium-based complex according to claim 1, wherein:

$X^1$ represents halide, phosphate, borate, carboxylate, acetate, trifluoroacetate, trifluoromethylsulfonate or tosylate;

Y is O or S;

R¹ represents unsubstituted $C_6$-$C_{14}$-aryl or $C_6$-$C_{14}$-aryl being substituted with 1, 2, 3, 4, 5 or more substituents selected from the group consisting of F, Cl, Br, I, $NO_2$, and $CH_3$;

R represents unsubstituted, straight chain or branched $C_1$-$C_5$-alkyl or a straight chain or branched $C_1$-$C_5$-alkyl which is substituted by $C_6$-$C_{14}$-aryl;

L¹ represents an imidazoline or imidazolidine ligand having a structure corresponding to the general formulae (IIa), or (IIb),

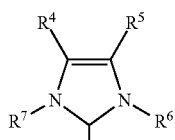

(IIa)

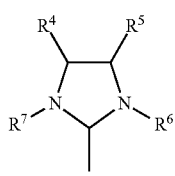

(IIb)

wherein under the proviso that L¹ is different from the general formulae (Ia*), (Ib*), (Ic*) and (Id*) as defined for L², R⁴, R⁵, R⁶, R⁷ are identical or different and are each hydrogen, straight-chain or branched $C_1$-$C_{30}$-alkyl, $C_3$-$C_{20}$-cycloalkyl, $C_2$-$C_{20}$-alkenyl, $C_2$-$C_{20}$-alkynyl, $C_6$-$C_{24}$-aryl, $C_1$-$C_{20}$-carboxylate, $C_1$-$C_{20}$-alkoxy, $C_2$-$C_{20}$-alkenyloxy, $C_2$-$C_{20}$-alkynyloxy, $C_6$-$C_{20}$-aryloxy, $C_2$-$C_{20}$-alkoxycarbonyl, $C_1$-$C_{20}$-alkylthio, $C_6$-$C_{20}$-arylthio, $C_1$-$C_{20}$-alkylsulphonyl, $C_1$-$C_{20}$-alkylsulphonate, $C_6$-$C_{20}$-arylsulphonate or $C_1$-$C_{20}$-alkylsulphinyl or in the alternative R⁶, R⁷ have the above mentioned meanings and at the same time R⁴ and R⁵ jointly form a $C_6$-$C_{10}$ cyclic structure together with the two adjacent carbon atoms in the imidazoline or imidazolidine ring; and L² represents either a ligand of the structure (Ia*) or (Ib*) in which n is identical or different and represents an integer of 1 to 5, and D is identical or different and represents $C_1$-$C_{10}$-alkoxy or $C_6$-$C_{14}$-aryloxy, or a ligand of the structure (Ic*) or (Id*) in which n is identical or different and represents an integer of 1 to 5; and E is identical or different and represents oxygen or sulfur; and R³ is identical or different and represents $C_1$-$C_{10}$ alkyl or $C_6$-$C_{14}$ aryl, wherein all aforementioned can be unsubstituted or substituted by one or more substituents, with R² being identical or different in a respective moiety (Ia*), (Ib*), (Ic*) or (Id*) and representing H, $C_1$-$C_{10}$-alkyl, $C_6$-$C_{14}$-aryl, halide, or in the alternative two R² together with the two adjacent carbon atoms to which they are bound in a moiety (Ia*), (Ib*), (Ic*) or (Id*) form a fused-on five- or six-membered saturated or unsaturated ring.

8. The ruthenium-based complex according to claim 1, wherein the complex has the structure of formulae (I-1) to (I-10)

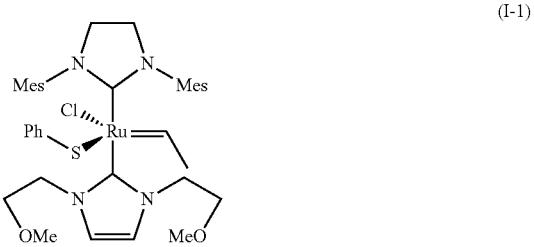

(I-1)

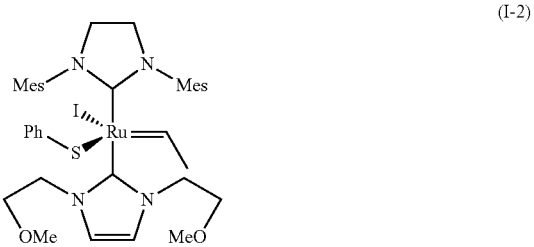

(I-2)

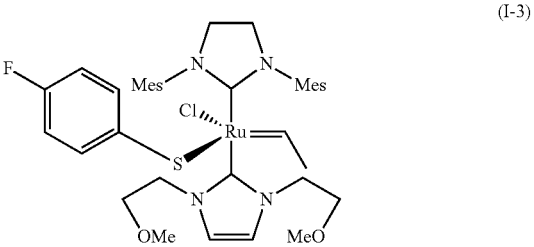

(I-3)

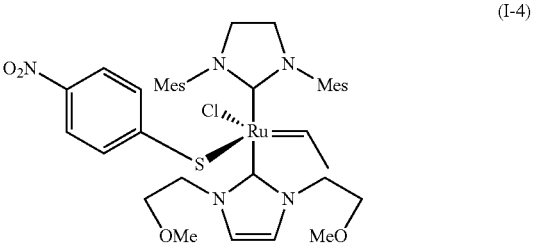

(I-4)

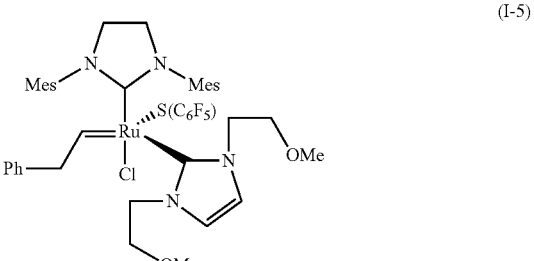

(I-5)

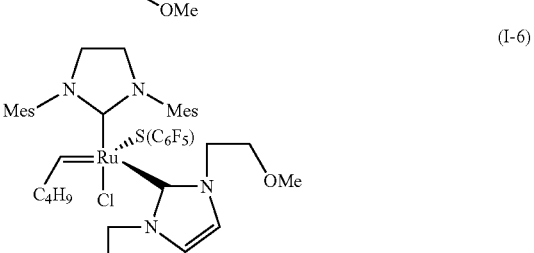

(I-6)

-continued (I-7)
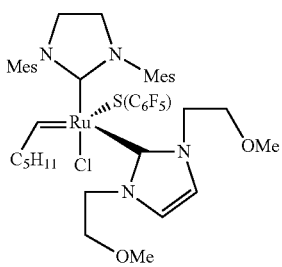

(I-8)
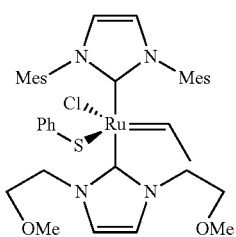

(I-9)
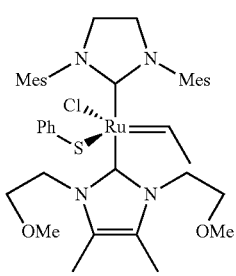

(I-10)
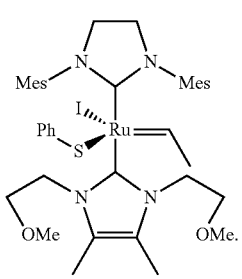

9. A catalyst system comprising at least one ruthenium-based complex of the general formula (I) according to claim 1 and at least one Lewis acid.

10. A process for preparing the ruthenium-based complexes of general formula (I) according to claim 1, the process comprising:

reacting a compound of general formula (IV)

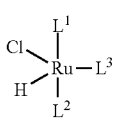
(IV)

in which $L^2$ means a ligand having the general structure (Ia*) or (Ib*)

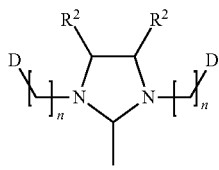
(Ia*)

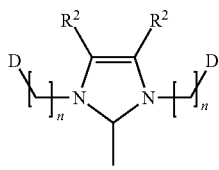
(Ib*)

or a ligand having the general structure (Ic*) or (Id*)

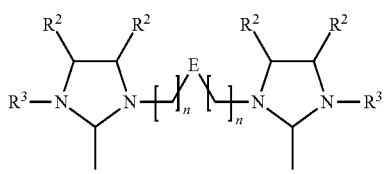
(Ic*)

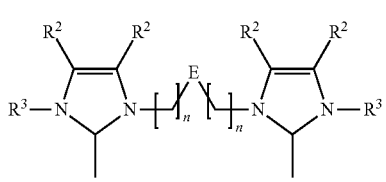
(Id*)

in which formulae (Ia*), (Ib*), (Ic*) and (Id*)
n is identical or different and represents an integer in the range of from 1 to 20;
D is identical or different and represents hydroxy, alkoxy, aryloxy, thiol, thiolate, thioether, selenol, selenoether, amine, phosphine, phosphate, phosphite, arsine, sulfoxide, sulfone, alkyl, phosphinimine, aminophosphine, carbene, selenoxide, imidazoline, imidazolidine, phosphine oxide, phosphine sulfide, phosphine selenide, ketone, ester, pyridyl, substituted pyridyl or any moiety able of acting as a two electron donor;
$R^3$ is identical or different and represents H, alkyl or aryl;
E is identical or different and represents a divalent moiety able of acting as a two electron donor selected from the group consisting of —O—, —S—, —Se—, —N(R)—, —P(R)—, —As(R)—, —S(=O)—, —PR(=S)—, —PR(=O)—, —C(=O)—, —C(=S)—, 2,6-pyridylene, substituted 2,6-pyridylene and any other divalent moiety able of acting as a two electron donor; and
$R^2$ are identical or different in a respective moiety (Ia*), (Ib*), (Ic*) or (Id*) and represent H, alkyl, aryl, halide, or in the alternative two $R^2$ together with the two adjacent carbon atoms to which they are bound in a moiety (Ia*), (Ib*), (Ic*) or (Id*) form a fused-on five- or six-membered saturated or unsaturated ring;

$L^1$ is a N-heterocyclic carbene ligand which is different from general structures (Ia*), (Ib*), (Ic*), and (Id*); and $L^3$ represents $P(R')_3$ with R' being identical or different and representing either substituted or unsubstituted, straight chain or branched $C_1$-$C_{14}$ alkyl, substituted or unsubstituted $C_6$-$C_{24}$ aryl, or substituted or unsubstituted $C_3$-$C_{20}$ cycloalkyl, with a compound of general formula (V)

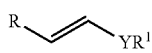    (V)

in which Y and $R^1$ have the same meanings as defined with regard to formula (I), It produce a compound of general formula (VI)

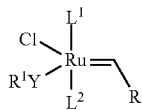    (VI)

in which $L^1$, $L^2$, $R^1$, Y and R have the same meanings as defined with regard to formula (I), and converting the compound of the general formula (VI) with

in which $X^2$ has the same meaning as defined with regard to formula (I) to produce the ruthenium-based complexes of general formula (I).

11. A method of catalysing metathesis reactions, the method comprising contacting C=C double bond containing substrates with at least one ruthenium-based complex according to claim 1 for ring-closing metatheses (RCM), cross metatheses (CM) or ring-opening metatheses (ROMP).

12. The method according to claim 11, wherein:
the substrates are nitrile rubbers being copolymers or terpolymers comprising repeating units of at least one conjugated diene, at least one α,β-unsaturated nitrile monomer, and none, one or more further copolymerizable monomers; and the method further comprises using the ruthenium-based complex together with at least one Lewis acid, of the general formula (Z)

    (Z)

wherein $R^8$ are identical or different and are halogen, unsubstituted or substituted $C_6$-$C_{14}$-aryl, or unsubstituted or substituted $C_6$-$C_{14}$-heteroaryl radicals, wherein at least one of the 6 to 14 C-atoms is replaced by one heteroatom.

13. A process for producing compounds, the process comprising subjecting at least one substrate containing at least one C=C double bond to a metathesis reaction in the presence of the Ruthenium complex according to claim 1.

14. The process for producing compounds according to claim 13, wherein the compounds are nitrile rubbers with a weight average molecular weight $M_w'$, and the substrate is a starting nitrile rubber having a weight average molecular weight $M_w$, and the process comprises subjecting the starting nitrile rubber having a weight average molecular weight $M_w$ to a cross-metathesis reaction in the presence of the Ruthenium-based complex to metathesize the nitrile rubber and produce the nitrile rubbers with the weight average molecular weight $M_w'$, wherein the weight average molecular weight $M_w$ of the starting nitrile rubber $M_w$ is higher than the weight average molecular weight $M_w'$ of the nitrile rubber prepared.

15. The process according to claim 14, further comprising mixing the ruthenium complex of general formula (I) and the substrate(s) in a molar ratio of 1:226 to 1:2.5.

16. The process according to claim 14 wherein the amount of ruthenium complex of general formula (I) is 0.005 to 0.25 phr, wherein phr means parts by weight per 100 parts by weight of the nitrile rubber to be degraded.

17. The catalyst system according to claim 9, wherein the at least one Lewis acid comprises at least one compound of the general formula (Z)

    (Z)

wherein $R^8$ are identical or different and are halogen, unsubstituted or substituted $C_6$-$C_{14}$-aryl, or unsubstituted or substituted $C_6$-$C_{14}$-heteroaryl radicals, wherein at least one of the 6 to 14 C-atoms is replaced by one heteroatom.

18. The catalyst system according to claim 9, wherein the at least one Lewis acid is at least one of $BCl_3$, $BF_3$, $BI_3$, and $B(C_6F_5)_3$.

* * * * *